(12) United States Patent
Dubridge et al.

(10) Patent No.: US 8,658,175 B2
(45) Date of Patent: Feb. 25, 2014

(54) ANTI-EGFR ANTIBODIES AND THEIR USES

(75) Inventors: Robert B. Dubridge, Belmont, CA (US); David B. Powers, Fairfax, CA (US); Charles M. Forsyth, Fremont, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 0 days.

(21) Appl. No.: 12/914,729

(22) Filed: Oct. 28, 2010

(65) Prior Publication Data

US 2011/0117110 A1     May 19, 2011

Related U.S. Application Data

(60) Provisional application No. 61/255,632, filed on Oct. 28, 2009.

(51) Int. Cl.
*A61K 39/395* (2006.01)
*C07K 14/71* (2006.01)

(52) U.S. Cl.
USPC ............... 424/155.1; 424/143.1; 424/136.1; 424/138.1; 514/19.3; 530/387.9; 530/388.22; 530/388.8

(58) Field of Classification Search
None
See application file for complete search history.

(56) References Cited

U.S. PATENT DOCUMENTS

| | | | |
|---|---|---|---|
| 5,942,602 A * | 8/1999 | Wels et al. | |
| 6,129,915 A * | 10/2000 | Wels et al. | |
| 7,060,808 B1 * | 6/2006 | Goldstein et al. | |
| 7,657,380 B2 * | 2/2010 | Lazar et al. | |
| 7,723,484 B2 * | 5/2010 | Beidler et al. | |
| 2003/0224001 A1 | 12/2003 | Goldstein et al. | |
| 2004/0006212 A1 | 1/2004 | Goldstein et al. | |
| 2005/0142133 A1 | 6/2005 | Lazar et al. | |
| 2006/0008883 A1 | 1/2006 | Lazar et al. | |
| 2008/0274114 A1 | 11/2008 | Beidler et al. | |
| 2009/0099339 A1 | 4/2009 | Goldstein et al. | |

FOREIGN PATENT DOCUMENTS

| WO | WO 2009/107129 | 6/2005 |
|---|---|---|
| WO | WO 2005/056759 | 3/2009 |

OTHER PUBLICATIONS

Rudikoff et al., Single amino acid substitution altering antigen-binding specificity, Proc. Nat. Acad. Sci. USA, 79:1979-1983, Mar. 1982.*
MacCallum et al., Antibody-antigen interactions: Contact analysis and binding site topograpy, J. Mol. Biol. 262:732-745, 1996.*
Chao et al., "Fine epitope mapping of anti-epidermal growth factor receptor antibodies through random mutagenesis and yeast surface display," J. Mol. Biol., 342, 539-550 (2004).
Goldstein et al., "Biological efficacy for a chimeric antibody to the epidermal growth factor receptor in a human tumor xenograft model," Clinical Cancer Res., 1, 1311-1318 (1995).
International Search Report dated Apr. 7, 2011 corresponding to International Application No. PCT/US2010/054545.
Kim et al., "Antibody engineering for the development of therapeutic antibodies," Molecules and Cells, 20, 17-29 (2005).
Li et al., "Structural basis for inhibition of the epidermal growth factor receptor by cetuximab," Cancer Cell., 7, 301-311 (2005).
Lippow et al., "Computational design of antibody-affinity improvement beyond in vivo maturation," Nature Biotechnology, 25, 1171-1176 (2007).
Mateo et al., "Humanization of a mouse monoclonal antibody that blocks the epidermal growth factor receptor: recovery of antagonist activity," Immunotechnology, 3, 71-81 (1997).
Watier et al., "Structure-function relationships of the variable domains of monoclonal antibodies approved for cancer treatment," Critical Reviews in Oncology/Hematology, 64, 210-225 (2007).
van Zoelen et al., "Rational Design for the Development of Epidermal Growth Factor Receptor Antagonists," Path. Res. Pract., 192, 761-767 (1996).

\* cited by examiner

*Primary Examiner* — Claire Kaufman
(74) *Attorney, Agent, or Firm* — Dechert LLP

(57) ABSTRACT

The present invention relates to antibodies directed to EGFR and uses of such antibodies, for example, to treat diseases associated with the activity and/or overproduction of EGFR.

41 Claims, 24 Drawing Sheets

C225 (Cetuximab) VH (SEQ ID NO:1)
QVQLKQSGPGLVQPSQSLSITCTVSGFSLTNYGVHWVRQSPGKGLEW
LGVIWSGGNTDYNTPFTSRLSINKDNSKSQVFFKMNSLQSNDTAIYY
CARALTYYDYEFAYWGQGTLVTVSA C225 (Cetuximab) VL (SEQ ID NO:2)
DILLTQSPVILSVSPGERVSFSCRASQSIGTNIHWYQQRTNGSPRLL
IKYASESISGIPSRFSGSGSGTDFTLSINSVESEDIADYYCQQNNNW
PTTFGAGTKLELKR

FIGURE 1A

Hu225 (Humanized M225) VH (SEQ ID NO: 9)
EVQLVESGGGLVQPGGSLRLSCAASGFSLTNYGVHWVRQAPGKGLEW
LGVIWSGGNTDYNTPFTSRLTINKDNSKNTVYLQMNSLRAEDTAVYY
CARALTYYDYEFAYWGQGTLVTVSS Hu225 (Humanized M225) VL (SEQ ID NO: 10)
DILLTQSPGTLSLSPGERATLSCRASQSIGTNIHWYQQKPGQAPRLL
IKYASESISGIPDRFSGSGSGTDFTLTISRLEPEDFAVYYCQQNNNW
PTTFGQGTKLEIKR

FIGURE 1B

| Antibody Chain | CDR No. | Sequence | SEQ ID NO. |
|---|---|---|---|
| Heavy | 1 | N Y G V H | 3 |
| Heavy | 2 | V I W S G G N T D Y N T P F T S | 4 |
| Heavy | 3 | A L T Y Y D Y E F A Y | 5 |
| Light | 1 | R A S Q S I G T N I H | 6 |
| Light | 2 | Y A S E S I S | 7 |
| Light | 3 | Q Q N N N W P T T | 8 |

FIGURE 1C

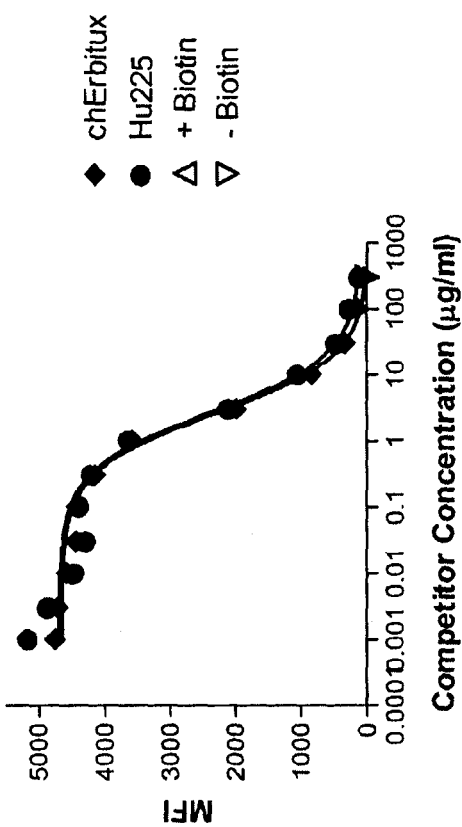
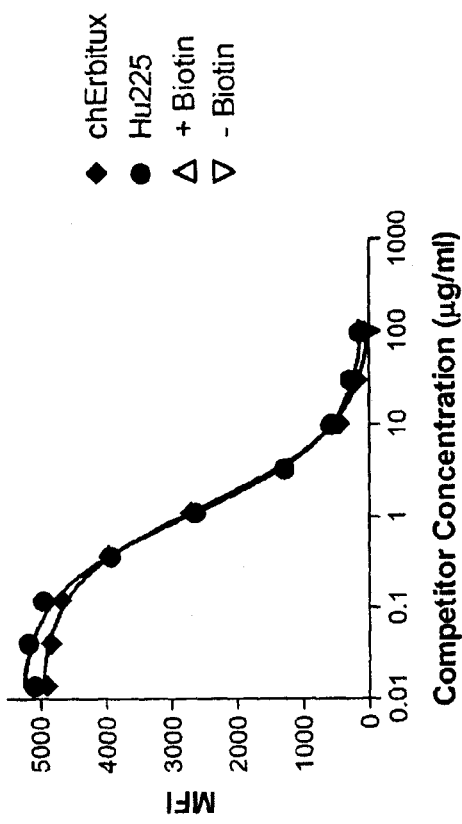
FIGURE 2A

IC 50 (μg/mL)

| Antibody | Trial 1 | Trial 2 | Trial 3 | Average | SD |
|---|---|---|---|---|---|
| Erbitux (cetuximab) | 2.14 | 1.35 | 2.54 | 2.01 | 0.6 |
| Hu225 | 1.71 | 1.06 | 2.62 | 1.79 | 0.4 |

FIGURE 2B

| Cetuximab V_H and V_L peptides tested | | | |
|---|---|---|---|
| SEQ ID NO: | V_H | SEQ ID NO: | V_L |
| 11 | QVQLKQSGPGLVQPS | 12 | DILLTQSPVILSVSP |
| 13 | LKQSGPGLVQPSQSL | 14 | LTQSPVILSVSPGER |
| 15 | SGPGLVQPSQSLSIT | 16 | SPVILSVSPGERVSF |
| 17 | GLVQPSQSLSITCTV | 18 | ILSVSPGERVSFSCR |
| 19 | QPSQSLSITCTVSGF | 20 | VSPGERVSFSCRASQ |
| 21 | QSLSITCTVSGFSLT | 22 | GERVSFSCRASQSIG |
| 23 | SITCTVSGFSLTNYG | 24 | VSFSCRASQSIGTNI |
| 25 | CTVSGFSLTNYGVHW | 26 | SCRASQSIGTNIHWY |
| 27 | SGFSLTNYGVHWVRQ | 28 | ASQSIGTNIHWYQQR |
| 29 | SLTNYGVHWVRQSPG | 30 | SIGTNIHWYQQRTNG |
| 31 | NYGVHWVRQSPGKGL | 32 | TNIHWYQQRTNGSPR |
| 33 | VHWVRQSPGKGLEWL | 34 | HWYQQRTNGSPRLLI |
| 35 | VRQSPGKGLEWLGVI | 36 | QQRTNGSPRLLIKYA |
| 37 | SPGKGLEWLGVIWSG | 38 | TNGSPRLLIKYASES |
| 39 | KGLEWLGVIWSGGNT | 40 | SPRLLIKYASESISG |
| 41 | EWLGVIWSGGNTDYN | 42 | LLIKYASESISGIPS |
| 43 | GVIWSGGNTDYNTPF | 44 | KYASESISGIPSRFS |
| 45 | WSGGNTDYNTPFTSR | 46 | SESISGIPSRFSGSG |
| 47 | GNTDYNTPFTSRLSI | 48 | ISGIPSRFSGSGSGT |
| 49 | DYNTPFTSRLSINKD | 50 | IPSRFSGSGSGTDFT |

FIGURE 4-1

| Cetuximab V_H and V_L peptides tested |||| 
|---|---|---|---|
| SEQ ID NO: | V_H | SEQ ID NO: | V_L |
| 51 | TPFTSRLSINKDNSK | 52 | RFSGSGSGTDFTLSI |
| 53 | TSRLSINKDNSKSQV | 54 | GSGSGTDFTLSINSV |
| 55 | LSINKDNSKSQVFFK | 56 | SGTDFTLSINSVESE |
| 57 | NKDNSKSQVFFKMNS | 58 | DFTLSINSVESEDIA |
| 59 | NSKSQVFFKMNSLQS | 60 | LSINSVESEDIADYY |
| 61 | SQVFFKMNSLQSNDT | 62 | NSVESEDIADYYCQQ |
| 63 | FFKMNSLQSNDTAIY | 64 | ESEDIADYYCQQNNN |
| 65 | MNSLQSNDTAIYYCA | 66 | DIADYYCQQNNNWPT |
| 67 | LQSNDTAIYYCARAL | 68 | DYYCQQNNNWPTTFG |
| 69 | NDTAIYYCARALTYY | 70 | CQQNNNWPTTFGAGT |
| 71 | AIYYCARALTYYDYE | 72 | NNNWPTTFGAGTKLE |
| 73 | YCARALTYYDYEFAY | 74 | NNWPTTFGAGTKLEL |
| 75 | RALTYYDYEFAYWGQ | | |
| 76 | ALTYYDYEFAYWGQG | | |

FIGURE 4-2

| Hu225 V$_H$ and V$_L$ peptides tested ||||
|---|---|---|---|
| SEQ ID NO: | V$_H$ | SEQ ID NO: | V$_L$ |
| 77 | EVQLVESGGGLVQPG | 78 | DILLTQSPGTLSLSP |
| 79 | LVESGGGLVQPGGSL | 80 | LTQSPGTLSLSPGER |
| 81 | SGGGLVQPGGSLRLS | 82 | SPGTLSLSPGERATL |
| 83 | GLVQPGGSLRLSCAA | 84 | TLSLSPGERATLSCR |
| 85 | QPGGSLRLSCAASGF | 86 | LSPGERATLSCRASQ |
| 87 | GSLRLSCAASGFSLT | 88 | GERATLSCRASQSIG |
| 89 | RLSCAASGFSLTNYG | 90 | ATLSCRASQSIGTNI |
| 91 | CAASGFSLTNYGVHW | 92 | SCRASQSIGTNIHWY |
| 93 | SGFSLTNYGVHWVRQ | 94 | ASQSIGTNIHWYQQK |
| 95 | SLTNYGVHWVRQAPG | 96 | SIGTNIHWYQQKPGQ |
| 97 | NYGVHWVRQAPGKGL | 98 | TNIHWYQQKPGQAPR |
| 99 | VHWVRQAPGKGLEWL | 100 | HWYQQKPGQAPRLLI |
| 101 | VRQAPGKGLEWLGVI | 102 | QQKPGQAPRLLIKYA |
| 103 | APGKGLEWLGVIWSG | 104 | PGQAPRLLIKYASES |
| 105 | KGLEWLGVIWSGGNT | 106 | APRLLIKYASESISG |
| 107 | EWLGVIWSGGNTDYN | 108 | LLIKYASESISGIPD |
| 109 | GVIWSGGNTDYNTPF | 110 | KYASESISGIPDRFS |
| 111 | WSGGNTDYNTPFTSR | 112 | SESISGIPDRFSGSG |
| 113 | GNTDYNTPFTSRLTI | 114 | ISGIPDRFSGSGSGT |
| 115 | DYNTPFTSRLTINKD | 116 | IPDRFSGSGSGTDFT |
| 117 | TPFTSRLTINKDNSK | 118 | RFSGSGSGTDFTLTI |

FIGURE 5-1

| Hu225 V$_H$ and V$_L$ peptides tested ||||
|---|---|---|---|
| SEQ ID NO: | V$_H$ | SEQ ID NO: | V$_L$ |
| 119 | TSRLTINKDNSKNTV | 120 | GSGSGTDFTLTISRL |
| 121 | LTINKDNSKNTVYLQ | 122 | SGTDFTLTISRLEPE |
| 123 | NKDNSKNTVYLQMNS | 124 | DFTLTISRLEPEDFA |
| 125 | NSKNTVYLQMNSLRA | 126 | LTISRLEPEDFAVYY |
| 127 | NTVYLQMNSLRAEDT | 128 | SRLEPEDFAVYYCQQ |
| 129 | YLQMNSLRAEDTAVY | 130 | EPEDFAVYYCQQNNN |
| 131 | MNSLRAEDTAVYYCA | 132 | DFAVYYCQQNNNWPT |
| 133 | LRAEDTAVYYCARAL | 134 | VYYCQQNNNWPTTFG |
| 135 | EDTAVYYCARALTYY | 136 | CQQNNNWPTTFGQGT |
| 137 | AVYYCARALTYYDYE | 138 | NNNWPTTFGQGTKLE |
| 139 | YCARALTYYDYEFAY | 140 | NWPTTFGQGTKLEIK |
| 141 | RALTYYDYEFAYWGQ | 142 | DILLTQSPGTLSLSP |
| 143 | TYYDYEFAYWGQGTL | 144 | LTQSPGTLSLSPGER |
| 145 | DYEFAYWGQGTLVTV | 146 | SPGTLSLSPGERATL |
| 147 | EFAYWGQGTLVTVSS | 148 | TLSLSPGERATLSCR |

FIGURE 5-2

| SEQ ID NO: | Antibody Chain | CDR No. | Residue | Position in CDR | Kabat No. |
|---|---|---|---|---|---|
| 3 | Heavy | 1 | N | 1 | 31 |
| | | | Y | 2 | 32 |
| | | | G | 3 | 33 |
| | | | V | 4 | 34 |
| | | | H | 5 | 35 |
| 4 | Heavy | 2 | V | 1 | 50 |
| | | | I | 2 | 51 |
| | | | W | 3 | 52 |
| | | | S | 4 | 53 |
| | | | G | 5 | 54 |
| | | | G | 6 | 55 |
| | | | N | 7 | 56 |
| | | | T | 8 | 57 |
| | | | D | 9 | 58 |
| | | | Y | 10 | 59 |
| | | | N | 11 | 60 |
| | | | T | 12 | 61 |
| | | | P | 13 | 62 |
| | | | F | 14 | 63 |
| | | | T | 15 | 64 |
| | | | S | 16 | 65 |
| 5 | Heavy | 3 | A | 1 | 95 |
| | | | L | 2 | 96 |
| | | | T | 3 | 97 |
| | | | Y | 4 | 98 |
| | | | Y | 5 | 99 |
| | | | D | 6 | 100 |
| | | | Y | 7 | 100a |
| | | | E | 8 | 100b |
| | | | F | 9 | 100c |
| | | | A | 10 | 101 |
| | | | Y | 11 | 102 |

FIGURE 7

| SEQ ID NO: | Antibody Chain | CDR No. | Residue | Position in CDR | Kabat No. |
|---|---|---|---|---|---|
| 6 | Light | 1 | R | 1 | 24 |
|   |   |   | A | 2 | 25 |
|   |   |   | S | 3 | 26 |
|   |   |   | Q | 4 | 27 |
|   |   |   | S | 5 | 28 |
|   |   |   | I | 6 | 29 |
|   |   |   | G | 7 | 30 |
|   |   |   | T | 8 | 31 |
|   |   |   | N | 9 | 32 |
|   |   |   | I | 10 | 33 |
|   |   |   | H | 11 | 34 |
| 7 | Light | 2 | Y | 1 | 50 |
|   |   |   | A | 2 | 51 |
|   |   |   | S | 3 | 52 |
|   |   |   | E | 4 | 53 |
|   |   |   | S | 5 | 54 |
|   |   |   | I | 6 | 55 |
|   |   |   | S | 7 | 56 |
| 8 | Light | 3 | Q | 1 | 89 |
|   |   |   | Q | 2 | 90 |
|   |   |   | N | 3 | 91 |
|   |   |   | N | 4 | 92 |
|   |   |   | N | 5 | 93 |
|   |   |   | W | 6 | 94 |
|   |   |   | P | 7 | 95 |
|   |   |   | T | 8 | 96 |
|   |   |   | T | 9 | 97 |

FIGURE 8

| WT | Kabat No./ Position in CDR | Increased affinity heavy chain substitutions | |
|---|---|---|---|
| CDR-H1 ||||
| N | 31 / 1 | V | SEQ ID NO: 201 |
| Y | 32 / 2 | R | SEQ ID NO: 202 |
| V | 34 / 4 | L | SEQ ID NO: 203 |
|   |   | N | SEQ ID NO: 204 |
| CDR-H2 ||||
| V | 50 / 1 | L | SEQ ID NO: 205 |
|   |   | Q | SEQ ID NO: 206 |
| I | 51 / 2 | G | SEQ ID NO: 207 |
|   |   | M | SEQ ID NO: 208 |
|   |   | S | SEQ ID NO: 209 |
|   |   | Q | SEQ ID NO: 210 |
| W | 52 / 3 | G | SEQ ID NO: 211 |
|   |   | T | SEQ ID NO: 212 |
| S | 53 / 4 | Q | SEQ ID NO: 213 |
|   |   | T | SEQ ID NO: 214 |
| G | 55 / 6 | D | SEQ ID NO: 215 |
| N | 56 / 7 | G | SEQ ID NO: 216 |
| T | 57 / 8 | A | SEQ ID NO: 217 |
|   |   | D | SEQ ID NO: 218 |
|   |   | G | SEQ ID NO: 219 |
|   |   | S | SEQ ID NO: 220 |
| Y | 59 / 10 | A | SEQ ID NO: 221 |
|   |   | C | SEQ ID NO: 222 |
|   |   | E | SEQ ID NO: 223 |
|   |   | F | SEQ ID NO: 224 |
|   |   | G | SEQ ID NO: 225 |
|   |   | S | SEQ ID NO: 226 |
|   |   | W | SEQ ID NO: 227 |
| N | 60 / 11 | D | SEQ ID NO: 228 |
| T | 64 / 15 | E | SEQ ID NO: 229 |
| CDR-H3 ||||
| Y | 98 / 4 | W | SEQ ID NO: 312 |

FIGURE 9

| WT | Kabat No./ Position in CDR | Increased affinity light chain substitutions | |
|---|---|---|---|
| CDR-L1 | | | |
| A | 25 / 2 | V | SEQ ID NO: 313 |
|   |        | S | SEQ ID NO: 314 |
| G | 30 / 7 | Y | SEQ ID NO: 315 |
| CDR-L3 | | | |
| N | 91 / 3 | L | SEQ ID NO: 316 |
| N | 92 / 4 | L | SEQ ID NO: 317 |
|   |        | R | SEQ ID NO: 318 |
| T | 97 / 9 | A | SEQ ID NO: 319 |
|   |        | D | SEQ ID NO: 320 |
|   |        | E | SEQ ID NO: 321 |

FIGURE 10

| WT | Kabat No./ Position in CDR | Increased affinity heavy chain substitutions | |
|---|---|---|---|
| CDR-H2 | | | |
| Y | 59 / 10 | H | SEQ ID NO: 322 |

FIGURE 11

| WT | Kabat No./ Position in CDR | Increased affinity light chain substitutions | |
|---|---|---|---|
| CDR-L1 | | | |
| R | 24 / 1 | P | SEQ ID NO: 323 |
| A | 25 / 2 | C | SEQ ID NO: 324 |
| | | F | SEQ ID NO: 325 |
| | | M | SEQ ID NO: 326 |
| | | L | SEQ ID NO: 327 |
| Q | 27 / 4 | W | SEQ ID NO: 328 |
| S | 28 / 5 | R | SEQ ID NO: 329 |
| G | 30 / 7 | W | SEQ ID NO: 330 |
| | | F | SEQ ID NO: 331 |
| | | T | SEQ ID NO: 332 |
| | | M | SEQ ID NO: 333 |
| | | S | SEQ ID NO: 334 |
| T | 31 / 8 | V | SEQ ID NO: 335 |
| | | E | SEQ ID NO: 336 |
| N | 32 / 9 | H | SEQ ID NO: 337 |
| CDR-L3 | | | |
| T | 97 / 9 | I | SEQ ID NO: 338 |
| | | G | SEQ ID NO: 339 |
| | | L | SEQ ID NO: 340 |
| | | H | SEQ ID NO: 341 |
| | | R | SEQ ID NO: 342 |

FIGURE 12

| WT | Kabat No./ Position in CDR | Increased affinity heavy chain substitutions | |
|---|---|---|---|
| CDR-H1 | | | |
| N | 31 / 1 | D | SEQ ID NO: 343 |
|   |        | I | SEQ ID NO: 344 |
|   |        | T | SEQ ID NO: 345 |
| V | 34 / 4 | E | SEQ ID NO: 346 |
|   |        | Q | SEQ ID NO: 347 |
| CDR-H2 | | | |
| V | 50 / 1 | E | SEQ ID NO: 348 |
|   |        | I | SEQ ID NO: 349 |
| I | 51 / 2 | A | SEQ ID NO: 350 |
|   |        | C | SEQ ID NO: 351 |
| S | 53 / 4 | N | SEQ ID NO: 352 |
| G | 55 / 6 | A | SEQ ID NO: 353 |
|   |        | E | SEQ ID NO: 354 |
|   |        | H | SEQ ID NO: 355 |
| T | 57 / 8 | E | SEQ ID NO: 356 |
| Y | 59 / 10 | P | SEQ ID NO: 357 |
|   |         | Q | SEQ ID NO: 358 |

FIGURE 13

| WT | Kabat No./ Position in CDR | Increased affinity light chain substitutions | |
|---|---|---|---|
| CDR-L1 | | | |
| A | 25 / 2 | I | SEQ ID NO: 359 |
|   |        | P | SEQ ID NO: 360 |
|   |        | T | SEQ ID NO: 361 |
|   |        | Y | SEQ ID NO: 362 |
| G | 30 / 7 | C | SEQ ID NO: 363 |
|   |        | H | SEQ ID NO: 364 |
|   |        | K | SEQ ID NO: 365 |
|   |        | Q | SEQ ID NO: 366 |
|   |        | R | SEQ ID NO: 367 |
| CDR-L3 | | | |
| N | 92 / 4 | K | SEQ ID NO: 368 |
|   |        | M | SEQ ID NO: 369 |
| T | 97 / 9 | C | SEQ ID NO: 370 |
|   |        | K | SEQ ID NO: 371 |
|   |        | N | SEQ ID NO: 372 |
|   |        | Q | SEQ ID NO: 373 |

FIGURE 14

| WT | Kabat No./ Position in CDR | Neutral heavy chain substitutions | |
|---|---|---|---|
| | | CDR-H1 | |
| V | 34 / 4 | S | SEQ ID NO: 374 |
| | | CDR-H2 | |
| I | 51 / 2 | V | SEQ ID NO: 375 |
| G | 55 / 6 | F | SEQ ID NO: 376 |
| N | 56 / 7 | S | SEQ ID NO: 377 |
| N | 60 / 11 | A | SEQ ID NO: 378 |
| | | CDR-H3 | |
| Y | 102 / 11 | F | SEQ ID NO: 379 |

FIGURE 15

| WT | Kabat No./ Position in CDR | Neutral light chain substitutions | |
|---|---|---|---|
| | | CDR-L1 | |
| A | 25 / 2 | W | SEQ ID NO: 380 |
| Q | 27 / 4 | T | SEQ ID NO: 381 |
| S | 28 / 5 | F | SEQ ID NO: 382 |
| G | 30 / 7 | A | SEQ ID NO: 383 |
| T | 31 / 8 | R | SEQ ID NO: 384 |
| | | CDR-L2 | |
| S | 54 / 5 | V | SEQ ID NO: 385 |
| | | CDR-L3 | |
| N | 93 / 5 | V | SEQ ID NO: 386 |
| T | 97 / 9 | R | SEQ ID NO: 387 |

| SEQ ID NO: | CDR-VH1 31 | 32 | 33 | 34 | 35 | SEQ ID NO: | CDR-VH2 50 | 51 | 52 | 53 | 54 | 55 | 56 | 57 | 58 | 59 | 60 | 61 | 62 | 63 | 64 | 65 | SEQ ID NO: | CDR-VH3 95 | 96 | 97 | 98 | 99 | 100 | 100a | 100b | 100c | 101 | 102 |
|---|---|---|---|---|---|---|---|---|---|---|---|---|---|---|---|---|---|---|---|---|---|---|---|---|---|---|---|---|---|---|---|---|---|---|
| 3 | N | Y | G | V | H | 4 | V | I | W | S | G | G | N | T | D | Y | N | T | P | F | T | S | 5 | A | L | T | Y | Y | D | Y | E | F | A | Y |
| 3 | | | | | | 158 | | | | | | | A | | | | | | | S | | K | | 5 | | | | | | | | | | | |
| 3 | | | | | | 159 | | | | | | | | | | | | | | | L | | | 5 | | | | | | | | | | | |
| 3 | | | | | | 160 | | | | | | | | | | | | | | S | L | K | G | 5 | | | | | | | | | | | |
| 3 | | | | | | 161 | | | | | | | | | | | | | | | V | | | 5 | | | | | | | | | | | |
| 3 | | | | | | 4 | | | | | | | | | | | | | | | | | | 176 | | | D | | | | | N | | | |
| 3 | | | | | | 4 | | | | | | | | | | | | | | | | | | 177 | | | D | | | | | D | | | |
| 3 | | | | | | 4 | | | | | | | | | | | | | | | | | | 178 | | | D | | | | | D | D | | |
| 3 | | | | | | 4 | | | | | | | | | | | | | | | | | | 179 | | | D | | | | | | Y | | |
| 149 | | | | W | S | 162 | Y | | | | | | | | Y | | | | | | | | | 5 | | | | | | | | | | | |
| 3 | | | | | | 158 | | | | | | | A | | | | | P | S | L | K | | | 180 | | | D | | | | | D | Y | | |
| 3 | | | | | | 163 | | | | | | | S | D | | | | | | | | | | 180 | | | D | | | | | D | Y | | |
| 3 | | | | | | 164 | | | | | | | | P | | | | | | | | A | | 180 | | | D | | | | | D | Y | | |
| 3 | | | | | | 165 | | | | | | | T | P | | | | | | | | | | 179 | | | D | | | | | D | Y | | |
| 3 | | | | | | 166 | | | | | | | T | P | | | | | | | | | | 179 | | | D | | | | | D | Y | | |
| 3 | | | | | | 167 | | | | | | | T | P | | | | | | | | | | 177 | | | D | | | | | N | | | |
| 3 | | | | | | 167 | | | | | | | T | P | | | | | | | | | | 179 | | | D | | | | | D | Y | | |
| 150 | W | | D | | | 4 | N | | | | | | | | | | | | | | | | | 176 | | | D | | | | | | | | |
| 150 | W | | E | | | 4 | N | | | | | | | | | | | | | | | | | 180 | | | D | | | | | D | Y | | |
| 151 | W | | A | | | 4 | N | | | | | | | | | | | | | | | | | 180 | | | D | | | | | D | Y | | |
| 152 | W | | A | | | 4 | N | | | | | | | | | | | | | | | | | 180 | | | D | | | | | D | Y | | |
| 153 | W | | D | | | 4 | | | | | | | | | | | | | | | | | | 176 | | | D | | | | | N | | | |
| 154 | W | | D | | | 4 | | | | | | | | | | | | | | | | | | 180 | | | D | | | | | D | Y | | |
| 155 | W | | D | | | 4 | | | | | | | | | | | | | | | | | | 176 | | | D | | | | | N | | | |
| 156 | W | | D | | | 4 | | | | | | | | | | | | | | | | | | 179 | | | D | | | | | | Z | | |
| 150 | W | | D | | | 168 | | | | | | | A | | | | | | | | | A | | 180 | | | D | | | | | D | | | |

FIGURE 17-2

CDR-VH1, CDR-VH2, CDR-VH3 variant table

| SEQ ID NO: | CDR-VH1 |  |  |  |  | SEQ ID NO: | CDR-VH2 |  |  |  |  |  |  |  |  |  |  |  |  |  |  | SEQ ID NO: | CDR-VH3 |  |  |  |  |  |  |  |  |  |  |
|---|---|---|---|---|---|---|---|---|---|---|---|---|---|---|---|---|---|---|---|---|---|---|---|---|---|---|---|---|---|---|---|---|---|---|
|  | 31 | 32 | 33 | 34 | 35 |  | 50 | 51 | 52 | 53 | 54 | 55 | 56 | 57 | 58 | 59 | 60 | 61 | 62 | 63 | 64 | 65 |  | 95 | 96 | 97 | 98 | 99 | 100 | 100a | 100b | 100c | 101 | 102 |
|  | N | Y | G | V | H |  | V | I | W | S | G | G | N | T | D | Y | N | T | P | F | T | S |  | A | L | T | Y | Y | D | Y | E | F | A | Y |
| 3 |   |   |   |   |   | 4 |   |   |   |   |   |   |   |   |   |   |   |   |   |   |   |   | 5 |   |   |   |   |   |   |   |   |   |   |   |
| 150 |   | W |   |   |   | 168 |   |   |   |   |   |   |   |   |   |   |   |   |   |   |   |   | 180 |   |   | D |   |   |   |   |   |   |   |   |
| 150 |   | W |   |   |   | 164 |   |   |   |   |   |   | A |   |   |   |   |   |   |   |   |   | 177 |   |   | D |   |   |   |   | D |   |   |   |
| 156 |   | W | E |   |   | 158 |   |   |   |   |   |   |   | D |   |   |   |   |   |   |   |   | 177 |   |   | D |   |   |   |   | D |   |   |   |
| 154 |   | W | A |   |   | 158 |   |   |   |   |   |   | A |   |   |   |   |   |   |   |   |   | 177 |   |   | D |   |   |   |   | D |   |   |   |
| 155 |   | W | D |   |   | 169 |   |   |   |   |   |   | A |   |   |   |   |   |   |   | A |   | 176 |   |   | D |   |   |   |   | N |   |   |   |
| 155 |   | W | D |   |   | 170 |   |   |   |   |   |   |   |   |   |   |   |   |   |   | A |   | 176 |   |   | D |   |   |   |   | N |   |   |   |
| 150 |   | W |   |   |   | 158 | N |   |   |   |   |   | A |   |   |   |   |   |   |   |   |   | 178 |   |   | D |   |   |   |   |   |   |   |   |
| 150 |   | W |   |   |   | 166 |   |   |   |   |   |   | A |   |   |   |   |   |   |   |   |   | 177 |   |   | D |   |   |   |   | D |   |   |   |
| 150 |   | W |   |   |   | 171 |   |   |   |   |   |   | T | P |   |   |   |   |   |   |   |   | 177 |   |   | D |   |   |   |   | D |   |   |   |
| 155 |   | W | D |   |   | 167 |   |   |   |   |   |   | T | P |   |   |   |   |   |   |   |   | 177 |   |   | D |   |   |   |   | D |   |   |   |
| 155 |   | W | D |   |   | 158 | N |   |   |   |   |   | A |   |   |   |   |   |   |   |   |   | 177 |   |   | D |   |   |   |   | D |   |   |   |
| 155 |   | W | D |   |   | 165 | N |   |   |   |   |   |   | P |   |   |   |   |   |   | A |   | 177 |   |   | D |   |   |   |   | D | D |   |   |
| 155 |   | W | D |   |   | 172 | N |   |   |   |   |   | A |   |   |   |   |   |   |   | T |   | 179 |   |   | D |   |   |   |   | D |   |   |   |
| 155 |   | W | D |   |   | 171 | N |   |   |   |   |   | T |   |   |   |   |   |   |   |   |   | 177 |   |   | D |   |   |   |   | D |   |   |   |
| 155 |   | W | D |   |   | 165 |   |   |   |   |   |   | A | P |   |   |   |   |   |   |   |   | 177 |   |   | D |   |   |   |   | D |   |   |   |
| 155 |   | W | D |   |   | 173 |   |   |   |   |   |   | A |   |   |   |   |   |   |   |   |   | 177 |   |   |   |   |   |   |   | D | Y |   |   |
| 157 |   | W |   |   |   | 158 |   |   |   |   |   |   | A |   |   |   |   |   |   |   |   |   | 177 |   |   |   |   |   |   |   | D |   |   |   |
| 3 |   |   |   |   |   | 174 |   |   |   |   |   |   |   |   |   |   |   | E |   |   |   |   | 5 |   |   |   |   |   |   |   |   |   |   |   |
| 3 |   |   |   |   |   | 175 |   |   |   |   |   |   |   |   |   |   |   | E |   |   |   |   | 5 |   |   |   |   |   |   |   |   |   |   |   |
| 3 |   |   |   |   |   |   |   |   |   |   |   |   |   |   |   |   |   |   |   |   |   |   | 5 |   |   |   |   |   |   |   |   |   |   |   |

FIGURE 18

| SEQ ID NO | 24 R | 25 A | 26 S | 27 Q | 28 S | 29 I | 30 G | 31 T | 32 N | 33 I | 34 H | SEQ ID NO | 50 Y | 51 A | 52 S | 53 E | 54 S | 55 I | 56 S | SEQ ID NO | 89 Q | 90 Q | 91 N | 92 N | 93 N | 94 W | 95 P | 96 T | 97 T |
|---|---|---|---|---|---|---|---|---|---|---|---|---|---|---|---|---|---|---|---|---|---|---|---|---|---|---|---|---|---|
| 6 | | | | | | | | | | | | 7 | | | | | | | | 8 | | | | | | | | L | |
| 6 | | | | | | | | | | | | 7 | | | | | | | | 189 | | | | | | | | | S |
| 6 | | | | | | | | | | | | 7 | | | | | | | | 190 | | | | | D | | | | S |
| 6 | | | | | | | | | | | | 7 | | | | | | | | 191 | | | | | E | | | | S |
| 6 | | | | E | | | | | | | | 7 | | | | | | | | 192 | | | | | D | | | | S |
| 6 | | | | E | | | | | | | | 7 | | | | | | | | 193 | | | | | E | | | | S |
| 181 | | | | E | | | | | | | | 7 | | | | | | | | 194 | | | | | | | | | S |
| 181 | | | | F | | | | | | | | 7 | | | | | | | | 192 | | | | | K | | | | S |
| 181 | | | | Y | | | | | | | | 7 | | | | | | | | 195 | | | | | E | | | | S |
| 182 | | | | Y | | | | | | | | 7 | | | | | | | | 194 | | | | | | | | | |
| 183 | | | | Y | | | | | | | | 7 | | | | | | | | 192 | | | | | E | | | | |
| 183 | | | | Y | | | | | | | | 7 | | | | | | | | 192 | | | | | D | | | | |
| 183 | | | | H | | | | | | | | 7 | | | | | | | | 194 | | | | | E | | | | |
| 183 | | | | H | | | | | | | | 7 | | | | | | | | 190 | | | | | D | | | | |
| 184 | | | | | | | | | | | | 7 | | | | | | | | 191 | | | | | | | | | |
| 184 | | | | | | | | | | L | | 7 | | | | | | | | 190 | H | | | | | | | | |
| 185 | | | | | | | | | | | | 7 | | | | | | | | 192 | | | | | | | | | S |
| 186 | | | D | | | | | | | | | 7 | | | | | | | | 196 | | | | | | | | | |
| 187 | | | | | | | | E | | | | 7 | | | | | | | | 8 | | | | | A | | | | |
| 6 | | | | | | | | | | | | 7 | | | | | | | | 8 | | | | | A | | | | |
| 187 | | | | | | | | E | | | | 7 | | | | | | | | 197 | | | | | A | | | | |
| 188 | | | D | | | | | E | | | | 7 | | | | | | | | 197 | | | | | | | | | |

FIGURE 19

| SEQ ID NO: | CDR-VH3 | | | | | | | | | | | | SEQ ID NO: | CDR-VL1 | | | | | | | | | | |
|---|---|---|---|---|---|---|---|---|---|---|---|---|---|---|---|---|---|---|---|---|---|---|---|---|---|
| | 95 | 96 | 97 | 98 | 99 | 100 | 100a | 100b | 100c | 101 | 102 | | 24 | 25 | 26 | 27 | 28 | 29 | 30 | 31 | 32 | 33 | 34 |
| 5 | A | L | T | Y | Y | D | Y | E | F | A | Y | 6 | R | A | S | Q | S | I | G | T | N | I | H |
| 198 | | | | | | C | | | | | | 200 | | | | | | | | | | | |
| 199 | | | | | | | | | | C | | 6 | | | | | | | | | | | C |

| WT residue | Substitution | Kabat No. / Position in CDR | Fold increase over WT by FACS | Fold increase over WT by ELISA | Fold increase over WT by AlphaLISA | Fold increase over WT by BIAcore |
|---|---|---|---|---|---|---|
| CDR-H1 | | | | | | |
| N | V (SEQ ID NO: 201) | 31 / 1 | 3.6 | 2 | 2.2 | 2 |
| Y | R (SEQ ID NO: 202) | 32 / 2 | 3.6 | 1.8 | 4.3 | - |
| G | D (SEQ ID NO: 151) | 33 / 3 | 11.1 | - | - | - |
| G | A (SEQ ID NO: 153) | 33 / 3 | 5.5 | - | - | - |
| V | N (SEQ ID NO: 204) | 34 / 4 | 4.2 | - | - | - |
| V | L (SEQ ID NO: 203) | 34 / 4 | 3.5 | - | - | - |
| CDR-H2 | | | | | | |
| V | L (SEQ ID NO: 205) | 50 / 1 | 7.6 | 1.9 | 3.8 | - |
| V | Q (SEQ ID NO: 206) | 50 / 1 | 7.0 | - | - | - |
| I | G (SEQ ID NO: 207) | 51 / 2 | 6.4 | - | 4.6 | - |
| I | Q (SEQ ID NO: 210) | 51 / 2 | 3.4 | - | - | - |
| I | M (SEQ ID NO: 208) | 51 / 2 | 3.5 | - | - | - |
| I | S (SEQ ID NO: 209) | 51 / 2 | 2.6 | - | - | - |
| W | G (SEQ ID NO: 211) | 52 / 3 | 5.0 | 1.5 | 1.8 | - |
| W | T (SEQ ID NO: 212) | 52 / 3 | 4.0 | - | - | - |
| S | Q (SEQ ID NO: 213) | 53 / 4 | 4.0 | 1.4 | 1.1 | - |
| S | T (SEQ ID NO: 214) | 53 / 4 | 3.1 | - | - | - |
| G | D (SEQ ID NO: 215) | 55 / 6 | 5.5 | 1.6 | 2 | - |
| N | G (SEQ ID NO: 216) | 56 / 7 | 5.2 | - | - | - |
| T | P (SEQ ID NO: 173) | 57 / 8 | 6.6 | - | - | - |
| T | G (SEQ ID NO: 219) | 57 / 8 | 4.8 | 1.8 | 3.8 | - |
| T | D (SEQ ID NO: 218) | 57 / 8 | 2.3 | - | - | - |
| T | S (SEQ ID NO: 220) | 57 / 8 | 2.1 | - | - | - |
| T | A (SEQ ID NO: 217) | 57 / 8 | 1.9 | - | - | - |
| Y | E (SEQ ID NO: 223) | 59 / 10 | 4.3 | 1.9 | 1.4 | 2.3 |
| Y | S (SEQ ID NO: 226) | 59 / 10 | 3.6 | - | - | - |
| Y | W (SEQ ID NO: 227) | 59 / 10 | 2.6 | - | - | - |
| Y | A (SEQ ID NO: 221) | 59 / 10 | 2.3 | - | - | - |
| Y | F (SEQ ID NO: 224) | 59 / 10 | 2.1 | - | - | - |
| Y | C (SEQ ID NO: 222) | 59 / 10 | 2.2 | - | - | - |
| Y | G (SEQ ID NO: 225) | 59 / 10 | 1.9 | - | - | - |
| N | D (SEQ ID NO: 228) | 60 / 11 | 3.0 | - | - | - |
| F | V (SEQ ID NO: 292) | 63 / 14 | 1.9 | - | - | - |
| T | E (SEQ ID NO: 229) | 64 / 15 | 1.9 | - | - | - |
| CDR-H3 | | | | | | |
| T | D (SEQ ID NO: 301) | 97 / 3 | 13.0 | - | - | - |
| Y | W (SEQ ID NO: 230) | 98 / 4 | 1.9 | 2.1 | 3.7 | 1.8 |
| F | Y (SEQ ID NO: 293) | 100c / 9 | 3.2 | - | - | - |

FIGURE 20-1

| WT residue | Substitution | Kabat No. / Position in CDR | Fold increase over WT by FACS | Fold increase over WT by ELISA | Fold increase over WT by AlphaLISA | Fold increase over WT by BIAcore |
|---|---|---|---|---|---|---|
| CDR-L1 | | | | | | |
| A | V (SEQ ID NO: 231) | 25 / 2 | 4.5 | 1.9 | 3.0 | - |
| A | S (SEQ ID NO: 232) | 25 / 2 | 2.3 | - | - | - |
| Q | Y (SEQ ID NO: 304) | 27 / 4 | 2.7 | - | - | - |
| G | Y (SEQ ID NO: 233) | 30 / 7 | 7.5 | 3.9 | 4.8 | 4.8 |
| CDR-L3 | | | | | | |
| N | L (SEQ ID NO: 234) | 91 / 3 | 2.3 | 1.6 | 2.0 | - |
| N | L (SEQ ID NO: 235) | 92 / 4 | 3.0 | 1.7 | 2.2 | - |
| N | R (SEQ ID NO: 236) | 92 / 4 | 3.1 | - | - | - |
| N | E (SEQ ID NO: 309) | 93 / 5 | 2.6 | - | - | - |
| N | A (SEQ ID NO: 310) | 93 / 5 | 2.4 | - | - | - |
| T | A (SEQ ID NO: 237) | 97 / 9 | 2.4 | - | - | - |
| T | S (SEQ ID NO: 311) | 97 / 9 | 6.6 | - | - | - |
| T | D (SEQ ID NO: 238) | 97 / 9 | 5.0 | - | - | - |
| T | E (SEQ ID NO: 239) | 97 / 9 | 3.5 | - | - | - |

FIGURE 20-2

| Combo Variant | WT | Kabat No. / Position in CDR | | Substitution | Fold increase over WT by ELISA | Fold increase over WT by AlphaLISA | Fold increase over WT by KinExA |
|---|---|---|---|---|---|---|---|
| Combo 1 | I | 51/2 | VH | G (SEQ ID NO: 207) | 18.7 | 7.0 | 24.0 |
| | Y | 98/4 | | W (SEQ ID NO: 230) | | | |
| | G | 30/7 | VL | Y (SEQ ID NO: 233) | | | |
| | N | 92/4 | | L (SEQ ID NO: 235) | | | |
| Combo 2 | N | 31/1 | VH | V (SEQ ID NO: 201) | 3.4 | 3.0 | - |
| | V | 50/1 | | L (SEQ ID NO: 205) | | | |
| | A | 25/2 | VL | V (SEQ ID NO: 231) | | | |
| | N | 91/3 | | L (SEQ ID NO: 234) | | | |

ANTI-EGFR ANTIBODIES AND THEIR USES

I. CROSS REFERENCE TO RELATED APPLICATIONS

This application claims the benefit under 35 U.S.C. §119 (e) of U.S. Provisional Application No. 61/255,632, filed Oct. 28, 2009, the contents of which are incorporated herein by reference in their entireties.

1.1 SEQUENCE LISTING

The instant application contains a Sequence Listing, which has been submitted in ASCII format via EFS-Web and is hereby incorporated by reference in its entirety. Said ASCII copy, created on Oct. 26, 2010, is named 38149322.txt and is 113,333 bytes in size.

2. FIELD OF THE INVENTION

The present invention relates to anti-EGFR antibodies, pharmaceutical compositions comprising anti-EGFR antibodies, and therapeutic uses of such antibodies.

3. BACKGROUND

Monoclonal antibody therapy has provided an opportunity to target and destroy tumors using antibodies engineered against tumor-specific antigens. In general, monoclonal antibody therapy stimulates a patient's immune system to attack malignant tumor cells or prevents tumor growth by blocking or inhibiting specific cell receptors. Treatment requires identification of a tumor-specific antigen on a cell-surface molecule. Representative cell-surface molecules targeted in clinical trials include those originating from various lymphomas/leukemias (such as T-cell and/or B-cell lymphomas/leukemias) and solid tumors (such as epithelial tumors of the breast, colon, and lung). Promising results have been reported in the treatment of metastatic colorectal cancer and head and neck cancer with humanized monoclonal antibodies, particularly treatments targeting epidermal growth factor receptor (EGFR, EGF receptor), a signaling protein that normally controls cell division.

EGFR (also known as ErbB-1 and HER1 in humans) is the cell-surface receptor for members of the epidermal growth factor family (EGF-family) of extracellular protein ligands (Herbst, 2004, Int. J. Radiat. Oncol. Biol. Phys. 59 (2 Suppl): 21-6). The epidermal growth factor receptor is a member of the ErbB family of receptors, a subfamily of four closely related proteins: EGFR (ErbB-1), HER2/neu (ErbB-2), HER3 (ErbB-3) and HER4 (ErbB-4). Mutations affecting EGFR expression or activity can result in cancer. In point of fact, EGF receptors are overexpressed in most epithelial malignancies including those of the colon and the rectum. The EGFR is constitutively expressed in many normal epithelial tissues, including the skin and hair follicle.

The development of a monoclonal antibody therapy based on the discovery of the role of EGF receptors in the etiology of certain cancers first involved the development of a murine-based antibody. Immunization of mice with human A431 epidermoid carcinoma cells expressing high levels of EGFR resulted in antibodies that bound specifically to the extracellular portion of EGFR (El-Gewely, 2006, Biotechnology Annual Review (Amsterdam, Elsevier) at page 177). The monoclonal antibody, known as MAb225, bound specifically to the human EGFR with an affinity equal to its ligand, competed with ligand binding, and blocked the activation of the receptor tyrosine kinase (Goldstein et al., 1995, Clin. Cancer Res. 1:1311-1318).

Murine antibodies have the potential to generate an unwanted immunogenic response in patients. Murine antibody 225 was therefore chimerized with human IgG1 to produce a recombinant, human/mouse chimeric monoclonal antibody known as C225 having constant regions of human IgG1κ origin and variable murine regions that bind specifically to the extracellular domain of the human epidermal growth factor receptor (EGFR). C225 is believed to work mainly by blocking the EGF binding to EGFR, thereby "starving" the tumor of needed growth factor. C225 also binds specifically to EGFR on normal cells, and competitively inhibits the binding of EGF and other ligands, such as transforming growth factor—alpha. Binding results in the blocking of phosphorylation and activation of receptor-associated kinases, resulting in inhibition of cell growth, induction of apoptosis, and decreased matrix metalloproteinase and vascular endothelial growth factor (VEGF) production.

C225 is commercially known as Erbitux® (cetuximab) and is marketed by ImClone and Bristol-Myers Squibb in the United States, and elsewhere by Merck KgaA. Erbitux® was approved by the FDA in March 2006 for use in combination with radiation therapy for treating squamous cell carcinoma of the head and neck (SCCHN) or as a single agent in patients who have had prior platinum-based therapy. Erbitux® is also indicated for treatment of metastatic colon cancer in combination with irinotecan (Camptosar®), a DNA topoisomerase blocker.

Kirsten rat sarcoma viral oncogene homolog (KRAS) mutation status has recently been shown to be predictive of response to cetuximab therapy in colorectal cancer (Van Cutsem et al., 2008, J. Clin. Oncol 26 (May 20 suppl): Abstract 2). KRAS is a GTPase with a role in a number of signal transduction pathways. Mutations in the gene which encodes KRAS, present in over 25% of colorectal cancers, is predictive of the success of EGFR-inhibiting drugs. Expression of the mutated KRAS gene results in a diminished response to EGFR-inhibitor therapy. KRAS mutations can be detected by commercially available laboratory diagnostics.

Erbitux® elicits an immune response in about 5% of patients. Such an immune response can result in an immune complex-mediated clearance of the antibodies or fragments from the circulation, and make repeated administration unsuitable for therapy, thereby reducing the therapeutic benefit to the patient and limiting the re-administration of the antibody. Further, Erbitux® antibody causes an acneform rash in 90% of patients, with debilitating rashes found in as many as 10% of drug recipients. Other significant side effects include mucosal surface problems, malaise, nausea, fever, gastrointestinal problems, and headache (Chabner et al., 2008, Harrison's Manual of Oncology (New York: McGraw-Hill Medical), at pages 117-118). Finally, additional problems associated with the use of tumor-specific or tumor-selective monoclonal antibodies such as Erbitux® as therapeutic agents include antigenic variation of the tumor, inefficient killing of cells after binding the monoclonal antibody, inefficient penetration of the antibody into the tumor mass, and soluble target antigens mopping up the antibody.

Accordingly, there is a need to provide improved monoclonal antibodies which interfere with EGFR receptor signaling that overcome one or more of these problems, for example, by generating variants with higher affinity than Erbitux® that can be administered at reduced dosages (and thus whose administration results in reduced immunogenicity as compared to Erbitux®), or variants with reduced immunogenicity and other side-effects as compared to Erbitux®.

Citation or identification of any reference in Section 3 or in any other section of this application shall not be construed as an admission that such reference is available as prior art to the present disclosure.

4. SUMMARY

The present disclosure relates to anti-EGFR antibodies and anti-EGFR binding fragments.

The anti-EGFR antibodies and binding fragments of the disclosure have one, two, or three of the following characteristics:

(1) the anti-EGFR antibodies and binding fragments have CDRs that are related in sequence to the CDRs of an antibody having a heavy chain ($V_H$) having a sequence corresponding to SEQ ID NO:9 and a light chain ($V_L$) having a sequence corresponding to SEQ ID NO:10, said CDRs corresponding to SEQ ID NOs.:3, 4, 5, 6, 7 and 8, respectively, for example, CDRs that have overall at least 70%, at least 75%, at least 80%, at least 85%, at least 90%, at least 91%, at least 92%, at least 93%, at least 94%, at least 95%, at least 96%, at least 97%, or at least 98% sequence identity to the CDRs of said antibody having a $V_H$ with an amino acid sequence corresponding to SEQ ID NO:9 and a $V_L$ with an amino acid sequence corresponding to SEQ ID NO:10, for example, they have CDRs with up to 10, up to 9, up to 8, up to 7, up to 6, up to 5, up to 4, up to 3, or up to 2 amino acid substitutions in the six CDRs as compared to CDRs corresponding to SEQ ID NOs.:3, 4, 5, 6, 7 and 8;

(2) the anti-EGFR antibodies and binding fragments have CDRs that are related in sequence to the CDRs of an antibody having a heavy chain ($V_H$) having a sequence corresponding to SEQ ID NO:1 and a light chain ($V_L$) having a sequence corresponding to SEQ ID NO:2, said CDRs corresponding to SEQ ID NOs.:3, 4, 5, 6, 7 and 8, respectively, for example, CDRs that have overall at least 70%, at least 75%, at least 80%, at least 85%, at least 90%, at least 91%, at least 92%, at least 93%, at least 94%, at least 95%, at least 96%, at least 97%, or at least 98% sequence identity to the CDRs of said antibody having a $V_H$ with an amino acid sequence corresponding to SEQ ID NO:1 and a $V_L$ with an amino acid sequence corresponding to SEQ ID NO:2, for example, they have CDRs with up to 10, up to 9, up to 8, up to 7, up to 6, up to 5, up to 4, up to 3, or up to 2 amino acid substitutions in the six CDRs as compared to CDRs corresponding to SEQ ID NOs.:3, 4, 5, 6, 7 and 8;

(3) the anti-EGFR antibodies and binding fragments have CDRs that are related in sequence to CDRs having one of the substitutions identified in FIGS. 20-1 and 20-2 and/or having the combination of substitutions identified in FIG. 20-3 as compared to CDRs corresponding to SEQ ID NOs.:3, 4, 5, 6, 7 and 8, respectively, for example, a CDR-L1 having the substitution G30Y, such CDRs having, for example, overall at least 70%, at least 75%, at least 80%, at least 85%, at least 90%, at least 91%, 92%, at least 93%, at least 94%, at least 95%, at least 96%, at least 97%, or at least 98% sequence identity to the CDRs having one of the substitutions identified in FIGS. 20-1 and 20-2 and/or having the combination of substitutions identified in FIG. 20-3 as compared to CDRs corresponding to SEQ ID NOs.:3, 4, 5, 6, 7 and 8, said CDRs optionally including said one or more substitutions identified in FIGS. 20-1 and 20-2 and/or the combination of substitutions identified in FIG. 20-3;

(4) the anti-EGFR antibodies and binding fragments have CDRs that differ in sequence by at least one amino acid and up to 17, up to 16, up to 15, up to 14, up to 13, up to 12, up to 11, up to 10, up to 9, up to 8, up to 7, up to 6, up to 5, up to 4, up to 3 amino acids as compared to CDRs corresponding to SEQ ID NOs.:3, 4, 5, 6, 7 and 8;

(5) the anti-EGFR antibodies and binding fragments have improved affinity towards EGFR as compared to an antibody having the CDRs of an antibody with a $V_H$ with an amino acid sequence corresponding to SEQ ID NO:9 and a $V_L$ with an amino acid sequence corresponding to SEQ ID NO:10 and/or as compared to an antibody having the CDRs of an antibody with a $V_H$ with an amino acid sequence corresponding to SEQ ID NO:9 and a $V_L$ with an amino acid sequence corresponding to SEQ ID NO:10;

(6) the anti-EGFR antibodies and binding fragments have reduced immunogenicity as compared to an antibody having a $V_H$ with an amino acid sequence corresponding to SEQ ID NO:1 and a $V_L$ with an amino acid sequence corresponding to SEQ ID NO:2.

The antibodies of the disclosure can have at least one (and optionally more) features from characteristics (1), (2), (3) and (4) above, and optionally further have at least one (and optionally more) feature from characteristics (5) and (6).

Antibodies of the disclosure can result in reduced immunogenic reactions (e.g., T-cell and/or Human Anti-Mouse Antibody (HAMA)) responses when used therapeutically, either because they are inherently less immunogenic or because they have improved binding affinity so lower doses are needed. In addition, therapeutic efficacy is increased, either because binding affinity is improved or because immunogenicity is reduced such that larger doses, or more repeated doses, can safely be administered.

Generally, the antibodies of the disclosure relate in structural and/or functional characteristics to cetuximab, which comprises a heavy chain ($V_H$) having a sequence corresponding to SEQ ID NO:1, a light chain ($V_L$) corresponding to SEQ ID NO:2, three heavy chain complementarity determining regions (CDRs), referred to herein (in amino- to carboxy-terminal order) as CDR-H1 (SEQ ID NO:3), CDR-H2 (SEQ ID NO:4) and CDR-H3 (SEQ ID NO:5), and three light chain CDRs referred to herein (in amino- to carboxy-terminal order) as CDR-L1 (SEQ ID NO:6), CDR-L2 (SEQ ID NO:7) and CDR-L3 (SEQ ID NO:8). The sequences of the cetuximab CDRs are shown in FIGS. 1A and 1C, and their numbering is set forth in FIG. 7 (for heavy chain CDRs) and FIG. 8 (for light chain CDRs). Cetuximab is a chimeric antibody, whose parental murine antibody is referred to as "MAb225", and contains immunogenic epitopes.

The anti-EGFR antibodies and anti-EGFR binding fragments of the disclosure can comprise a $V_H$ having a sequence having at least 70%, at least 75%, at least 80%, at least 85%, at least 90%, at least 95%, at least 97%, at least 98% or at least 99% sequence identity to the amino acid sequence of SEQ ID NO:9, and a $V_L$ having a sequence having at least 70%, at least 75%, at least 80%, at least 85%, at least 90%, at least 95%, at least 97%, at least 98% or at least 99% sequence identity to the amino acid sequence of SEQ ID NO:10.

In a certain embodiment, the disclosure provides an anti-EGFR antibody or anti-EGFR binding fragment comprising a $V_H$ having an amino acid sequence corresponding to SEQ ID NO:9, and a $V_L$ having an amino acid sequence corresponding to SEQ ID NO:10. This anti-EGFR antibody or binding fragment corresponds to a humanized version of MAb225, and is also referred to herein as hu225. hu225 has three heavy chain CDRs, referred to herein (in amino- to carboxy-terminal order) as CDR-H1, CDR-H2 and CDR-H3, and three light chain CDRs referred to herein (in amino- to carboxy-terminal order) as CDR-L1, CDR-L2 and CDR-L3. The sequences of the hu225 CDRs are shown in FIGS. 1B and 1C, and their numbering is set forth in FIG. 7 (for heavy chain CDRs) and FIG. 8 (for light chain CDRs). The CDRs of cetuximab and hu225 have identical amino acid sequences. hu225 has reduced immunogenicity as compared to cetuximab.

The present disclosure also relates to anti-EGFR antibodies and anti-EGFR binding fragments that have improved affinity to EGR as compared to hu225 and/or cetuximab. The anti-EGFR antibodies or anti-EGFR binding fragments can comprise six CDRs having amino acid sequences with overall at least 70% sequence identity to the CDRs of the antibody hu225 and/or cetuximab. In certain embodiments, the anti-EGFR antibodies or an anti-EGFR binding fragments of the disclosure comprises six CDRs having amino acid sequences with overall at least 75%, 80%, 85%, 90%, 91%, 92%, 93%, 94%, 95%, 96%, 97%, or 98% sequence identity to the CDRs of the antibody hu225 and/or cetuximab.

The anti-EGFR antibodies and anti-EGFR binding fragments of the disclosure can have up to 17 amino acid substitutions in their CDRs as compared to cetuximab and/or hu225. For example, the anti-EGFR antibodies or anti-EGFR binding fragments of the disclosure can have altogether up to 17, up to 16, up to 15, up to 14, up to 13, up to 12, up to 11, up to 10, up to 9, up to 8, up to 7, up to 6, up to 5, up to 4, up to 3 amino acid substitutions in the six CDRs as compared to the corresponding CDRs of cetuximab and/or hu225.

In some aspects, the anti-EGFR antibodies or anti-EGFR binding fragments of the disclosure have no more than four, no more than three or no more than two amino acid substitutions in any individual CDR as compared to the corresponding CDR sequence of the antibody cetuximab.

The anti-EGFR antibodies or anti-EGFR binding fragments of the disclosure can have at least one substitution in a heavy chain CDR as compared to cetuximab or to hu225 and/or the anti-EGFR antibodies or anti-EGFR binding fragments have at least one substitution in a light chain CDR as compared to cetuximab or to hu225. In certain aspects, the anti-EGFR antibodies or anti-EGFR binding fragments have one, two, three, four, five or all six of the following features:

at least one substitution in CDR-H1 as compared to CDR-H1 of cetuximab or hu225, at least one substitution in CDR-H2 as compared to CDR-H2 of cetuximab or hu225, at least one substitution in CDR-H3 as compared to CDR-H3 of cetuximab or hu225, at least one substitution in CDR-L1 as compared to CDR-L1 of cetuximab or hu225, at least one substitution in CDR-L2 as compared to CDR-L2 of cetuximab or hu225, and/or at least one substitution in CDR-L3 as compared to CDR-L3 of cetuximab or hu225.

In certain aspects, the anti-EGFR antibodies or anti-EGFR binding fragments of the disclosure have at least one of the following CDR-H1 substitutions as compared to CDR-H1 of cetuximab or hu225: N31V, Y32R, V34L, and V34N.

In other aspects, the anti-EGFR antibodies or anti-EGFR binding fragments of the disclosure have at least one of the following CDR-H1 substitutions as compared to CDR-H1 of cetuximab or hu225: N31D, N31I, V34E and V34Q.

In other aspects, the anti-EGFR antibodies or anti-EGFR binding fragments of the disclosure have at least one of the following CDR-H1 substitutions as compared to CDR-H1 of cetuximab or hu225: Y32W, G33A, G33D and G33E, and optionally wherein position 3 in CDR-H3 of the anti-EGFR antibody is not aspartic acid.

In some aspects, the anti-EGFR antibodies or anti-EGFR binding fragments of the disclosure have one or more of the following CDR-H2 substitutions as compared to CDR-H2 of cetuximab or hu225: V50L, V50Q, I51G, I51M, I51S, I51Q, W52G, W52T, S53Q, S53T, G55D, N56G, T57A, T57D, T57G, T57S, Y59A, Y59C, Y59E, Y59F, Y59G, Y59S, Y59W, N60D and T64E.

In other aspects, the anti-EGFR antibodies or anti-EGFR binding fragments of the disclosure have at least the following CDR-H2 substitution as compared to cetuximab or hu225: Y59H.

In further aspects, the anti-EGFR antibodies or anti-EGFR binding fragments of the disclosure have at least one of the following CDR-H2 substitutions as compared to CDR-H2 of cetuximab or hu225: V50E, V50I, I51A, I51C, S53N, G55A, G55E, G55H, T57E, Y59P and Y59Q.

In still further aspects, the anti-EGFR antibodies or anti-EGFR binding fragments of the disclosure have at least the following CDR-H2 substitution as compared to CDR-H2 of cetuximab or hu225: T57P, and optionally wherein position 3 in CDR-H3 of the anti-EGFR antibody is not aspartic acid.

In other aspects, the anti-EGFR antibodies or anti-EGFR binding fragments of the disclosure have the following CDR-H2 substitution as compared to CDR-H2 of cetuximab or hu225: F63V, and optionally wherein position 13 in CDR-H2 of the anti-EGFR antibody is not serine and/or position 15 in CDR-H2 of the anti-EGFR antibody is not lysine and/or position 16 in CDR-H2 of the anti-EGFR antibody is not glycine.

In still other aspects, the anti-EGFR antibodies or anti-EGFR binding fragments of the disclosure have at least the following CDR-H2 substitution as compared to CDR-H2 of cetuximab or hu225: N56A, and optionally wherein position 12 in CDR-H2 of the anti-EGFR antibody is not glutamic acid.

In some aspects, the anti-EGFR antibodies or anti-EGFR binding fragments of the disclosure have at least the following CDR-H2 substitution as compared to CDR-H2 of cetuximab or hu225: T61E, and optionally wherein position 7 in CDR-H2 of the anti-EGFR antibody is not alanine.

In some aspects, the anti-EGFR antibodies or anti-EGFR binding fragments of the disclosure have at least the following CDR-H3 substitution as compared to the CDR-H3 of cetuximab or hu225: Y98W.

In other aspects, the anti-EGFR antibodies or anti-EGFR binding fragments of the disclosure have at least the following CDR-H3 substitution as compared to CDR-H3 of cetuximab or hu225: T97D, and optionally wherein the CDR-H3 sequence of the anti-EGFR antibodies or anti-EGFR binding fragments does not consist of a CDR-H3 recited in FIG. 17.

In still other aspects, the anti-EGFR antibodies or anti-EGFR binding fragments of the disclosure have at least the following CDR-H3 substitution as compared to CDR-H3 of cetuximab or hu225: F100cY, and optionally wherein position 3 in CDR-H3 of the anti-EGFR antibody is not aspartic acid.

In certain aspects, the anti-EGFR antibodies or anti-EGFR binding fragments of the disclosure have at least one of the following CDR-L1 substitutions as compared to CDR-L1 of cetuximab or hu225: A25V, A25S and G30Y.

In some aspects, the anti-EGFR antibodies or anti-EGFR binding fragments of the disclosure have at least one of the following CDR-L1 substitutions as compared to CDR-L1 of cetuximab or hu225: A25I, A25P, A25T, A25Y, G30C, G30H, G30K, G30Q and G30R.

In some aspects, the anti-EGFR antibodies or anti-EGFR binding fragments of the disclosure have at least one of the following CDR-L1 substitutions as compared to CDR-L1 of cetuximab or hu225: R24P, A25C, A25F, A25M, A25L, Q27W, S28R, G30W, G30F, G30T, G30M, G30S, T31V, T31E and N32H.

In further aspects, the anti-EGFR antibodies or anti-EGFR binding fragments of the disclosure have at least one of the following CDR-L1 substitutions as compared to CDR-L1 of cetuximab or hu225: Q27E and Q27F, optionally wherein position 9 in CDR-L3 of said anti-EGFR antibody is not serine.

In other aspects, the anti-EGFR antibodies or anti-EGFR binding fragments of the disclosure have at least the following CDR-L1 substitution as compared to CDR-L1 of cetuximab or hu225: Q27Y, optionally wherein position 5 in CDR-L3 of said anti-EGFR antibody is not aspartic acid or glutamine and/or position 9 in CDR-L3 of said anti-EGFR antibody is not serine.

In still other aspects, the anti-EGFR antibodies or anti-EGFR binding fragments of the disclosure have at least one of the following CDR-L1 substitutions as compared to CDR-L1 of cetuximab or hu225: S26D and T31D, optionally wherein position 5 in CDR-L3 of said anti-EGFR antibody is not alanine.

In further aspects, the anti-EGFR antibodies or anti-EGFR binding fragments of the disclosure have at least one of the following CDR-L3 substitutions as compared to CDR-L3 of cetuximab or hu225: N91L, N92L, N92R, T97A, T97D, T97E and T97P.

In some aspects, the anti-EGFR antibodies or anti-EGFR binding fragments of the disclosure have at least one of the following CDR-L3 substitutions as compared to CDR-L3 of cetuximab or hu225: N92K, N92M, T97C, T97K, T97N and T97Q.

In other aspects, the anti-EGFR antibodies or anti-EGFR binding fragments of the disclosure have at least one of the following CDR-L3 substitutions as compared to CDR-L3 of cetuximab or hu225: T97I, T97G, T97L, T97H, and T97R.

In still other aspects, the anti-EGFR antibodies or anti-EGFR binding fragments of the disclosure have at least one the following CDR-L3 substitutions as compared to CDR-L3 of cetuximab or hu225: T96L.

In further aspects, the anti-EGFR antibodies or anti-EGFR binding fragments of the disclosure have at least one of the following CDR-L3 substitutions as compared to CDR-L3 of cetuximab or hu225: N93D and N93E, optionally wherein position 9 in CDR-L3 of said anti-EGFR antibody is not serine and/or position 4 in CDR-L3 of said anti-EGFR antibody is not tyrosine or histidine.

In other aspects, the anti-EGFR antibodies or anti-EGFR binding fragments of the disclosure have at least the following CDR-L3 substitution as compared to CDR-L3 of cetuximab or hu225: N93A, optionally wherein position 8 in CDR-L3 of said anti-EGFR antibody is not glutamic acid.

In still other aspects, the anti-EGFR antibodies or anti-EGFR binding fragments of the disclosure have at least the following CDR-L3 substitution as compared to CDR-L3 of cetuximab or hu225: T97S, optionally wherein position 5 in CDR-L3 of said anti-EGFR antibody is not aspartic acid, glutamic acid or lysine, and/or position 4 in CDR-L3 of said anti-EGFR antibody is not glutamic acid, phenylalanine, tyrosine or histidine.

In some aspects, the anti-EGFR antibodies or anti-EGFR binding fragments of the disclosure comprise combinations of mutations, including combinations of mutations in different CDRs, such as of those disclosed above.

For example, in one aspect, the anti-EGFR antibodies or anti-EGFR binding fragments has the following CDR substitutions as compared to the corresponding CDRs of cetuximab or hu225: I51G in CDR-H2, Y98W in CDR-H3, G30Y in CDR-L1, and N92L in CDR-L3. In another aspect, the anti-EGFR antibodies or anti-EGFR binding fragments have the following CDR substitutions as compared to the corresponding CDRs of cetuximab or hu225: N31V in CDR-H1, V50L in CDR-H2, A25V in CDR-L1 and N91L in CDR-L3.

In certain embodiments, the anti-EGFR antibodies and anti-EGFR binding fragments further have one or more CDR mutations or combinations of CDR mutations that do not destroy the antibody or binding fragment's ability to bind EGFR, for example as disclosed in FIGS. 15 and 16, and/or known mutations, such as those disclosed in FIGS. 17, 18 and 19. In other embodiments, the anti-EGFR antibodies and anti-EGFR binding fragments further have one or more CDR mutations or combinations of CDR mutations selected from one or more of FIGS. 9, 10, 11, 12, 13, 14, 15, 16, 17, 18 and 19. In yet other embodiments, the anti-EGFR antibodies and anti-EGFR binding fragments further have one or more CDR mutations or combinations of CDR mutations selected from one or more of FIGS. 9, 10, 11, 12, 13, 14, 15, 16, 17, 18, 19 and 20.

In certain embodiments, other than one or more of the foregoing CDR substitutions or mutations, the anti-EGFR antibodies or anti-EGFR binding fragments have a $V_H$ sequence corresponding to SEQ ID NO:1 and a $V_L$ sequence corresponding to SEQ ID NO:2. In other embodiments, other than said one or more of the foregoing CDR substitutions or mutations, the anti-EGFR antibodies or anti-EGFR binding fragments have $V_H$ sequence corresponding to SEQ ID NO:9 and a $V_L$ sequence corresponding to SEQ ID NO:10.

In yet further aspects, the anti-EGFR antibodies or anti-EGFR binding fragments of the disclosure has increased affinity to EGFR as compared to cetuximab and/or hu225, preferably as determined by fluorescence activated cell sorting ("FACS"). The anti-EGFR antibodies or anti-EGFR binding fragments of the disclosure can have an affinity that is at least 1.1-fold, at least 1.2-fold, at least 1.3-fold, at least 1.4-fold, at least 1.5-fold, at least 1.75-fold, at least 2-fold, at least 2.5-fold, at least 3-fold, at least 4-fold, or at least 5-fold the affinity of cetuximab and/or hu225, as determined by FACS. In further aspects, the anti-EGFR antibodies or anti-EGFR binding fragments can have an affinity that is up to 10-fold, up to 15-fold, up to 20-fold, up to 25-fold, up to 30-fold, up to 40-fold, up to 50-fold, or up to 100-fold that of cetuximab and/or hu225, as determined by FACS. Preferably, the binding affinity of an antibody of the disclosure containing one or more CDRs substitutions relative to the CDRs of cetuximab or hu225 is assessed in a reference antibody that is identical in sequence but for said one or more CDR substitutions.

In yet further aspects, the anti-EGFR antibody or anti-EGFR antibody can have an affinity that is 2- to 1000-fold, 10- to 100-fold, 1.5- to 50-fold or 2- to 30-fold greater than the affinity of an antibody having a $V_H$ sequence corresponding to SEQ ID NO:1 and a $V_L$ sequence corresponding to SEQ ID NO:2. In still further aspects, the anti-EGFR antibody or anti-EGFR antibody can have an affinity that is 4- to 400-fold, 10- to 100-fold, 1.5- to 50-fold or 2- to 30-fold greater than the affinity of an antibody having a $V_H$ sequence corresponding to SEQ ID NO:9 and a $V_L$ sequence corresponding to SEQ ID NO:10.

In certain aspects, the antibodies of the disclosure have $V_H$ and $V_L$ sequences having at least 80% sequence identity (and in certain embodiments, at least 85%, at least 90%, at least 95%, at least 98%, or at least 99% sequence identity) to the $V_H$ and $V_L$ sequences of cetuximab or of hu225, and include at least one amino acid substitution in at least one CDR as compared to cetuximab or to hu225. In specific embodiments, the percentage sequence identity for the heavy chain and the light chain compared to the $V_H$ and $V_L$ sequences of cetuximab or of hu225 is independently selected from at least 80%, at least 85%, at least 90%, at least 95%, at least 98%, or at least 99% sequence identity. In certain aspects, the antibodies of the disclosure have $V_H$ and/or $V_L$, sequences having at least 95%, at least 98% or at least 99% sequence identity to the $V_H$ and/or $V_L$, sequences of hu225.

In some aspects, the anti-EGFR antibodies or anti-EGFR binding fragments of the disclosure are monoclonal antibodies or an anti-EGFR binding fragments of monoclonal antibodies, respectively. In certain aspects, the anti-EGFR antibodies or anti-EGFR binding fragments of the disclosure are human or humanized antibodies or anti-EGFR binding fragment of human or humanized antibodies, respectively. The anti-EGFR antibodies or anti-EGFR binding fragments of the disclosure can be an IgG including $IgG_1$ or $IgG_2$. The anti-EGFR antibodies or anti-EGFR binding fragments of the disclosure can be non-fucosylated.

Furthermore, the anti-EGFR antibodies or anti-EGFR binding fragments can include one or more mutations in the Fc region that increases or decreases antibody-dependent cell-mediated cytotoxicity ("ADCC"). The anti-EGFR antibodies or anti-EGFR binding fragments can include one or more mutations in the Fc region that increases binding to FcγR or FcRn.

In some aspects, the anti-EGFR antibodies or anti-EGFR binding fragments of the disclosure have reduced immunogenicity as compared to the antibody cetuximab. In one aspect, the disclosure provides an anti-EGFR antibody or anti-EGFR binding fragment that comprises a $V_H$ sequence corresponding to SEQ ID NO:9 and a $V_L$ sequence corresponding to SEQ ID NO:10.

In some aspects, the anti-EGFR antibodies or anti-EGFR binding fragments of the disclosure are purified. In yet further aspects, the anti-EGFR antibodies or anti-EGFR binding fragments are purified to at least 85%, to at least 90%, to at least 95%, or to at least 98% homogeneity.

In another aspect, the anti-EGFR antibodies or anti-EGFR binding fragments of the disclosure are provided as antibody-drug conjugates.

In further aspects, the anti-EGFR antibodies or anti-EGFR binding fragments are provided with a pharmaceutically acceptable carrier as a pharmaceutical composition. In another aspect, the present disclosure provides pharmaceutical compositions comprising modified anti-EGFR antibodies having increased affinity to EGFR as compared to cetuximab or to hu225 and/or reduced immunogenicity as compared to cetuximab.

Nucleic acids comprising nucleotide sequences encoding the anti-EGFR antibodies and anti-EGFR binding fragments of the disclosure are also provided herein, as are vectors comprising nucleic acids. Additionally, prokaryotic and eukaryotic host cells transformed with a vector comprising a nucleotide sequence encoding the anti-EGFR antibodies or anti-EGFR binding fragments of the disclosure are provided herein, as well as eukaryotic (such as mammalian) host cells engineered to express the nucleotide sequences. Methods of producing anti-EGFR antibodies and anti-EGFR binding fragments by culturing host cells are also provided.

The anti-EGFR antibodies and anti-EGFR binding fragments of the disclosure are useful in the treatment of diseases such as epithelial cancers and Menetrier's disease. In particular, the anti-EGFR antibodies are useful in the treatment of epithelial cancers such as breast cancer, ovarian cancer, lung cancer, colorectal cancer, anal cancer, prostate cancer, kidney cancer, bladder cancer, head and neck cancer, ovarian cancer, pancreatic cancer, skin cancer, oral cancer, esophageal cancer, vaginal cancer, cervical cancer, cancer of the spleen, testicular cancer, and cancer of the thymus. The anti-EGFR antibodies and anti-EGFR binding fragments are therefore useful for the treatment of cancer, including squamous cell carcinoma of the head and neck and colorectal cancer.

In one aspect, a method of treating cancer comprising administering to a human in need thereof a therapeutically effective amount of an anti-EGFR antibody or anti-EGFR binding fragment of the disclosure, an antibody-drug conjugate of the disclosure, or a pharmaceutical composition of the disclosure is provided.

It should be noted that the indefinite articles "a" and "an" and the definite article "the" are used in the present application, as is common in patent applications, to mean one or more unless the context clearly dictates otherwise. Further, the term "or" is used in the present application, as is common in patent applications, to mean the disjunctive "or" or the conjunctive "and."

All publications mentioned in this specification are herein incorporated by reference. Any discussion of documents, acts, materials, devices, articles or the like that has been included in this specification is solely for the purpose of providing a context for the present disclosure. It is not to be taken as an admission that any or all of these matters form part of the prior art base or were common general knowledge in the field relevant to the present disclosure as it existed anywhere before the priority date of this application.

The features and advantages of the disclosure will become further apparent from the following detailed description of embodiments thereof.

5. BRIEF DESCRIPTION OF THE FIGURES

FIGS. 1A through 1C. FIG. 1A shows the amino acid sequences of the cetuximab heavy and light chain variable regions, SEQ ID NO:1 and SEQ ID NO:2, respectively, with CDR regions in bold, underlined text. FIG. 1B shows the amino acid sequences of the hu225 heavy and light chain variable regions, SEQ ID NO:9 and SEQ ID NO:10, respectively, with CDR regions in bold, underlined text. FIG. 1C shows the CDR sequences and corresponding sequence identifiers of cetuximab and hu225.

FIGS. 2A-2B shows the binding affinities ($IC_{50}$) of cetuximab and hu225 to EGFR (FIG. 2B) as measured in FACS competition assays with biotinylated cetuximab (as shown in FIG. 2A).

FIG. 4-1 through 4-2 shows the amino acid sequences of all VH and VL peptides of cetuximab tested as potential $CD4^+$ epitopes.

FIG. 5-1 through 5-2 shows the amino acid sequences of all VH and VL peptides of hu225 tested as potential $CD4^+$ epitopes.

FIGS. 6A-6B. FIG. 6A shows the average stimulation index calculated for all $V_H$ and $V_L$ peptides of cetuximab tested as potential CD4+ epitopes. FIG. 6B shows the average stimulation index calculated for all $V_H$ and $V_L$ peptides of hu225 tested as potential CD4+ epitopes.

FIG. 7 shows the numbering of the amino acids in the heavy chain CDRs of cetuximab and hu225.

FIG. 8 shows the numbering of the amino acids in the light chain CDRs of cetuximab and hu225.

FIG. 9 shows mutations in the cetuximab and hu225 heavy chain CDRs that preliminary binding studies indicate increase affinity toward EGFR.

FIG. 10 shows mutations in the cetuximab and hu225 light chain CDRs that preliminary binding studies indicate increase affinity toward EGFR.

FIG. 11 shows candidate mutations in the cetuximab and hu225 heavy chain CDRs for increasing affinity toward EGFR.

FIG. 12 shows candidate mutations in the cetuximab and hu225 light chain CDRs for increasing affinity toward EGFR.

FIG. 13 shows additional candidate mutations in the cetuximab and hu225 heavy chain CDRs for increasing affinity toward EGFR.

FIG. 14 shows additional candidate mutations in the cetuximab and hu225 light chain CDRs for increasing affinity toward EGFR.

FIG. 15 shows mutations in the cetuximab and hu225 heavy chain CDRs that do not substantially impact EGFR binding and can be incorporated into the antibodies of the disclosure.

FIG. 16 shows mutations in the cetuximab and hu225 light chain CDRs that do not substantially impact EGFR binding and can be incorporated into the antibodies of the disclosure.

FIGS. 17-1 through 17-2 shows known mutations in the cetuximab and hu225 heavy chain CDRs that can be incorporated into the antibodies of the disclosure.

FIG. 18 shows known mutations in the cetuximab and hu225 light chain CDRs that can be incorporated into the antibodies of the disclosure.

FIG. 19 shows known mutations in the heavy and light chain CDRs of a single chain Fv antibody that can be incorporated into the antibodies of the disclosure.

Figure 3:
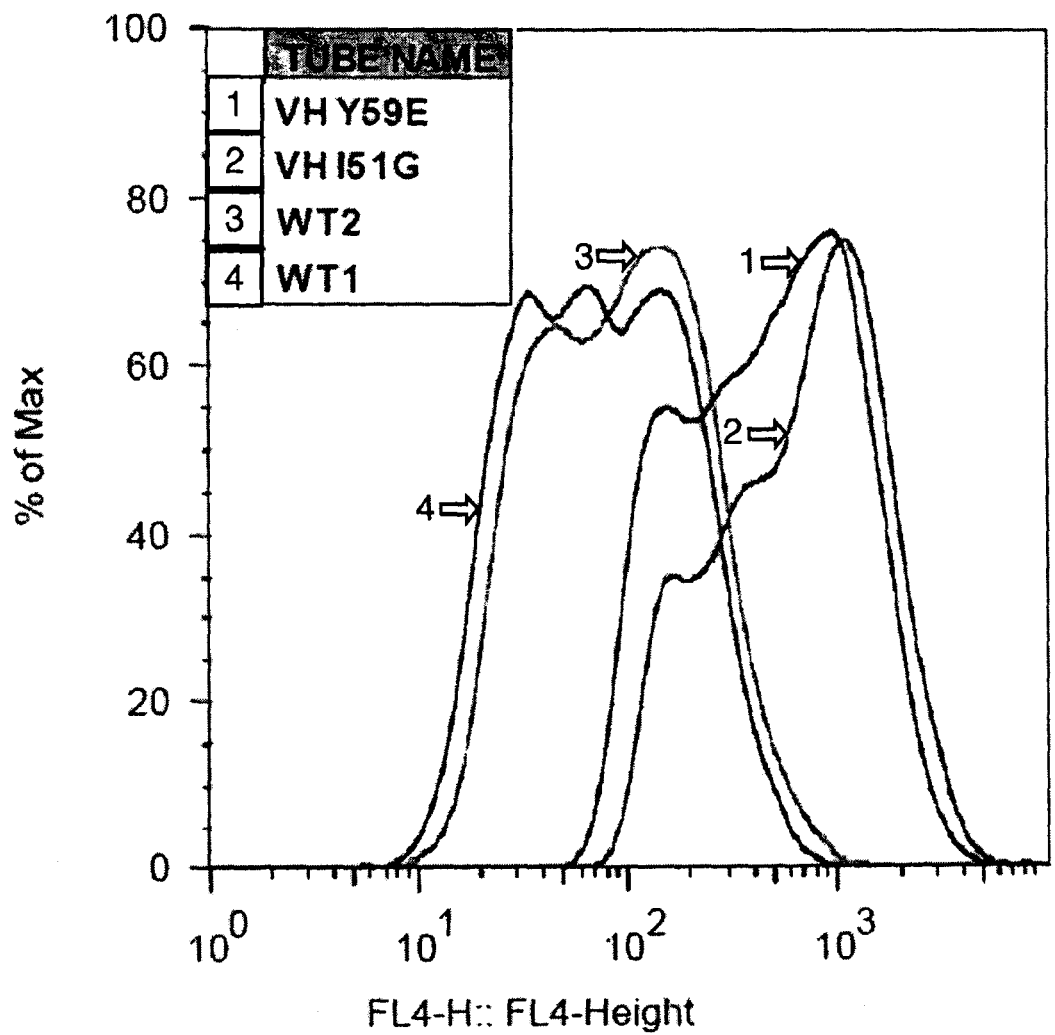
FIG. 3 shows the results of FACS analysis of binding affinities of certain variants of the disclosure. From left to right, the traces are from (1) wild type hu225 (trial 1), (ii) wild type hu225 (trial 2), (iii) hu225 variant Y59E, and (iv) hu225 variant I51G.

FIGS. 20-1 through 20-3 shows the relative binding affinities of exemplary variants of the disclosure as compared to hu225 as assessed by fluorescence-activated cell sorting (FACS), enzyme-linked immunosorbent assay (ELISA), AlphaLISA® analysis, BIAcore analysis, and/or kinetic exclusion assay (KinExA) analysis. FIGS. 20-1 and 20-2 show the relative binding of single substitution variants with increased affinity for EGFR. FIG. 20-3 shows the relative binding of two multiple substitution variants with increased affinity for EGFR.

6. DETAILED DESCRIPTION

6.1 Anti-EGFR Antibodies

The present disclosure provides anti-EFGR antibodies. Unless indicated otherwise, the term "antibody" (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), and antigen binding fragments of antibodies, including, e.g., Fab', F(ab')$_2$, Fab, Fv, rIgG, and scFv fragments. Moreover, unless otherwise indicated, the term "monoclonal antibody" (mAb) is meant to include both intact molecules, as well as, antibody fragments (such as, for example, Fab and F(ab')$_2$ fragments) which are capable of specifically binding to a protein. Fab and F(ab')$_2$ fragments lack the Fc fragment of intact antibody, clear more rapidly from the circulation of the animal, and may have less non-specific tissue binding than an intact antibody (Wahl et al., 1983, J. Nucl. Med. 24:316).

The term "scFv" refers to a single chain Fv antibody in which the variable domains of the heavy chain and the light chain from a traditional antibody have been joined to form one chain.

References to "VH" refer to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 Daltons, composed of two identical light (L) chains and two identical heavy (H) chains. Each heavy chain has at the amino terminus a variable domain ($V_H$) followed by a number of constant domains. Each light chain has at the amino terminus a variable domain ($V_L$) and a constant domain at the carboxy terminus.

"Cetuximab" refers to the chimeric human/mouse antibody known as Erbitux®.

"hu225" refers to a humanized version of MAb225, which is the parent antibody of the chimeric antibody C225 (also known as cetuximab or Erbitux®).

The anti-EGFR antibodies of the disclosure bind to human EGFR and inhibit its activity in a cell.

The anti-EGFR antibodies of the disclosure contain complementarity determining regions (CDRs) that are related in sequence to the CDRs of the antibody cetuximab and of the antibody hu225.

CDRs are also known as hypervariable regions both in the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions in the order FR1-CDR1-FR2-CDR2-FR3-CDR3-FR4 and, with the CDRs from the other chain, contribute to the formation of the target binding site of antibodies (see Kabat et al., Sequences of Proteins of Immunological Interest (National Institute of Health, Bethesda, Md. 1987)). As used herein, numbering of immunoglobulin amino acid residues is done according to the immunoglobulin amino acid residue numbering system of Kabat et al., unless otherwise indicated.

The sequences of the heavy and light chain variable regions of cetuximab are represented by SEQ ID NO:1 and SEQ ID NO:2, respectively. The sequences of the heavy and light chain variable regions are also depicted in FIG. 1A. The sequences of the CDRs of cetuximab, and their corresponding identifiers, are presented in FIG. 1C. Any nucleotide sequences encoding SEQ ID NO:1 or SEQ ID NO:2 can be used in the compositions and methods of the present disclosure.

The sequences of the heavy and light chain variable regions of hu225 are represented by SEQ ED NO:9 and SEQ ID NO:10, respectively. The sequences of the heavy and light chain variable regions are also depicted in FIG. 1B. The sequences of the CDRs of hu225, which are identical to the sequences of the CDRs of cetuximab, and their sequence identifiers are presented in FIG. 1C. Any nucleotide sequences encoding SEQ ID NO:9 or SEQ ID NO:10 can be used in the compositions and methods of the present disclosure.

The present disclosure further provides anti-EGFR antibody fragments comprising CDR sequences that are related to the CDR sequences of cetuximab and of hu225. The term "antibody fragment" refers to a portion of a full-length antibody, generally the target binding or variable region. Examples of antibody fragments include Fab, Fab', F(ab')$_2$ and Fv fragments. An "Fv" fragment is the minimum antibody fragment that contains a complete target recognition and binding site. This region consists of a dimer of one heavy and one light chain variable domain in a tight, noncovalent association ($V_H$-$V_L$ dimer). It is in this configuration that the three CDRs of each variable domain interact to define a target binding site on the surface of the $V_H$-$V_L$ dimer. Often, the six CDRs confer target binding specificity to the antibody. However, in some instances even a single variable domain (or half of an Fv comprising only three CDRs specific for a target) can have the ability to recognize and bind target. "Single chain Fv" or "scFv" antibody fragments comprise the $V_H$ and $V_L$ domains of an antibody in a single polypeptide chain. Generally, the Fv polypeptide further comprises a polypeptide linker between the $V_H$ and $V_L$ domains which enables the scFv to form the desired structure for target binding. "Single domain antibodies" are composed of a single $V_H$ or $V_L$ domain that exhibit sufficient affinity to the target. In a specific embodiment, the single domain antibody is a camelid antibody (see, e.g., Riechmann, 1999, Journal of Immunological Methods 231:25-38).

The Fab fragment contains the constant domain of the light chain and the first constant domain ($CH_1$) of the heavy chain. Fab' fragments differ from Fab fragments by the addition of a few residues at the carboxyl terminus of the heavy chain $CH_1$ domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art.

In certain embodiments, the anti-EGFR antibodies of the disclosure are monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies useful in connection with the present disclosure can be prepared using a wide variety of techniques known in the art including the use of hybridoma, recombinant, and phage display technologies, or a combination thereof. The anti-EGFR antibodies of the disclosure include chimeric, primatized, humanized, or human antibodies.

The anti-EGFR antibodies of the disclosure can be chimeric antibodies. The term "chimeric" antibody as used herein refers to an antibody having variable sequences derived from a non-human immunoglobulin, such as rat or mouse antibody, and human immunoglobulin constant regions, typically chosen from a human immunoglobulin template. Methods for producing chimeric antibodies are known in the art. See, e.g., Morrison, 1985, Science 229 (4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397, which are incorporated herein by reference in their entireties.

The anti-EGFR antibodies of the disclosure can be humanized. "Humanized" forms of non-human (e.g., murine) antibodies are chimeric immunoglobulins, immunoglobulin chains or fragments thereof (such as Fv, Fab, Fab', F(ab')$_2$ or other target-binding subdomains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

The anti-EGFR antibodies of the disclosure can be human antibodies. Completely "human" anti-EGFR antibodies can be desirable for therapeutic treatment of human patients. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Medarex (Princeton, N.J.), Astellas Pharma (Deerfield, Ill.), Amgen (Thousand Oaks, Calif.) and Regeneron (Tarrytown, N.Y.) can be engaged to provide human antibodies directed against a selected antigen using technology similar to that described above. Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1988, Biotechnology 12:899-903).

The anti-EGFR antibodies of the disclosure can be primatized. The term "primatized antibody" refers to an antibody comprising monkey variable regions and human constant regions. Methods for producing primatized antibodies are known in the art. See e.g., U.S. Pat. Nos. 5,658,570; 5,681, 722; and 5,693,780, which are incorporated herein by reference in their entireties.

The anti-EGFR antibodies of the disclosure can be bispecific antibodies. Bispecific antibodies are monoclonal, often human or humanized, antibodies that have binding specificities for at least two different antigens. In the present disclosure, one of the binding specificities can be directed towards EGFR, the other can be for any other antigen, e.g., for a cell-surface protein, receptor, receptor subunit, tissue-specific antigen, virally derived protein, virally encoded envelope protein, bacterially derived protein, or bacterial surface protein, etc.

The anti-EGFR antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein (see Section 6.4 for a discussion of antibody conjugates), etc. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (see, e.g., Wolfson, 2006, Chem. Biol. 13(10):1011-2).

In yet another embodiment of the disclosure, the anti-EGFR antibodies or fragments thereof can be antibodies or antibody fragments whose sequence has been modified to alter at least one constant region-mediated biological effector function relative to the corresponding wild type sequence.

For example, in some embodiments, an anti-EGFR antibody of the disclosure can be modified to reduce at least one constant region-mediated biological effector function relative to an unmodified antibody, e.g., reduced binding to the Fc receptor (FcγR). FcγR binding can be reduced by mutating the immunoglobulin constant region segment of the antibody at particular regions necessary for FcγR interactions (see e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization and phagocytosis and antibody-dependent cellular cytotoxicity ("ADCC").

In other embodiments, an anti-EGFR antibody of the disclosure can be modified to acquire or improve at least one constant region-mediated biological effector function relative to an unmodified antibody, e.g., to enhance FcγR interactions (see, e.g., US 2006/0134709). For example, an anti-EGFR antibody of the disclosure can have a constant region that binds FcγRIIA, FcγRIIB and/or FcγRIIIA with greater affinity than the corresponding wild type constant region.

Thus, antibodies of the disclosure can have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" shown in FIG. 3 of U.S. Pat. No. 5,834, 597, in which residue 236 is deleted and residues 234, 235 and 237 (using EU numbering) are substituted with alanines.

In some embodiments, the anti-EGFR antibodies of the disclosure have low levels of or lack fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

In yet another aspect, the anti-EGFR antibodies or fragments thereof can be antibodies or antibody fragments that have been modified to increase or reduce their binding affinities to the fetal Fc receptor, FcRn, for example, by mutating the immunoglobulin constant region segment at particular regions involved in FcRn interactions (see e.g., WO 2005/123780). In particular embodiments, an anti-EGFR antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of U.S. Pat. No. 7,217,797, which table is incorporated by reference herein in its entirety. Such mutations increase the antibody's binding to FcRn, which protects the antibody from degradation and increases its half-life.

In yet other aspects, an anti-EGFR antibody has one or more amino acids inserted into one or more of its hypervariable regions, for example, as described in Jung and Plückthun, 1997, Protein Engineering 10(9):959-966; Yazaki et al., 2004, Protein Eng Des. Sel. 17(5):481-9. Epub 2004 Aug. 17; and US 2007/0280931.

In various embodiments, the anti-EGFR antibodies or fragments thereof can be antibodies or antibody fragments that have been modified for increased expression in heterologous hosts. In certain embodiments, the anti-EGFR antibodies or fragments thereof can be antibodies or antibody fragments that have been modified for increased expression in and/or secretion from heterologous host cells. In some embodiments, the anti-EGFR antibodies or fragments thereof are modified for increased expression in bacteria, such as *E. coli*. In other embodiments, the anti-EGFR antibodies or fragments thereof are modified for increased expression in yeast (Kieke et al., 1999, Proc. Nat'l Acad. Sci. USA 96:5651-5656). In still other embodiments, the anti-EGFR antibodies or fragments thereof are modified for increased expression in insect cells. In additional embodiments, the anti-EGFR antibodies or fragments thereof are modified for increased expression in mammalian cells, such as CHO cells.

In certain embodiments, the anti-EGFR antibodies or fragments thereof can be antibodies or antibody fragments that have been modified to increase stability of the antibodies during production. In some embodiments, the antibodies or fragments thereof can be modified to replace one or more amino acids such as asparagine or glutamine that are susceptible to nonenzymatic deamidation with amino acids that do not undergo deamidation (Huang et al., 2005, Anal. Chem. 77:1432-1439). In other embodiments, the antibodies or fragments thereof can be modified to replace one or more amino acids that is susceptible to oxidation, such as methionine, cysteine or tryptophan, with an amino acid that does not readily undergo oxidation. In still other embodiments, the antibodies or fragments thereof can be modified to replace one or more amino acids that is susceptible to cyclization, such as asparagine or glutamic acid, with an amino acid that does not readily undergo cyclization.

6.2 Nucleic Acids and Expression Systems

The present disclosure encompasses nucleic acid molecules and host cells encoding the anti-EGFR antibodies of the disclosure.

An anti-EGFR antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

In one embodiment, the anti-EGFR antibodies are similar to cetuximab but for changes in one or more CDRs (referred to herein as having "cetuximab-related" sequences). In another embodiment, the anti-EGFR antibodies are similar to hu225 but for changes in one or more CDRs (referred to herein as having "hu225-related" sequences). To generate nucleic acids encoding such anti-EGFR antibodies, DNA fragments encoding the light and heavy chain variable regions are first obtained. These DNAs can be obtained by amplification and modification of germline DNA or cDNA encoding light and heavy chain variable sequences, for example, using the polymerase chain reaction (PCR). Germline DNA sequences for human heavy and light chain variable region genes are known in the art (see e.g., the "VBASE" human germline sequence database; see also Kabat, E. A. et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference). A DNA fragment encoding the heavy or light chain variable region of cetuximab or of hu225 can be synthesized and used as a template for mutagenesis to generate a variant as described herein using routine mutagenesis techniques; alternatively, a DNA fragment encoding the variant can be directly synthesized.

Once DNA fragments encoding cetuximab or cetuximab-related $V_H$ and $V_L$ segments, or hu225 or hu225-related $V_H$ and $V_L$ segments, are obtained, these DNA fragments can be further manipulated by standard recombinant DNA techniques, for example, to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($CH_1$, $CH_2$, $CH_3$ and, optionally, $CH_4$). The sequences of human heavy chain constant region genes are known in the art (see, e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$ constant region. For a Fab fragment heavy chain gene, the $V_H$-encoding DNA can be operatively linked to another DNA molecule encoding only the heavy chain $CH_1$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al., 1991, Sequences of Proteins of Immunological Interest, Fifth Edition (U.S. Department of Health and Human Services, NIH Publication No. 91-3242)) and DNA fragments encompassing these regions can be obtained by standard PCR amplification. The light chain constant region can be a kappa or lambda constant region, but in certain embodiments is a kappa constant region. To create a scFv gene, the $V_H$ and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ regions joined by the flexible linker (see e.g., Bird et al., 1988, Science 242:423-426; Huston et al., 1988, Proc. Natl. Acad. Sci. USA 85:5879-5883; McCafferty et al., 1990, Nature 348:552-554).

To express the anti-EGFR antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the cetuximab or cetuximab-related light or heavy chain sequences, or of the hu225 or hu225-related light or heavy chain sequences, the expression vector can already carry antibody constant region sequences. For example, one approach to converting the $V_H$ and $V_L$ sequences to full-length antibody genes is to insert them into expression vectors already encoding heavy chain constant and light chain constant regions, respectively, such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies of the disclosure in either prokaryotic or eukaryotic host cells. In certain embodiments, expression of antibodies is performed in eukaryotic cells, e.g., mammalian host cells, for optimal secretion of a properly folded and immunologically active antibody. Exemplary mammalian host cells for expressing the recombinant antibodies of the disclosure include Chinese Hamster Ovary (CHO cells) (including DHFR CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NS0 myeloma cells, COS cells, 293 cells and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-EGFR antibody of this disclosure.

Recombinant DNA technology can also be used to remove some or all of the DNA encoding either or both of the light and heavy chains that is not necessary for binding to EGFR. The molecules expressed from such truncated DNA molecules are also encompassed by the antibodies of the disclosure.

In addition, bifunctional antibodies can be produced in which one heavy and one light chain are an antibody of the disclosure and the other heavy and light chain are specific for an antigen other than EGFR by crosslinking an antibody of the disclosure to a second antibody by standard chemical crosslinking methods. Bifunctional antibodies can also be made by expressing a nucleic acid engineered to encode a bifunctional antibody.

In certain embodiments, dual specific antibodies, i.e., antibodies that bind EGFR and an unrelated antigen using the same binding site, can be produced by mutating amino acid residues in the light chain and/or heavy chain CDRs. In various embodiments, dual specific antibodies that bind two antigens, such as EGFR and HER2, can be produced by mutating amino acid residues in the periphery of the antigen binding site (Bostrom et al., 2009, Science 323:1610-1614). Dual functional antibodies can be made by expressing a nucleic acid engineered to encode a dual specific antibody.

For recombinant expression of an anti-EGFR antibody of the disclosure, the host cell can be co-transfected with two expression vectors of the disclosure, the first vector encoding a heavy chain derived polypeptide and the second vector encoding a light chain derived polypeptide. Typically, the two vectors each contain a separate selectable marker. Alternatively, a single vector can be used which encodes both heavy and light chain polypeptides.

Once a nucleic acid encoding one or more portions of cetuximab, hu225 or of an anti-EGFR antibody with CDR sequences related to the CDR sequences of cetuximab or hu225 is generated, further alterations or mutations can be introduced into the coding sequence, for example, to generate nucleic acids encoding antibodies with different CDR sequences, antibodies with reduced affinity to the Fc receptor, or antibodies of different subclasses.

The anti-EGFR antibodies of the disclosure can also be produced by chemical synthesis (e.g., by the methods described in Solid Phase Peptide Synthesis, 2nd ed., 1984 The Pierce Chemical Co., Rockford, Ill.). Variant antibodies can also be generated using a cell-free platform (see, e.g., Chu et Biochemia No. 2, 2001 (Roche Molecular Biologicals)).

Once an anti-EGFR antibody of the disclosure has been produced by recombinant expression, it can be purified by any method known in the art for purification of an immunoglobulin molecule, for example, by chromatography (e.g., ion exchange, affinity, particularly by affinity for Protein A, Protein G or Protein L selection, and sizing column chromatography), centrifugation, differential solubility, or by any other standard technique for the purification of proteins. Further, the anti-EGFR antibodies of the present disclosure or fragments thereof can be fused to heterologous polypeptide sequences described herein or otherwise known in the art to facilitate purification.

Once isolated, an anti-EGFR antibody can, if desired, be further purified, e.g., by high performance liquid chromatography (See, e.g., Fisher, Laboratory Techniques In Biochemistry And Molecular Biology (Work and Burdon, eds., Elsevier, 1980)), or by gel filtration chromatography on a Superdex™ 75 column (Pharmacia Biotech AB, Uppsala, Sweden).

6.3 Biological Properties of Anti-EGFR Antibodies

In certain embodiments, the anti-EGFR antibodies of the disclosure have certain biological activities, such as competing with cetuximab or with hu225 for binding to EGFR or neutralizing EGFR activity.

Accordingly, in certain embodiments, anti-EGFR antibodies of the disclosure compete with cetuximab for binding to EGFR. In other embodiments, anti-EGFR antibodies of the disclosure compete with hu225. The ability to compete for binding to EGFR can be tested using a competition assay. In one example, of a competition assay, EGFR is adhered onto a solid surface, e.g., a microwell plate, by contacting the plate with a solution of EGFR (e.g., at a concentration of 1 µg/mL in PBS over night at 4° C.). The plate is washed (e.g., 0.1% Tween 20 in PBS) and blocked (e.g., in Superblock, Thermo Scientific, Rockford, Ill.). A mixture of sub-saturating amount of biotinylated cetuximab or hu225 (80 ng/mL) and unlabeled cetuximab or hu225 (the "reference" antibody), or competing anti-EGFR antibody (the "test" antibody) antibody in serial dilution (e.g., at a concentration of 2.8 µg/mL, 8.3 µg/mL, or 25 µg/mL) in ELISA buffer (e.g., 1% BSA and 0.1% Tween 20 in PBS) is added to wells and plates are incubated for 1 hour with gentle shaking. The plate is washed, 1 µg/mL HRP-conjugated Streptavidin diluted in ELISA buffer is added to each well and the plates incubated for 1 hour. Plates are washed and bound antibodies are detected by addition of substrate (e.g., TMB, Biofx Laboratories Inc., Owings Mills, Md.). The reaction is terminated by addition of stop buffer (e.g., Bio FX Stop Reagents, Biofx Laboratories Inc., Owings Mills, Md.) and the absorbance is measured at 650 mu using microplate reader (e.g., VERSAmax, Molecular Devices, Sunnyvale, Calif.). Variations on this competition assay can also be used to test competition between an anti-EGFR antibody of the disclosure and cetuximab or hu225. For example, in certain aspects, the anti-EGFR antibody is used as a reference antibody and cetuximab or hu225 is used as a test antibody. Additionally, instead of soluble EGFR, membrane-bound EGFR expressed on the surfaces of cell (for example, mammalian cells) in culture can be used. Other formats for competition assays are known in the art and can be employed.

In various embodiments, an anti-EGFR antibody of the disclosure reduces the binding of labeled hu225 or of labeled cetuximab by at least 30%, by at least 40%, by at least 50%, by at least 60%, by at least 70%, by at least 80%, by at least 90%, by at least 95%, by at least 99%, or by a percentage ranging between any of the foregoing values (e.g., an anti-EGFR antibody of the disclosure reduces the binding of labeled hu225 or labeled cetuximab by 50% to 70%) when the anti-EGFR antibody is used at a concentration of 0.08 µg/mL, 0.4 µg/mL, 2 µg/mL, 10 µg/mL, 50 µg/mL, 100 µg/mL or at a concentration ranging between any of the foregoing values (e.g., at a concentration ranging from 2 µg/mL to 10 µg/mL).

In various embodiments, the binding of the antibodies of the disclosure to EGFR can be determined using a Sapidyne KINEXA assay. In this assay, NHS-activated fast-flow sepharose beads (GE Healthcare) are pre-coated with antigen (50 µg anti-EGFR antibody per mL of beads) and blocked with 10 mg/mL BSA in 1 M Tris-HCl, pH 8.0. Then 2 pM, 4 pM, 40 pM of an antibody of the disclosure is incubated with various concentrations (e.g., 2.4 pM to 10 nM, serial dilutions) of soluble EGFR in running buffer (PBS, 0.005% (v/v) Tween-20 and 1 mg/mL ovalbumin) for 10 hours at room temperature. To determine the free antibody present at equilibrium, each sample is passed through soluble EGFR-coated beads. The amount of bead-bound antibody is then quantified by passing a solution of fluorescent (Cy5) labeled goat anti-human Fc antibody (Jackson Immuno Research) diluted 1:4000 in running buffer over the beads. The measured fluorescence signal is proportional to the concentration of free antibody at equilibrium. In certain embodiments, each concentration of soluble EGFR is measured in duplicate. The equilibrium dissociation constant ($K_D$) can be obtained from non-linear regression of the competition curves using a multiple-curve, one-site homogeneous binding model (KINEXA software).

The association rate constant ($k_{on}$) for soluble EGFR binding can also be determined using a Sapidyne KINEXA assay. Two pM antibody is mixed with 20 pM soluble EGFR using the same conditions as described in the previous paragraph. At various times, samples are probed for free antibody using the conditions described above for equilibrium binding, and then the resulting time dependence is fit using the KINEXA software to determine the association rate ($k_{on}$). The dissociation rate constant ($k_{off}$) is calculated using the expression $k_{off}=K_d \times k_{on}$.

In other aspects, an anti-EGFR antibody of the disclosure inhibits (or neutralizes) EGFR activity in a range of in vitro assays, such as cell proliferation, EGFR phosphorylation and apoptosis. For example, in one embodiment, the EGFR activity assayed is induction of A431 epidermal carcinoma cell proliferation (see, e.g., Sato et al, "Biological Effects in vitro of Monoclonal Antibodies to Human Epidermal Growth Factor Receptors", (1983), Mol. Biol. Med., 1, 511-529). In this assay, A431 cells are maintained in DMEM plus 10% FBS. On day 1, cells are placed in PBS for 20 minutes and trypsinized for 5 minutes prior to plating. Cells are plated at a cell density of 15,000 cells per well in 384 well format on Greiner 384 TC treated cell culture plates using a multidrop 384. Final medium volume is 50 µL. Cell culture plates are covered with airpore tape (Qiagen, Valencia, Calif.). Cells are allowed to adhere overnight. On day 2 cell culture medium is removed and replaced with either 50 µL phenol red free DMEM (no FBS) ("control wells") or DMEM and anti-EGFR antibody ("treatment wells") in duplicate at an expected concentration of 2.5 µg/mL. Two control wells are located adjacent to each treatment well for a total of 192 control wells. On day 3, medium is removed and replaced with phenol red-free DMEM containing MTS cell proliferation reagent (Promega, Madison, Wis.; 1 ml/10 mL medium). Absorbance at 490 nm is recorded after 15 and 30 minutes. The mean value for all duplicate treatments is divided by the mean for all control wells.

In certain embodiments, the activity assayed is phosphorylation of the EGFR tyrosine kinase. Such activity assays can be performed as follows. A431 cells are grown to about 70% confluence in 6-well plates and serum starved overnight in DMEM 0.5% FBS. The cells are then incubated with antibody dilutions in the presence of 100 nM EGF (Upstate) for one hour. Cells are washed with cold PBS and lysed with 0.5 mL lysis buffer. (5 OmM Tris-HCl pH 7.4, 1% IGEPGAL CA-630, 0.25% sodium deoxycholate, 150 mM NaCl, 1 mM PMSF, 1 mM sodium vanadate ($NaVO_4$), 1 mM NaF, 1/2 tablet protease cocktail in 10 mL). Insoluble material is removed by ultracentrifugation at 10,000 RPM for 30 min. Cell lysates are adjusted for protein concentration and equivalent amounts of each extract are separated by SDS-PAGE. Levels of phosphorylated EGFR are determined by Western blot developed with an anti-phospho-EGFR antibody (Upstate).

In other embodiments, anti-EGFR antibody activity is assayed by induction of apoptosis of A431 cells. In this assay, A431 cells at 20000 cells/well in 24-well plates are incubated with 1.0 ug/mL of anti-EGFR antibody for 0, 3, 7, 24 or 48 hours. Apoptosis is measured by ELISA for DNA fragmentation (Roche). Baseline apoptosis from a non-specific antibody is subtracted from the mean.

Other formats for EGFR neutralization assays are known in the art and can be employed.

In various embodiments, an anti-EGFR antibody of the disclosure neutralizes EGFR by at least 30%, by at least 40%, by at least 50%, by at least 60%, by at least 70%, by at least 80%, by at least 90%, or by a percentage ranging between any of the foregoing values (e.g., an anti-EGFR antibody of the disclosure neutralizes EGFR activity by 50% to 70%) when the anti-EGFR antibody is used at a concentration of 2 ng/mL, 5 ng/mL, 10 ng/mL, 20 ng/mL, 0.1 µg/mL, 0.2 µg/mL, 1 µg/mL, 2 µg/mL, 5 µg/mL, 10 µg/mL, 20 µg/mL, or at a concentration ranging between any of the foregoing values (e.g., at a concentration ranging from 1 µg/mL to 5 µg/mL).

In some embodiments, an anti-EGFR antibody of the disclosure is at least 0.7-fold as effective, 0.8-fold as effective, at least 0.9-fold as effective, at least 1-fold as effective, at least 1.1-fold as effective, at least 1.25-fold as effective, at least 1.5-fold as effective, at least 2-fold as effective, at least 5-fold as effective, at least 10-fold as effective, at least 20-fold as effective, at least 50-fold as effective, at least 100-fold as effective, at least 200-fold as effective, at least 500-fold as effective, at least 1000-fold as effective as cetuximab or hu225 at neutralizing EGFR, or having an effectiveness at neutralizing EGFR relative to cetuximab or hu225 ranging between any pair of the foregoing values (e.g., 0.9-fold to 5-fold as effective as cetuximab or hu225 or 2-fold to 50-fold as effective as cetuximab or hu225 in neutralizing EGFR).

6.4 Kinetic Properties of Anti-EGFR Antibodies

In certain embodiments, the anti-EGFR antibodies of the disclosure have a high binding affinity for EGFR. In specific embodiments, the anti-EGFR antibodies of the present disclosure have specific association rate constants ($k_{on}$ or $k_a$ values), dissociation rate constants ($k_{off}$ or $k_d$ values), affinity constants ($K_A$ values), dissociation constants ($K_D$ values) and/or $IC_{50}$ values. In certain aspects, such values are selected from the following embodiments.

In some embodiments, an anti-EGFR antibody of the disclosure binds to EGFR with a $K_A$ ($k_{on}/k_{off}$) of at least $10^{10}$ $M^{-1}$, at least $4 \times 10^{11}$ $M^{-1}$, at least $10^{11}$ $M^{-1}$, at least $4 \times 10^{12}$ $M^{-1}$, at least $10^{12}$ $M^{-1}$, at least $4 \times 10^{13}$ $M^{-1}$, at least $10^{13}$ $M^{-1}$, at least $4 \times 10^{14}$ $M^{-1}$, at least $10^{14}$ $M^{-1}$, at least $4 \times 10^{15}$ $M^{-1}$, at least $10^{15}$ $M^{-1}$, or with a $K_A$ of any range between any pair of the foregoing values (e.g., $4 \times 10^{11}$ $M^{-1}$ to $4 \times 10^{13}$ $M^{-1}$ or $4 \times 10^{12}$ $M^{-1}$ to $4 \times 10^{15}$ $M^{-1}$).

In certain embodiments, an anti-EGFR antibody of the disclosure binds to EGFR with a $K_D$ ($k_{off}/k_{on}$) of $10^{-10}$ or less, $4 \times 10^{-11}$ M or less, $10^{-11}$ M or less, $4 \times 10^{-12}$ M or less, $10^{-12}$ M or less, $4 \times 10^{-13}$ M or less, $10^{-13}$ M or less, $4 \times 10^{-14}$ M or less, $10^{-14}$ M or less, $4 \times 10^{-15}$ M or less, $10^{-15}$ M or less, or with a $K_D$ of any range between any pair of the foregoing values (e.g., $4 \times 10^{-11}$ M to $4 \times 10^{-13}$ M or $4 \times 10^{-12}$ M to $4 \times 10^{-15}$ M).

In specific embodiments, the $K_D$ ($k_{off}/k_{on}$) value is determined by assays well known in the art, e.g., ELISA, isothermal titration calorimetry (ITC), fluorescent polarization assay or any other biosensors such as BIAcore.

In some embodiments, an anti-EGFR antibody of the disclosure binds to EGFR and inhibits the binding of EGFR to its EGF ligand at an $IC_{50}$ less than 0.02 nM, less than 0.01 nM, less than 0.005 nM, less than 0.002 nM, less than 0.001 nM, less than $5 \times 10^{-4}$ nM, less than $2 \times 10^{-4}$ nM, less than $1 \times 10^{-4}$ nM, less than $5 \times 10^{-5}$ nM, less than $2 \times 10^{-5}$ nM, less than $1 \times 10^{-4}$ nM, less than $5 \times 10^{-6}$ nM, less than $2 \times 10^{-6}$ nM, less than $1 \times 10^{-6}$ nM, less than $5 \times 10^{-7}$ nM, less than $2 \times 10^{-7}$ nM, less than $1 \times 10^{-7}$ nM, or with an $IC_{50}$ of any range between any pair of the foregoing values (e.g., 0.02 nM to $2 \times 10^{-5}$ nM, or $5 \times 10^{-5}$ nM to $1 \times 10^{-7}$ nM). $IC_{50}$ can be measured according to methods well known in the art, e.g., ELISA.

In certain embodiments, the kinetic properties of an antibody of the disclosure are comparable to, or improved relative to, cetuximab or hu225 in a comparable assay. For example, in certain embodiments, an anti-EGFR antibody of the disclosure binds to EGFR with a $k_{on}$ rate ranging from approximately 0.5× to 1000× of the $k_{on}$ of cetuximab or of hu225, for example, a $k_{on}$ of 0.75 of the $k_{on}$ of cetuximab or of hu225, a $k_{on}$ of 1× of the $k_{on}$ of cetuximab or of hu225, a $k_{on}$ of 1.1× of the $k_{on}$ of cetuximab or of hu225, a $k_{on}$ of 1.2× of the $k_{on}$ of cetuximab or of hu225, a $k_{on}$ of 1.3× of the $k_{on}$ of cetuximab or of hu225, a $k_{on}$ of 1.4× of the $k_{on}$ of cetuximab or of hu225, a $k_{on}$ of 1.5× of the $k_{on}$ of cetuximab or of hu225, a $k_{on}$ of 1.6× of the $k_{on}$ of cetuximab or of hu225, a $k_{on}$ of 1.6× of the $k_{on}$ of cetuximab or of hu225, a $k_{on}$ of 1.7× of the $k_{on}$ of cetuximab or of hu225, a $k_{on}$ of 1.8× of the $k_{on}$ of cetuximab or of hu225, a $k_{on}$ of 1.9× of the $k_{on}$ of cetuximab or of hu225, a $k_{on}$ of 2× of the $k_{on}$ of cetuximab or of hu225, a $k_{on}$ of 2.25× of the $k_{on}$ of cetuximab or of hu225, a $k_{on}$ of 2.5× of the $k_{on}$ of cetuximab or of hu225, a $k_{on}$ of 2.75× of the $k_{on}$ of cetuximab or of hu225, a $k_{on}$ of 3× of the $k_{on}$ of cetuximab or of hu225, a $k_{on}$ of 4× of the $k_{on}$ of cetuximab or of hu225, a $k_{on}$ of 5× of the $k_{on}$ of cetuximab or of hu225, a $k_{on}$ of 6× of the $k_{on}$ of cetuximab or of hu225, a $k_{on}$ of 7× of the $k_{on}$ of cetuximab or of hu225, a $k_{on}$ of 8× of the $k_{on}$ of cetuximab or of hu225, a $k_{on}$ of 9× of the $k_{on}$ of cetuximab or of hu225, a $k_{on}$ of 10× of the $k_{on}$ of cetuximab or of hu225, a $k_{on}$ of 15× of the $k_{on}$ of cetuximab or of hu225, a $k_{on}$ of 20× of the $k_{on}$ of cetuximab or of hu225, a $k_{on}$ of 50× of the $k_{on}$ of cetuximab or of hu225, a $k_{on}$ of 75× of the $k_{on}$ of cetuximab or of hu225, a $k_{on}$ of 100× of the $k_{on}$ of cetuximab or of hu225, a $k_{on}$ of 150× of the $k_{on}$ of cetuximab or of hu225, a $k_{on}$ of 200× of the $k_{on}$ of cetuximab or of hu225, or a $k_{on}$ ranging between any pair of the foregoing values, e.g., a $k_{on}$ of 2×–75× of the $k_{on}$ of cetuximab or of hu225, a $k_{on}$ of 5×–100× of the $k_{on}$ of cetuximab or of hu225, a $k_{on}$ of 0.05×–

1000× of the $k_{on}$ of cetuximab or of hu225, a $k_{on}$ of 0.75×–250× of the $k_{on}$ of cetuximab or of hu225, etc.

In various embodiments, an anti-EGFR antibody of the disclosure binds to EGFR with a $k_{off}$ rate ranging from about 0.001× to about 3× of the $k_{off}$ of cetuximab or of hu225, for example, a $k_{off}$ of 0.002× of the $k_{off}$ of cetuximab or of hu225, a $k_{off}$ of 0.003× of the $k_{off}$ of cetuximab or of hu225, a $k_{off}$ of 0.004× of the $k_{off}$ of cetuximab or of hu225, a $k_{off}$ of 0.005× of the $k_{off}$ of cetuximab or of hu225, a $k_{off}$ of 0.006× of the $k_{off}$ of cetuximab or of hu225, a $k_{off}$ of 0.0075× of the $k_{off}$ of cetuximab or of hu225, a $k_{off}$ of 0.01× of the $k_{off}$ of cetuximab or of hu225, a $k_{off}$ of 0.025× of the $k_{off}$ of cetuximab or of hu225, a $k_{off}$ of 0.05× of the $k_{off}$ of cetuximab or of hu225, a $k_{off}$ of 0.075× of the $k_{off}$ of cetuximab or of hu225, a $k_{off}$ of 0.1× of the $k_{off}$ of cetuximab or of hu225, a $k_{off}$ of 0.25× of the $k_{off}$ of cetuximab or of hu225, a $k_{off}$ of 0.5× of the $k_{off}$ of cetuximab or of hu225, a $k_{off}$ of 0.75× of the $k_{off}$ of cetuximab or of hu225, a $k_{off}$ of 1× of the $k_{off}$ of cetuximab or of hu225, a $k_{off}$ of 1.25× of the $k_{off}$ of cetuximab or of hu225, a $k_{off}$ of 1.5× of the $k_{off}$ of cetuximab or of hu225, a $k_{off}$ of 1.75× of the $k_{off}$ of cetuximab or of hu225, a $k_{off}$ of 2× of the $k_{off}$ of cetuximab or of hu225, a $k_{off}$ of 2.25× of the $k_{off}$ of cetuximab or of hu225, a $k_{off}$ of 2.5× of the $k_{off}$ of cetuximab or of hu225, a $k_{off}$ of 3× of the $k_{off}$ of cetuximab or of hu225, or a $k_{off}$ ranging between any pair of the foregoing values, e.g., a $k_{off}$ of 0.01× to 1.25× of the $k_{off}$ of cetuximab or of hu225, a $k_{off}$ of 0.05× to 2.5× of the $k_{off}$ of cetuximab or of hu225, or a $k_{off}$ of 0.006× to 0.1× of the $k_{off}$ of cetuximab or of hu225, etc.

In other embodiments, an anti-EGFR antibody of the disclosure binds to EGFR with a $K_A$ ($k_{on}/k_{off}$) ranging from about 0.25× to about 1000× of the $K_A$ of cetuximab or of hu225, for example, a $K_A$ of 0.5× of the $K_A$ of cetuximab or of hu225, a $K_A$ of 0.75 of the $K_A$ of cetuximab or of hu225, a $K_A$ of 1× of the $K_A$ of cetuximab or of hu225, a $K_A$ of 2× of the $K_A$ of cetuximab or of hu225, a $K_A$ of 3× of the $K_A$ of cetuximab or of hu225, a $K_A$ of 4× of the $K_A$ of cetuximab or of hu225, a $K_A$ of 5× of the $K_A$ of cetuximab or of hu225, a $K_A$ of 10× of the $K_A$ of cetuximab or of hu225, a $K_A$ of 15× of the $K_A$ of cetuximab or of hu225, a $K_A$ of 20× of the $K_A$ of cetuximab or of hu225, a $K_A$ of 30× of the $K_A$ of cetuximab or of hu225, a $K_A$ of 40× of the $K_A$ of cetuximab or of hu225, a $K_A$ of 50× of the $K_A$ of cetuximab or of hu225, a $K_A$ of 75× of the $K_A$ of cetuximab or of hu225, a $K_A$ of 100× of the $K_A$ of cetuximab or of hu225, a $K_A$ of 200× of the $K_A$ of cetuximab or of hu225, a $K_A$ of 250× of the $K_A$ of cetuximab or of hu225, a $K_A$ of 300× of the $K_A$ of cetuximab or of hu225, a $K_A$ of 350× of the $K_A$ of cetuximab or of hu225, a $K_A$ of 400× of the $K_A$ of cetuximab or of hu225, a $K_A$ of 500× of the $K_A$ of cetuximab or of hu225, a $K_A$ of 750× of the $K_A$ of cetuximab or of hu225, a $K_A$ of 100× of the $K_A$ of cetuximab or of hu225, or a $K_A$ ranging between any pair of the foregoing values, e.g., a $K_A$ of 0.75× to 100× of the $K_A$ of cetuximab or of hu225, a $K_A$ of 10× to 50× of the $K_A$ of cetuximab or of hu225, or a $K_A$ of 5× to 50× of the $K_A$ of cetuximab or of hu225, etc.

In still other embodiments, an anti-EGFR antibody of the disclosure binds to EGFR with a $K_D$ ($k_{off}/k_{on}$) ranging from about 0.001× to 10× of the $K_D$ of cetuximab or of hu225, or for example, a $K_D$ of 0.001× of the $K_D$ of cetuximab or of hu225, a $K_D$ of 0.002× of the $K_D$ of cetuximab or of hu225, a $K_D$ of 0.003× of the $K_D$ of cetuximab or of hu225, a $K_D$ of 0.004× of the $K_D$ of cetuximab or of hu225, a $K_D$ of 0.005× of the $K_D$ of cetuximab or of hu225, a $K_D$ of 0.0075× of the $K_D$ of cetuximab or of hu225, a $K_D$ of 0.01× of the $K_D$ of cetuximab or of hu225, a $K_D$ of 0.025× of the $K_D$ of cetuximab or of hu225, a $K_D$ of 0.05× of the $K_D$ of cetuximab or of hu225, a $K_D$ of 0.075× of the $K_D$ of cetuximab or of hu225, a $K_D$ of 0.1× of the $K_D$ of cetuximab or of hu225, a $K_D$ of 0.2× of the $K_D$ of cetuximab or of hu225, a $K_D$ of 0.3× of the $K_D$ of cetuximab or of hu225, a $K_D$ of 0.4× of the $K_D$ of cetuximab or of hu225, a $K_D$ of 0.5× of the $K_D$ of cetuximab or of hu225, a $K_D$ of 0.75× of the $K_D$ of cetuximab a $K_D$ of 1× of the $K_D$ of cetuximab or of hu225, a $K_D$ of 1.5× of the $K_D$ of cetuximab or of hu225, a $K_D$ of 2× of the $K_D$ of cetuximab or of hu225, a $K_D$ of 3× of the $K_D$ of cetuximab or of hu225, a $K_D$ of 4× of the $K_D$ of cetuximab or of hu225, a $K_D$ of 5× of the $K_D$ of cetuximab or of hu225, a $K_D$ of 7.5× of the $K_D$ of cetuximab or of hu225, a $K_D$ of 10× of the $K_D$ of cetuximab or of hu225, or a $K_D$ ranging between any pair of the foregoing values, e.g., a $K_D$ of 0.001× o 0.5× of the $K_D$ of cetuximab or of hu225, a $K_D$ of 0.1× to 4× of the $K_D$ of cetuximab or of hu225, a $K_D$ of 0.05 to 1× of the $K_D$ of cetuximab or of hu225, etc.

In certain embodiments, an anti-EGFR antibody of the disclosure binds to EGFR and inhibits the binding of EGFR to EGF or neutralizes the activity of EGFR at a $IC_{50}$ value ranging from about 0.001× to 10× of the $IC_{50}$ of cetuximab or of hu225, for example, at an $IC_{50}$ value of 0.01× of the $IC_{50}$ of cetuximab or of hu225, at an $IC_{50}$ of 0.05× of the $IC_{50}$ of cetuximab or of hu225, at an $IC_{50}$ of 0.1× of the $IC_{50}$ of cetuximab or of hu225, at an $IC_{50}$ of 0.2× of the $IC_{50}$ of cetuximab or of hu225, at an $IC_{50}$ of 0.3× of the $IC_{50}$ of cetuximab or of hu225, at an $IC_{50}$ of 0.4× of the $IC_{50}$ of cetuximab or of hu225, at an $IC_{50}$ of 0.5× of the $IC_{50}$ of cetuximab or of hu225, at an $IC_{50}$ of 0.6× of the $IC_{50}$ of cetuximab or of hu225, at an $IC_{50}$ of 0.7× of the $IC_{50}$ of cetuximab or of hu225, at an $IC_{50}$ of 0.8× of the $IC_{50}$ of cetuximab or of hu225, at an $IC_{50}$ of 0.9× of the $IC_{50}$ of cetuximab or of hu225, at an $IC_{50}$ of 1× of the $IC_{50}$ of cetuximab or of hu225, at an $IC_{50}$ of 1.5× of the $IC_{50}$ of cetuximab or of hu225, at an $IC_{50}$ of 2× of the $IC_{50}$ of cetuximab or of hu225, at an $IC_{50}$ of 3× of the $IC_{50}$ of cetuximab or of hu225, at an $IC_{50}$ of 4× of the $IC_{50}$ of cetuximab or of hu225, at an $IC_{50}$ of 5× of the $IC_{50}$ of cetuximab or of hu225, at an $IC_{50}$ of 7.5× of the $IC_{50}$ of cetuximab or of hu225, at an $IC_{50}$ of 10× of the $IC_{50}$ of cetuximab or of hu225, or an $IC_{50}$ ranging between any pair of the foregoing values, e.g., an $IC_{50}$ of 0.01 to 0.2 of the $IC_{50}$ of cetuximab or of hu225, an $IC_{50}$ of 0.1× to 1.5× of the $IC_{50}$ of cetuximab or of hu225, an $IC_{50}$ of 0.2× to 2× of the $IC_{50}$ of cetuximab or of hu225, etc. In certain embodiments, a single CDR substitution can result in the foregoing differences in $IC_{50}$ as compared to cetuximab or hu225, whereas an anti-EGFR antibody of the disclosure can comprise such substitution and up to 16 additional CDR substitutions as compared to cetuximab or hu225.

6.5 Antibody Conjugates

The anti-EGFR antibodies of the disclosure include antibody conjugates that are modified, e.g., by the covalent attachment of any type of molecule to the antibody, such that covalent attachment does not interfere with binding to EGFR.

In certain aspects, an anti-EGFR antibody of the disclosure can be conjugated to an effector moiety or a label. The term "effector moiety" as used herein includes, for example, antineoplastic agents, drugs, toxins, biologically active proteins, for example, enzymes, other antibody or antibody fragments, synthetic or naturally occurring polymers, nucleic acids (e.g., DNA and RNA), radionuclides, particularly radioiodide, radioisotopes, chelated metals, nanoparticles and reporter groups such as fluorescent compounds or compounds which can be detected by NMR or ESR spectroscopy.

In one example, anti-EGFR antibodies can be conjugated to an effector moiety, such as a cytotoxic agent, a radionuclide or drug moiety to modify a given biological response. The effector moiety can be a protein or polypeptide, such as, for example, and without limitation, a toxin (such as abrin, ricin A, *Pseudomonas* exotoxin, or Diphtheria toxin), a signaling molecule (such as α-interferon, β-interferon, nerve growth factor, platelet derived growth factor or tissue plasminogen activator), a thrombotic agent or an anti-angiogenic agent (e.g., angiostatin or endostatin) or a biological response modifier such as a cytokine or growth factor (e.g., interleukin-1 (IL-1), interleukin-2 (IL-2), interleukin-6 (IL-6), granulocyte macrophage colony stimulating factor (GM-CSF), granulocyte colony stimulating factor (G-CSF), or nerve growth factor (NGF)).

In another example, the effector moieties can be cytotoxins or cytotoxic agents. Examples of cytotoxins and cytotoxic agents include taxol, cytochalasin B, gramicidin D, ethidium bromide, emetine, mitomycin, etoposide, tenoposide, vincristine, vinblastine, colchicin, doxorubicin, daunorabicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector moieties also include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C5 and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, anthramycin (AMC), calicheamicins or duocarmycins), and anti-mitotic agents (e.g., vincristine and vinblastine).

Other effector moieties can include radionuclides such as, but not limited to, $^{111}$In and $^{90}$Y, Lu$^{177}$, Bismuth$^{213}$, Californium$^{252}$, Iridium$^{192}$ and Tungsten$^{188}$/Rhenium$^{188}$ and drugs such as, but not limited to, alkylphosphocholines, topoisomerase I inhibitors, taxoids and suramin.

Techniques for conjugating such effector moieties to antibodies are well known in the art (see, e.g., Hellstrom et al., Controlled Drug Delivery, 2nd Ed., at pages 623-53 (Robinson et al., eds., 1987)); Thorpe et al., 1982, Immunol. Rev. 62:119-58 and Dubowchik et al., 1999, Pharmacology and Therapeutics 83:67-123).

In one example, the anti-EGFR antibody or fragment thereof is fused via a covalent bond (e.g., a peptide bond), through the antibody's N-terminus or C-terminus or internally, to an amino acid sequence of another protein (or portion thereof; for example, at least a 10, 20 or 50 amino acid portion of the protein). The antibody, or fragment thereof, can linked to the other protein at the N-terminus of the constant domain of the antibody. Recombinant DNA procedures can be used to create such fusions, for example, as described in WO 86/01533 and EP0392745. In another example, the effector molecule can increase half-life in vivo, and/or enhance the delivery of an antibody across an epithelial barrier to the immune system. Examples of suitable effector molecules of this type include polymers, albumin, albumin binding proteins or albumin binding compounds such as those described in WO 2005/117984.

In certain aspects, an anti-EGFR antibody is conjugated to a small molecule toxin. In certain exemplary embodiments, an anti-EGFR antibody of the disclosure is conjugated to a dolostatin or a dolastatin peptidic analogs or derivatives, e.g., an auristatin (U.S. Pat. Nos. 5,635,483 and 5,780,588). The dolastatin or auristatin drug moiety may be attached to the antibody through its N (amino) terminus, C (carboxyl) terminus or internally (WO 02/088172). Exemplary auristatin embodiments include the N-terminus linked monomethylauristatin drug moieties DE and DF, as disclosed in U.S. Pat. No. 7,498,298, which is hereby incorporated by reference in its entirety (disclosing, e.g., linkers and methods of preparing monomethylvaline compounds such as MMAE and MMAF conjugated to linkers).

In other exemplary embodiments, small molecule toxins include but are not limited to calicheamicin, maytansine (U.S. Pat. No. 5,208,020), trichothene, and CC1065. In one embodiment of the disclosure, the antibody is conjugated to one or more maytansine molecules (e.g., about 1 to about 10 maytansine molecules per antibody molecule). Maytansine may, for example, be converted to May-SS-Me which may be reduced to May-SH3 and reacted with an antibody (Chari et al., 1992, Cancer Research 52: 127-131) to generate a maytansinoid-antibody or maytansinoid-Fc fusion conjugate. Structural analogues of calicheamicin that can also be used include but are not limited to $\gamma_1^1$, $\gamma_3^1$, $\gamma_3^1$-N-acetyl-$\gamma_1^1$, PSAG, and $\theta_1^1$ (Hinman et al., 1993, Cancer Research 53:3336-3342; Lode et at, 1998, Cancer Research 58:2925-2928; U.S. Pat. No. 5,714,586; U.S. Pat. No. 5,712,374; U.S. Pat. No. 5,264,586; U.S. Pat. No. 5,773,001).

Antibodies of the disclosure can also be conjugated to liposomes for targeted delivery (See, e.g., Park et al., 1997, Adv. Pharmacol. 40:399-435; Marty & Schwendener, 2004, Methods in Molecular Medicine 109:389-401).

In one example, antibodies of the present disclosure can be attached to poly(ethyleneglycol) (PEG) moieties. In one particular example, the antibody is an antibody fragment and the PEG moieties can be attached through any available amino acid side-chain or terminal amino acid functional group located in the antibody fragment, for example, any free amino, imino, thiol, hydroxyl or carboxyl group. Such amino acids can occur naturally in the antibody fragment or can be engineered into the fragment using recombinant DNA methods. See for example, U.S. Pat. No. 5,219,996. Multiple sites can be used to attach two or more PEG molecules. PEG moieties can be covalently linked through a thiol group of at least one cysteine residue located in the antibody fragment. Where a thiol group is used as the point of attachment, appropriately activated effector moieties, for example, thiol selective derivatives such as maleimides and cysteine derivatives, can be used.

In a specific example, an anti-EGFR antibody conjugate is a modified Fab' fragment which is PEGylated, i.e., has PEG (poly(ethyleneglycol)) covalently attached thereto, e.g., according to the method disclosed in EP0948544. See also Poly(ethyleneglycol) Chemistry, Biotechnical and Biomedical Applications, (J. Milton Harris (ed.), Plenum Press, New York, 1992); Poly(ethyleneglycol) Chemistry and Biological Applications, (J. Milton Harris and S. Zalipsky, eds., American Chemical Society, Washington D.C., 1997); and Bioconjugation Protein Coupling Techniques for the Biomedical Sciences, (M. Aslam and A. Dent, eds., Grove Publishers, New York, 1998); and Chapman, 2002, Advanced Drug Delivery Reviews 54:531-545. PEG can be attached to a cysteine in the hinge region. In one example, a PEG-modified Fab' fragment has a maleimide group covalently linked to a single thiol group in a modified hinge region. A lysine residue can be covalently linked to the maleimide group and to each of the amine groups on the lysine residue can be attached a methoxypoly(ethyleneglycol) polymer having a molecular weight of approximately 20,000 Da. The total molecular weight of the PEG attached to the Fab' fragment can therefore be approximately 40,000 Da.

The word "label" when used herein refers to a detectable compound or composition which can be conjugated directly or indirectly to an anti-EGFR antibody of the disclosure. The label can itself be detectable (e.g., radioisotope labels or fluorescent labels) or, in the case of an enzymatic label, can catalyze chemical alteration of a substrate compound or composition which is detectable. Useful fluorescent moieties include, but are not limited to, fluorescein, fluorescein isothiocyanate, rhodamine, 5-dimethylamine-1-napthalenesulfonyl chloride, phycoerythrin and the like. Useful enzymatic labels include, but are not limited to, alkaline phosphatase, horseradish peroxidase, glucose oxidase and the like.

Additional anti-EGFR antibody conjugates that are useful for, inter alis, diagnostic purposes, are described in Section 6.5 below.

6.6 Diagnostic Uses of Anti-EGFR Antibodies

The anti-EGFR antibodies of the disclosure, including those antibodies that have been modified, e.g., by biotinylation, horseradish peroxidase, or any other detectable moiety (including those described in Section 6.4), can be advantageously used for diagnostic purposes.

In particular, the anti-EGFR antibodies can be used, for example, but not limited to, to purify or detect EGFR, including both in vitro and in vivo diagnostic methods. For example, the antibodies have use in immunoassays for qualitatively and quantitatively measuring levels of EGFR in biological samples. See, e.g., Harlow et al., Antibodies: A Laboratory Manual, Second Edition (Cold Spring Harbor Laboratory Press, 1988), which is incorporated by reference herein in its entirety.

The present disclosure further encompasses anti-EGFR antibodies or fragments thereof conjugated to a diagnostic agent. The antibodies can be used diagnostically, for example, to detect expression of a target of interest in specific cells, tissues, or serum; or to monitor the development or progression of an immunologic response as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody (or fragment thereof) or indirectly, through an intermediate (such as, for example, a linker known in the art) using techniques known in the art. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, acetylcholinesterase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

The disclosure provides for the detection of expression of EGFR, comprising contacting a biological sample (cells, tissue, or body fluid of an individual) using one or more anti-EGFR antibodies of the disclosure (optionally conjugated to detectable moiety), and detecting whether or not the sample is positive for EGFR expression, or whether the sample has altered (e.g., reduced or increased) expression as compared to a control sample.

Diseases that can be diagnosed using the present methods include, but are not limited to, the diseases described herein. In certain embodiments, the tissue or body fluid is peripheral blood, peripheral blood leukocytes, biopsy tissues such as breast or lymph node biopsies, and tissue.

6.7 Therapeutic Methods Using Anti-EGFR Antibodies 6.7.1 Clinical Benefits

The anti-EGFR antibodies of the disclosure can be used to treat various neoplasms. In certain aspects, the anti-EGFR antibodies of the disclosure can be used to treat Menetrier's disease.

The antibodies of the disclosure are useful in the treatment of tumors, including cancers and benign tumors. More particularly, cancers that are amenable to treatment by the antibodies of the disclosure include those that over express EGFR. In certain embodiments, cancers that are amenable to treatment by the antibodies disclosed herein include epithelial cell cancers. In particular embodiments, cancers that are amenable to treatment by anti-EGFR antibodies of the present disclosure include breast cancer, ovarian cancer, lung cancer, colorectal cancer, anal cancer, prostate cancer, kidney cancer, bladder cancer, head and neck cancer, ovarian cancer, pancreatic cancer, skin cancer, oral cancer, esophageal cancer, vaginal cancer, cervical cancer, cancer of the spleen, testicular cancer, and cancer of the thymus. In some particular embodiments, the anti-EGFR antibodies of the disclosure are used to treat head and neck cancer in a human patient. In other embodiments, the anti-EGFR antibodies of the disclosure are used to treat colorectal cancer in a human patient.

Accordingly, the present disclosure provides methods of treating any of the foregoing diseases in a patient in need thereof, comprising: administering to the patient an anti-EGFR antibody of the disclosure. Optionally, said administration is repeated, e.g., after one day, two days, three days, five days, one week, two weeks, three weeks, one month, five weeks, six weeks, seven weeks, eight weeks, two months or three months. The repeated administration can be at the same dose or at a different dose. The administration can be repeated once, twice, three times, four times, five times, six times, seven times, eight times, nine times, ten times, or more. For example, according to certain dosage regimens a patient receives anti-EGFR therapy for a prolonged period of time, e.g., 6 months, 1 year or more. The amount of anti-EGFR antibody administered to the patient is in certain embodiments a therapeutically effective amount. As used herein, a "therapeutically effective" amount of EGFR antibody can be administered as a single dose or over the course of a therapeutic regimen, e.g., over the course of a week, two weeks, three weeks, one month, three months, six months, one year, or longer. Exemplary therapeutic regimens are described in Section 6.9 below.

According to the present disclosure, treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom the anti-EGFR antibody of the disclosure is administered is preferably a mammal such as a non-primate (e.g., cow, pig, horse, cat, dog, rat, etc.) or a primate (e.g., monkey or human). In certain embodiments, the subject or patient is a human. In certain aspects, the human is an adult patient. In other aspects, the human is a pediatric patient.

6.8 Pharmaceutical Compositions and Routes of Administration

Compositions comprising an anti-EGFR antibody of the disclosure and, optionally one or more additional therapeutic agents, such as the combination therapeutic agents described in Section 6.8 below, are provided herein. The compositions will usually be supplied as part of a sterile, pharmaceutical composition that will normally include a pharmaceutically acceptable carrier. This composition can be in any suitable form (depending upon the desired method of administering it to a patient).

The anti-EGFR antibodies of the disclosure can be administered to a patient by a variety of routes such as orally, transdermally, subcutaneously, intranasally, intravenously, intramuscularly, intraocularly, topically, intrathecally and intracerebroventricularly. The most suitable route for administration in any given case will depend on the particular antibody, the subject, and the nature and severity of the disease and the physical condition of the subject.

For treatment of indications described herein, the effective dose of an anti-EGFR antibody of the disclosure can range from about 0.1 to about 500 mg/m$^2$ (i.e., from about 0.003 to about 13 mg/kg for an average adult human having a body weight of 60 kg and a body surface area of 1.6 m$^2$) per single (e.g., bolus) administration, multiple administrations or continuous administration, or to achieve a serum concentration of 0.01-5000 µg/mL serum concentration per single (e.g., bolus) administration, multiple administrations or continuous administration, or any effective range or value therein depending on the condition being treated, the route of administration and the age, weight and condition of the subject. In certain embodiments, e.g., for the treatment of cancer, each dose can range from about 0.5 mg to about 250 mg per meter$^2$ of body surface area, for example, from about 1.0 mg to about 100 mg per meter$^2$ of body surface area, for example, from about 5 mg to about 50 mg per meter$^2$ of body surface area. The antibody can be formulated as an aqueous solution and administered by subcutaneous injection.

Pharmaceutical compositions can be conveniently presented in unit dose forms containing a predetermined amount of an anti-EGFR antibody of the disclosure per dose. Such a unit can contain for example, but without limitation 0.1 mg to 5 g, for example, 1 mg to 1 g, or 10 to 50 mg. Pharmaceutically acceptable carriers for use in the disclosure can take a wide variety of forms depending, e.g., on the condition to be treated or route of administration.

Therapeutic formulations of the anti-EGFR antibodies of the disclosure can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range that approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acidmonosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polhydric sugar alcohols, for example, trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Nonionic surfactants can be present in a range of about 0.05 mg/mL to about 1.0 mg/mL, for example, about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a combination therapeutic agent in addition to the anti-EGFR antibody of the disclosure. Examples of suitable combination therapeutic agents are provided in Section 6.8 below.

The dosing schedule for subcutaneous administration can vary from once every six months to daily depending on a number of clinical factors, including the type of disease, severity of disease, and the patient's sensitivity to the anti-EGFR antibody.

The dosage of an anti-EGFR antibody of the disclosure to be administered will vary according to the particular antibody, the type of disease, the subject, and the severity of the disease, the physical condition of the subject, the therapeutic regimen (e.g., whether a combination therapeutic agent is used), and the selected route of administration; the appropriate dosage can be readily determined by a person skilled in the art.

It will be recognized by one of skill in the art that the optimal quantity and spacing of individual dosages of an anti-EGFR antibody of the disclosure will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop, the amount and/or frequency of the dosage can be altered or reduced, in accordance with normal clinical practice.

6.9 Combination Therapy

Described below are combinatorial methods in which the anti-EGFR antibodies of the disclosure can be utilized. The combinatorial methods of the disclosure involve the administration of at least two agents to a patient, the first of which is an anti-EGFR antibody of the disclosure, and the second of which is a combination therapeutic agent. The anti-EGFR antibody and the combination therapeutic agent can be administered simultaneously, sequentially or separately.

The combinatorial therapy methods of the present disclosure can result in a greater than additive effect, providing therapeutic benefits where neither the anti-EGFR antibody or combination therapeutic agent administered in an amount that is alone therapeutically effective.

In the present methods, the anti-EGFR antibody of the disclosure and the combination therapeutic agent can be administered concurrently, either simultaneously or successively. As used herein, the anti-EGFR antibody of the disclosure and the combination therapeutic agent are said to be administered successively if they are administered to the patient on the same day, for example, during the same patient visit. Successive administration can occur 1, 2, 3, 4, 5, 6, 7 or 8 hours apart. In contrast, the anti-EGFR antibody of the disclosure and the combination therapeutic agent are said to be administered separately if they are administered to the patient on the different days, for example, the anti-EGFR antibody of the disclosure and the combination therapeutic agent can be administered at a 1-day, 2-day or 3-day, one-week, 2-week or monthly intervals. In the methods of the present disclosure, administration of the anti-EGFR antibody of the disclosure can precede or follow administration of the combination therapeutic agent.

As a non-limiting example, the anti-EGFR antibody of the disclosure and combination therapeutic agent can be administered concurrently for a period of time, followed by a second period of time in which the administration of the anti-EGFR antibody of the disclosure and the combination therapeutic agent is alternated.

Because of the potentially synergistic effects of administering an anti-EGFR antibody of the disclosure and a combination therapeutic agent, such agents can be administered in amounts that, if one or both of the agents is administered alone, is/are not therapeutically effective.

In certain aspects, the combination therapeutic agent is a chemotherapeutic agent, an anti-angiogenic agent, an anti-rheumatic drug, an anti-inflammatory agent, a radiotherapeutic, an immunosuppressive agent, or a cytotoxic drug.

It is contemplated that when used to treat various diseases, the anti-EGFR antibodies of the disclosure can be combined with other therapeutic agents suitable for the same or similar diseases. When used for treating cancer, antibodies of the present disclosure may be used in combination with conventional cancer therapies, such as surgery, radiotherapy, chemotherapy or combinations thereof.

In some other aspects, other therapeutic agents useful for combination tumor therapy with the antibody of the disclosure include antagonists, e.g., antibodies, of other factors that are involved in tumor growth, such as HER2, HER3, HER4, VEGF, or TNF-α.

Sometimes, for treatment of cancers it may be beneficial to also administer one or more cytokines to the patient. In a preferred embodiment, the anti-EGFR antibody is co-administered with a growth inhibitory agent.

Suitable dosages for the growth inhibitory agent are those presently used and may be lowered due to the combined action (synergy) of the growth inhibitory agent and anti-EGFR antibody.

For treatment of cancers, anti-inflammatory agents can suitably be used in combination with the anti-EGFR antibodies of the disclosure. Anti-inflammatory agents include, but are not limited to, acetaminophen, diphenhydramine, meperidine, dexamethasone, pentasa, mesalazine, asacol, codeine phosphate, benorylate, fenbufen, naprosyn, diclofenac, etodolac and indomethacin, aspirin and ibuprofen.

For treatment of cancers, chemotherapeutic agents can suitably be used in combination with the anti-EGFR antibodies of the disclosure. Chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, an anti-α5β1 integrin antibody, alkylating agents, allopurinol sodium, altretamine, amifostine, anastrozole, anthramycin (AMC)), anti-mitotic agents, cisdichlorodiamine platinum (II) (DDP) cisplatin, diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, eolociximab, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, Ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Any anti-angiogenic agent can be used in conjunction with the anti-EGFR antibodies of the disclosure, including those listed by Carmeliet and Jain, 2000, Nature 407:249-257. In certain embodiments, the anti-angiogenic agent is a VEGF antagonist or another VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternatively, or in addition, an anti-VEGF antibody may be co-administered to the patient.

In certain embodiments, e.g., to treat Menetrier's disease, an anti-EGFR antibody can be used in conjunction with a TNF-α antagonist. Examples of such TNF-α antagonists include, but are not limited to, soluble TNF-α receptors; etanercept (ENBREL™; Immunex) or a fragment, derivative or analog thereof; infliximab (REMICADE®; Centacor) or a derivative, analog or antigen-binding fragment thereof; IL-10, which is known to block TNF-α production via interferon-γ-activated macrophages (Oswald et al., 1992, Proc. Natl. Acad. Sci. USA 89:8676-8680), TNFR-IgG (Ashkenazi et al., 1991, Proc. Natl. Acad. Sci. USA 88:10535-10539); the murine product TBP-1 (Serono/Yeda); the vaccine CytoTAb (Protherics); antisense molecule 104838 (ISIS); the peptide RDP-58 (SangStat); thalidomide (Celgene); CDC-801 (Celgene); DPC-333 (Dupont); VX-745 (Vertex); AGIX-4207 (AtheroGenics); ITF-2357 (Italfarmaco); NPI-13021-31 (Nereus); SCIO-469 (Scios); TACE targeter (Immunix/AHP); CLX-120500 (Calyx); Thiazolopyrim (Dynavax); auranofin (Ridaura) (SmithKline Beecham Pharmaceuticals); quinacrine (mepacrine dichlorohydrate); tenidap (Enablex); Melanin (Large Scale Biological); and anti-p38 MAPK agents by Uriach. In various embodiments, the TNF-α antagonist is an antibody.

In some aspects, an anti-EGFR antibody can be used in conjunction with a small molecule protein tyrosine kinase (PTK) inhibitor. In some embodiments, the PTK inhibitor is specific for the EGFR tyrosine kinase. In other embodiments, the PTK inhibitor binds to more than one of the HER family of tyrosine kinases (e.g., EGFR, HER2 and/or HER4). In still other embodiments, the PTK inhibitors bind to and inhibit the tyrosine kinases of one or more proteins that interact with or are regulated by one or more HER family members, e.g., proteins involved in one or more signaling cascades that originate with one or more HER family members. In other embodiments, protein tyrosine kinase inhibitors useful in the compositions and methods of the invention include PTK inhibitors that do not bind selectively to the HER family of receptor tyrosine kinases, but also bind to the tyrosine kinase domains of other families of proteins such as VEGFR, PDGFR, and/or Raf.

In some embodiments, the tyrosine kinase is a receptor tyrosine kinase, i.e., is an intra-cellular domain of a larger protein that has an extra-cellular ligand binding domain and is activated by the binding of one or more ligands. In certain embodiments, the protein tyrosine kinase is a non-receptor tyrosine kinase. PTK inhibitors for use in the methods of the present disclosure include, but are not limited to, PTK inhibitors useful in the methods and compositions of the invention include, but are not limited to, gefitinib (ZD-1839, Iressa®), erlotinib (OSI-1774, Tarceva™), canertinib (CI-1033), vandetanib (ZD6474, Zactima®), tyrphostin AG-825 (CAS 149092-50-2), lapatinib (GW-572016), sorafenib (BAY43-9006), AG-494 (CAS 133550-35-3), RG-13022 (CAS 149286-90-8), RG-14620 (CAS 136831-49-7), BIBW 2992 (Tovok), tyrphostin 9 (CAS 136831-49-7), tyrphostin 23 (CAS 118409-57-7), tyrphostin 25 (CAS 118409-58-8), tyrphostin 46 (CAS 122520-85-8), tyrphostin 47 (CAS 122520-86-9), tyrphostin 53 (CAS 122520-90-5), butein (1-(2,4-dihydroxyphenyl)-3-(3,4-dihydroxyphenyl)-2-propen-1-one 2',3,4,4'-Tetrahydroxychalcone; CAS 487-52-5), curcumin ((E,E)-1,7-bis(4-Hydroxy-3-methoxyphenyl)-1,6-heptadiene-3,5-dione; CAS 458-37-7), N4-(1-Benzyl-1H-indazol-5-yl)-N6,N6-dimethyl-pyrido-[3,4-d]-pyrimidine-4,6-diamine (202272-68-2), AG-1478, AG-879, Cyclopropanecarboxylic acid-(3-(6-(3-trifluoromethyl-phenylamino)-pyrimidin-4-ylamino)-phenyl)-amide (CAS 879127-07-8), N8-(3-Chloro-4-fluorophenyl)-N2-(1-methylpiperidin-4-yl)-pyrimido[5,4-d]pyrimidine-2,8-diamine, 2HCl (CAS 196612-93-8), 4-(4-Benzyloxyanilino)-6,7-dimethoxyquinazoline (CAS 179248-61-4), N-(4-((3-Chloro-4-fluorophenyl) amino)pyrido[3,4-d]pyrimidin-6-yl)-2-butynamide (CAS 881001-19-0), EKB-569, HKI-272, and HKI-357.

In a specific embodiment, an anti-EGFR antibody of the disclosure is used in combination with radiation therapy. This combination is suitable for, inter alia, initial treatment of patients with locally or regionally advanced squamous cell carcinoma of the head and neck.

In another specific embodiment, an anti-EGFR antibody of the disclosure is used as a single agent following unsuccessful platinum-based therapy. This regimen is suitable for, inter alia, treatment of patients with recurrent or metastatic squamous cell carcinoma of the head and neck.

In yet another specific embodiment, an anti-EGFR antibody of the disclosure is used as a single agent following unsuccessful irinotecan-based and oxaliplatin-based therapies. This regimen is suitable for, inter alia, treatment of patients with EGFR-over expressing metastatic colorectal cancer. This regimen is also suitable for, inter alia, treatment of patients with EGFR-over expressing metastatic colorectal cancer who are intolerant to irinotecan-based therapies.

In another specific embodiment, the anti-EGFR antibody of the disclosure is used in combination with irinotecan. This combination is suitable for, inter alia, treatment of patients with EGFR-over expressing metastatic colorectal carcinoma who are refractory to irinotecan-based chemotherapy.

6.10 Therapeutic Regimens

The present disclosure provides therapeutic regimens involving the administration of the anti-EGFR antibodies of the disclosure. The therapeutic regimen will vary depending on the patient's age, weight, and disease condition. The therapeutic regimen can continue for 2 weeks to indefinitely. In specific embodiments, the therapeutic regimen is continued for 2 weeks to 6 months, from 3 months to 5 years, from 6 months to 1 or 2 years, from 8 months to 18 months, or the like. The therapeutic regimen can be a non-variable dose regimen or a multiple-variable dose regimen.

For the dosage exemplary regimens described below, the anti-EGFR antibody can be administered as a sterile, preservative-free solution for subcutaneous administration.

For treatment of locally or regionally advanced squamous cell carcinoma of the head and neck in combination with radiation therapy, an anti-EGFR antibody of the disclosure can be administered intravenously one week before commencement of radiation therapy at an initial dose of 0.1 to 500 mg/m$^2$ (e.g., 0.003 to 13.3 mg/kg for an average adult human weighing 60 kg and having a body surface area of 1.6 m$^2$). In specific embodiments, the initial dose is 0.1-400 mg/m$^2$, 0.25-300 mg/m$^2$, 0.5-250 mg/m$^2$, 1-200 mg/m$^2$, 1-150 mg/m$^2$, 2-100 mg/m$^2$, 5-75 mg/m$^2$, 8-50 mg/m$^2$, 10-350 mg/m$^2$, 15-300 mg/m$^2$, 20-250 mg/m$^2$, 30-200 mg/m$^2$ or 40-100 mg/m$^2$. Following the initial dose, an anti-EGFR antibody of the disclosure can be administered intravenously weekly for 6-7 weeks (i.e., the duration of radiation therapy) at a dose of 0.1 to 300 mg/m$^2$ (i.e., 0.003 to 8 mg/kg for an average human weighing 60 kg and having a body surface area of 1.6 m$^2$). In specific embodiments, the subsequently weekly dose is 0.1 to 250 mg/m$^2$, such as 0.5-200 mg/m$^2$, such as 1-150 mg/m$^2$, such as 2-100 mg/m$^2$, such as 2.5-100 mg/m$^2$, such as 5-75 mg/m$^2$, such as 10-50 mg/m$^2$, such as 15-150 mg/m$^2$, such as 20-100 mg/m$^2$, such as 30-125 mg/m$^2$, such as 40-150 mg/m$^2$, or such as 50-175 mg/m$^2$.

For treatment of recurrent or metastatic squamous cell carcinoma of the head and neck following unsuccessful treatment with prior platinum-based therapy, an anti-EGFR antibody of the disclosure is administered intravenously as a single agent at an initial dose of 0.1 to 500 mg/m$^2$ (e.g., 0.003 to 13.3 mg/kg for an average adult human weighing 60 kg and having a body surface area of 1.6 m$^2$). In specific embodiments, the initial dose is 0.1-400 mg/m$^2$, 0.25-300 mg/m$^2$, 0.5-250 mg/m$^2$, 1-200 mg/m$^2$, 1-150 mg/m$^2$, 2-100 mg/m$^2$, 5-75 mg/m$^2$, 8-50 mg/m$^2$, 10-350 mg/m$^2$, 15-300 mg/m$^2$, 20-250 mg/m$^2$, 30-200 mg/m$^2$ or 40-100 mg/m$^2$. Following the initial dose, an anti-EGFR antibody of the disclosure is administered intravenously once weekly at a dose of 0.1 to 300 mg/m$^2$ (i.e., 0.003 to 8 mg/kg for an average adult human weighing 60 kg and having a body surface area of 1.6 m$^2$). In specific embodiments, the subsequently weekly dose is 0.1 to 250 mg/m$^2$, such as 0.5-200 mg/m$^2$, such as 1-150 mg/m$^2$, such as 2-100 mg/m$^2$, such as 2.5-100 mg/m$^2$, such as 5-75 mg/m$^2$, such as 10-50 mg/m$^2$, such as 15-150 mg/m$^2$, such as 20-100 mg/m$^2$, such as 30-125 mg/m$^2$, such as 40-150 mg/m$^2$, such as 50-175 mg/m$^2$.

For treatment of EGFR-expressing colorectal cancer following unsuccessful treatment with both irinotecan-base and oxaliplatin-based therapies or in patients who are intolerant to irinotecan-based regiments, an anti-EGFR antibody of the disclosure is administered intravenously as a single agent at an initial dose of 0.1 to 500 mg/m$^2$ (e.g., 0.003 to 13.3 mg/kg for an average adult human weighing 60 kg and having a body surface area of 1.6 m$^2$). In specific embodiments, the initial dose is 0.1-400 mg/m$^2$, 0.25-300 mg/m$^2$, 0.5-250 mg/m$^2$, 1-200 mg/m$^2$, 1-150 mg/m$^2$, 2-100 mg/m$^2$, 5-75 mg/m$^2$, 8-50 mg/m$^2$, 10-350 mg/m$^2$, 15-300 mg/m$^2$, 20-250 mg/m$^2$, 30-200 mg/m$^2$ or 40-100 mg/m$^2$. Following the initial dose, an anti-EGFR antibody of the disclosure is administered intravenously once weekly at a dose of 0.1 to 300 mg/m2 (i.e., 0.003 to 8 mg/kg for an average adult human weighing 60 kg and having a body surface area of 1.6 m$^2$). In specific embodiments, the subsequently weekly dose is 0.1 to 250 mg/m$^2$, such as 0.5-200 mg/m$^2$, such as 1-150 mg/m$^2$, such as 2-100 mg/m$^2$, such as 2.5-100 mg/m$^2$, such as 5-75 mg/m$^2$, such as 10-50 mg/m$^2$, such as 15-150 mg/m$^2$, such as 20-100 mg/m$^2$, such as 30-125 mg/m$^2$, such as 40-150 mg/m$^2$, such as 50-175 mg/m$^2$.

For treatment of EGFR-expressing metastatic color rectal carcinoma in patients who are refractory to inriotecan-based chemotherapy, an anti-EGFR antibody of the disclosure is administered intravenously as a single agent at an initial dose of 0.1 to 500 mg/m$^2$ (e.g., 0.003 to 13.3 mg/kg for an average adult human weighing 60 kg and having a body surface area of 1.6 m$^2$). In specific embodiments, the initial dose is 0.1-400 mg/m$^2$, 0.25-300 mg/m$^2$, 0.5-250 mg/m$^2$, 1-200 mg/m$^2$, 1-150 mg/m$^2$, 2-100 mg/m$^2$, 5-75 mg/m$^2$, 8-50 mg/m$^2$, 10-350 mg/m$^2$, 15-300 mg/m$^2$, 20-250 mg/m$^2$, 30-200 mg/m$^2$ or 40-100 mg/m$^2$. Following the initial dose, an anti-EGFR antibody of the disclosure is administered intravenously once weekly at a dose of 0.1 to 300 mg/m$^2$ (i.e., 0.003 to 8 mg/kg for an average adult human weighing 60 kg and having a body surface area of 1.6 m$^2$). In specific embodiments, the subsequently weekly dose is 0.1 to 250 mg/m$^2$, such as 0.5-200 mg/m$^2$, such as 1-150 mg/m$^2$, such as 2-100 mg/m$^2$, such as 2.5-100 mg/m$^2$, such as 5-75 mg/m$^2$, such as 10-50 mg/m$^2$, such as 15-150 mg/m$^2$, such as 20-100 mg/m$^2$, such as 30-125 mg/m$^2$, such as 40-150 mg/m$^2$, such as 50-175 mg/m$^2$.

6.11 Diagnostic and Pharmaceutical Kits

Encompassed by the present disclosure are pharmaceutical kits containing the anti-EGFR antibodies (including antibody conjugates) of the disclosure. The pharmaceutical kit is a package comprising the anti-EGFR antibody of the disclosure (e.g., either in lyophilized form or as an aqueous solution) and one or more of the following:

A combination therapeutic agent, for example, as described in Section 6.8 above;

A device for administering the anti-EGFR antibody, for example, a pen, needle and/or syringe; and Pharmaceutical grade water or buffer to re-suspend the antibody if the antibody is in lyophilized form.

In certain aspects, each unit dose of the anti-EGFR antibody is packaged separately, and a kit can contain one or more unit doses (e.g., two unit doses, three unit doses, four unit doses, five unit doses, eight unit doses, ten unit doses, or more). In a specific embodiment, the one or more unit doses are each housed in a syringe or pen.

Diagnostic kits containing the anti-EGFR antibodies (including antibody conjugates) of the disclosure are also encompassed herein. The diagnostic kit is a package comprising the anti-EGFR antibody of the disclosure (e.g., either in lyophilized form or as an aqueous solution) and one or more reagents useful for performing a diagnostic assay. Where the anti-EGFR antibody is labeled with an enzyme, the kit can include substrates and cofactors required by the enzyme (e.g., a substrate precursor which provides the detectable chromophore or fluorophore). In addition, other additives can be included, such as stabilizers, buffers (e.g., a block buffer or lysis buffer), and the like. In certain embodiments, the anti-EGFR antibody included in a diagnostic kit is immobilized on a solid surface, or a solid surface (e.g., a slide) on which the antibody can be immobilized is included in the kit. The relative amounts of the various reagents can be varied widely to provide for concentrations in solution of the reagents which substantially optimize the sensitivity of the assay. In a specific embodiment, the antibody and one or more reagents can be provided (individually or combined) as dry powders, usually lyophilized, including excipients which on dissolution will provide a reagent solution having the appropriate concentration.

7. EXAMPLE 1

Comparison of Binding Affinity of Cetuximab (Erbitux) and Hu225 to EGFR

The relative binding affinities of cetuximab and hu225 to EGFR were determined by a competition assay using fluorescence-activated cell sorting (FACS). A431 cells were grown to $2 \times 10^5$ cells per well of V-bottom 96-well plates. Cells were washed with FACS staining buffer (FSB). Starting with an initial concentration of 10 µg/mL of each of the competitor antibodies (unlabeled cetuximab and hu225), 1:3 serial dilutions were made. Biotinylated cetuximab was diluted to a final concentration of 0.5 µg/mL (derived from titration results). Biotinylated cetuximab was then mixed with either competitor antibody at various concentrations and the mixtures were transferred to the 96-well plates containing the A431 cells. The plates were then incubated on ice for 1 hour, and then washed twice with FSB. 25 µL of Strepavidin-RPE conjugate (Biosource) diluted to 2.5 µg/mL in FSB were added to the wells, and the plates were incubated on ice for another 30 minutes in the dark. Cells were washed two times with FSB, and stained cells were resuspended with 200 µL of fixing buffer (1% paraformaldehyde). Samples were read using a flow cytometer.

Results of three experiments are shown in FIG. 2 and indicate that the measured binding affinities ($IC_{50}$) of cetuximab and hu225 to EGFR are comparable. The term "chErbitux" refers to cetuximab.

8. EXAMPLE 2

Identification of Variants of Hu225 with Increased Affinity to EGFR

The hu225 antibody was subjected to comprehensive mutational analysis to identify mutants that had increased affinity to EGFR as compared to wild-type hu225. The increased affinity of candidate high affinity mutants to EGFR as compared to hu225 was analyzed by FACS to confirm their relative increase in binding to EGFR as compared to hu225.

8.1 Materials and Methods

To determine binding of individual variants to EGFR, cell surface displayed hu225 immunoglobulin variants were incubated with soluble EGFR at sub-saturating conditions (below $K_D$), and the degree of binding was quantitated by FACS. Individual hu225 variants were constructed in the mammalian cell surface display vector (Akamatsu et al., 2007, J. Immunol. Methods 327(1-2):40-52), and transfected into a human cell line. 400 ng of plasmid DNA in 50 µL Hybridoma-Serum Free Medium (SFM) were mixed with 1 µL of Lipofectamine 2000 in 50 µL Hybridoma-SFM and incubated for 20 minutes at room temperature. This mixture was then added to one well of a 24-well plate, previously seeded 24 hours earlier with $2 \times 10^5$ cells of the human embryonic kidney-derived cell line 293c18 in 0.5 mL of DME medium supplemented with 10% Fetal Bovine Serum and 0.25 mg/mL G418. After 48 hours, the cells were harvested and ready for FACS staining.

For FACS staining, approximately $5 \times 10^5$ cells were incubated with 1 nM EGFR-CLambda-AF647 (EGFR extracellular domain fused to CLambda and directly conjugated with Alexa Fluor 647 dye) and 1/500 dilution of Goat anti-Human Kappa-PE (Southern Biotech #2060-09) in 1 mL of Phosphate Buffered Saline (PBS) plus 0.5% Bovine Serum Albumin (BSA), and incubated at room temperature for 2 hours. Cells were washed 3 times with 1 mL of cold PBS+0.5% BSA, resuspended in 200 µL of PBS+1% Formaldehyde, and analyzed on a BD FACS Calibur. Cells were gated to only include the IgG expressing population, and the mean fluorescence intensity (MFI) of the binding (Alexa Fluor 647) channel was determined. The MFI for binding of each variant was compared to wild-type hu225 for each sample set to normalize for experiment-to-experiment variability.

8.2 Results

FIGS. 9 and 10 show mutations in the hu225 heavy and light chain CDRs that FACS studies indicate increase affinity toward EGFR. The binding of these hu225 variants to EGFR is shown in FIG. 3. Results of the FACS studies are tabulated in FIGS. 20-1 and 20-2 as fold increase in affinity to EGFR over wild-type hu225.

FIGS. 11 and 13 show further mutations in the hu225 heavy chain CDRs that preliminary studies indicate have higher affinity than hu225 towards EGFR (data not shown). FIGS. 12 and 14 show further mutations in the hu225 light chain CDRs that preliminary studies indicate have higher affinity than hu225 towards EGFR (data not shown). FIGS. 15 and 16 respectively show heavy chain variants and light chain variants that that preliminary studies indicate have an affinity to EGFR similar to that of hu225 (data not shown).

9. EXAMPLE 3

Further Characterization of Variants of Hu225 with Increased Affinity to EGFR (ELISA, AlphaLisa® and Biacore Studies)

9.1 Materials and Methods

To determine binding of individual variants to EGFR, cell surface displayed hu225 immunoglobulin variants were incubated with soluble EGFR at sub-saturating conditions (below $K_D$), and the degree of binding was quantitated by FACS (as described in Example 2 above), ELISA, alphaLISA, and/or BIAcore.

ELISA involves the attachment of a capture antibody to a solid phase support, whereupon samples containing antigen are then added in a matrix or buffer adapted to minimize attachment to the solid phase. An enzyme-labeled antibody is then added for detection and determination of binding affinities. ELISA can be used to determine the binding affinity of individual variants, e.g., anti-EGFR antibodies or antibody binding fragments of the disclosure, to EGFR. See, for example, Patel et al. Anticancer Research 27, no. 5A:3355-3366, 2007; and Nix et al. in "Immunoassays, a Practical Approach," ed. J. P. Gosling, pp. 239-261, Oxford University Press, 2000).

AlphaLISA is analogous to ELISA: an analyte is captured by a biotinylated antibody bound to streptavidin-coated donor beads and a second antibody conjugated to AlphaLISA acceptor beads. The binding of the two antibodies to the analyte brings donor and acceptor beads into proximity. Laser irradiation of donor beads at 680 nm generates a flow of singlet oxygen, triggering a cascade of chemical events in nearby acceptor beads, which results in a chemiluminescent emission at 615 nm. In competitive AlphaLISA immunoassays, a biotinylated analyte bound to streptavidin donor beads is used with an antibody conjugated to AlphaLISA acceptor beads. AlphaLISA can also be used to determine the binding affinity of individual variants, e.g., anti-EGFR antibodies or antibody binding fragments of the disclosure, to EGFR. See, for example, Ullman et al., Clinical Chemistry 42, no. 9:1518-1526, 1996; and Hideharu et al., Cancer Science 98, no. 8:1275-1280, 2007.

BIAcore assays determine binding using Surface Plasmon Resonance (SPR), an optical phenomenon enabling detection of unlabeled interactants. BIAcore is another method for determining the binding affinity of individual variants, e.g. anti-EGFR antibodies or antibody binding fragments of the disclosure, to EGFR. See, for example, U.S. Pat. App. No. 2008/0274114; and Che et al., J. of Pharm. and Biomed. Analysis 50, no. 2 (Sep. 8, 2009):183-188.

KinExA (kinetic exclusion assay) measures the concentration of uncomplexed receptor (R) molecule in a mixture of receptor, ligand (L), and LR complex. The concentration of uncomplexed R is measured by exposing the solution phase mixture to solid phase immobilized L for a very brief period of time. The "contact time" between the solution phase mixture and the solid phase immobilized L is kept short enough that dissociation of LR complex is insignificant. When the possibility of significant dissociation of LR complex is kinetically excluded, only uncomplexed ("free") R can bind to the solid phase. The amount of free R that binds to the solid phase (measured by fluorescence emission from a secondary label) is directly proportional to the concentration of free R in the solution phase sample. KinExA can also be used to determine the binding affinity of individual variants, e.g., anti-EGFR antibodies or antibody binding fragments of the disclosure, to EGFR. See, for example, US Pat. App. No. 2008/0274114; and Darling, et al. ASSAY and Drug Development Technologies, 2:647-657, 2004.

9.2 Results

The results of these additional binding studies for exemplary single substitution variants in the heavy chain CDRs are shown in FIG. 20-1. The results for exemplary single substitution variants in the light chain CDRs are shown in FIG. 20-2. The results for exemplary multiple substitution variants are in both the heavy and light chain are shown in FIG. 20-3. The results in FIGS. 20-1 through 20-3 are show as a fold increase in affinity as compared to hu225.

10. EXAMPLE 4

Testing for CD4+ T Cell Epitope Regions in Cetuximab and Humanized Cetuximab 10.1 Materials & Methods 10.1.1 Peptides Peptides were synthesized using a multi-pin format by Mimotopes (Adelaide, Australia). The sequences of the cetuximab and hu225 light and heavy chain variable regions were synthesized as 15-mer peptides overlapping by 12 amino acids (FIGS. 4 and 5, respectively) for a total of 134 peptides. Peptides arrived lyophilized and were re-suspended in DMSO (Sigma-Aldrich) at approximately 1-2 mg/mL. Stock peptides were kept frozen at −20° C.

10.1.2 Human Peripheral Blood Mononuclear Cells

Community donor buffy coat products were purchased from the Stanford Blood Center, Palo Alto, Calif. Buffy coat material was diluted 1:1 v:v with DPBS containing no calcium or magnesium. Diluted buffy coat material (25-35 mL) was underlayed in 50 mL conical centrifuge tubes (Sarsted or Costar) with 12.5 mL of FicollPaque-PLUS (GE Healthcare). The samples were centrifuged at 900 g for 30 minutes at room temperature. Peripheral blood mononuclear cells (PBMC) were collected from the interface. DPBS was added to bring the final volume to 50 mL and the cells were centrifuged at 350 g for 5 minutes. Pelleted cells were resuspended in DPBS and counted.

10.1.3 Dendritic Cells

For isolation of dendritic cells, T75 culture flasks (Costar) were seeded with $10^8$ freshly isolated PBMC in a total volume of 30 mL AIM V media (Invitrogen). Excess PBMC were frozen at −80° C. in 90% fetal calf serum (FCS), 10% DMSO at $5 \times 10^7$ cells/mL. T75 flasks were incubated at 37° C. in 5% $CO_2$ for 2 hours. Non-adherent cells were removed, and the adherent monolayer was washed with DPBS. To differentiate dendritic cells from monocytes, 30 mL of AIM V media containing 800 units/mL of GM-CSF (R and D Systems) and 500 units/mL IL-4 (R and D Systems) were added. Flasks were incubated for 5 days. On day 5 IL-1α (Endogen) and TNFα (Endogen) were added to 50 pg/mL and 0.2 ng/mL. Flasks were incubated two more days. On day 7, dendritic cells were collected by the addition of 3 mL of 100 mM EDTA containing 0.5 to 1.0 mg Mitomycin C (Sigma-Aldrich) for a final concentration of 10 mM EDTA and 16.5 to 33 µg/mL Mitomycin C. Flasks were incubated an additional hour at 37° C. and 5% $CO_2$. Dendritic cells were collected, and washed in AIM V media 2-3 times.

10.1.4 Cell Culture

On day 7, previously frozen autologous PBMC were thawed quickly in a 37° C. water bath. Cells were immediately diluted into DPBS or AIM V media and centrifuged at 350 g for 5 minutes. CD4+ cells were enriched by negative selection using magnetic beads (Easy-Sep CD4+ kit, Stem Cell Technologies). Autologous CD4+ T cells and dendritic cells were co-cultured at $2 \times 10^5$ CD4+ T cells per $2 \times 10^4$ dendritic cells per well in 96 well round bottomed plates (Costar 9077). Peptides were added at approximately 5 µg/mL. Control wells contained the DMSO (Sigma) vehicle alone at 0.25% v:v. Positive control wells contained DMSO at 0.25% and tetanus toxoid (List Biologicals or CalBioChem) at 1 µg/mL. Cultures were incubated for 5 days. On day 5, 0.25 µCi per well of tritiated thymidine (Amersham or GE Healthcare) was added. Cultures were harvested on day 6 to filtermats using a Packard Filtermate Cell harvester. Scintillation counting was performed using a Wallac MicroBeta 1450 scintillation counter (Perkin Elmer).

10.1.5 Data Analysis

Average background CPM values were calculated by averaging individual results from 6 to 12 replicates. The CPM values of the four positive control wells were averaged. Replicate or triplicate wells for each peptide were averaged. Stimulation index values for the positive control and the peptide wells were calculated by dividing the average experimental CPM values by the average control values. In order to be included in the dataset, a stimulation index of greater than 3.0 in the tetanus toxoid positive control wells was required. A response was noted for any peptide resulting in a stimulation index of 2.95 or greater. Peptides were tested using peripheral blood samples from a group of 106 donors for the hu225 peptides, and 87 donors for the cetuximab peptides. Responses to all peptides were compiled. For each peptide tested, the percentage of the donor set that responded with a stimulation index of 2.95 or greater was calculated. In addition, the average stimulation index for all donors was also calculated.

Figure 6:
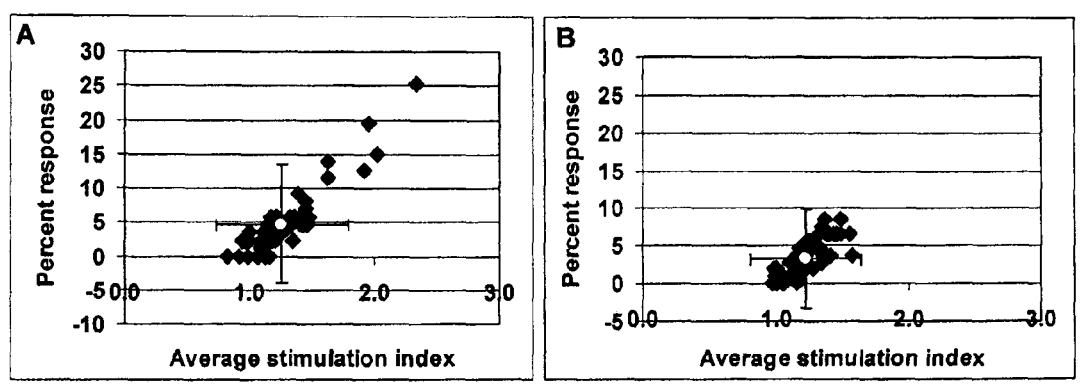

10.2 Results 10.2.1 Identification of CD4+ T Cell Epitopes in the Cetuximab and Humanized Cetuximab VH and VL Regions CD4+ T cell epitope peptides were identified by an analysis of the percent responses to the peptides within the donor sets. The average percent response was calculated for all peptides tested describing the cetuximab and hu225 heavy chain and light chain variable regions. A response rate greater than or equal to the average background response plus three standard deviations was considered a potential CD4+ T cell epitope. The average stimulation index was calculated for all peptides in the dataset. The data for both antibody $V_H$ and $V_L$ regions is shown in FIG. 6. In FIG. 6A, the composite data for cetuximab $V_H$ and $V_L$ regions is shown. The overall average stimulation index is 1.27±0.27 standard deviations. The average percent response rate is 4.72±4.38 standard deviations. The wide standard deviation is due to the presence of responses within the dataset that are very high in both the average SI and the percent response. As cetuximab is a chimeric antibody, the high response rate is likely due to the murine derivation of the peptide sequences. Consistent with this interpretation, there are no prominent peptide responses in the hu225 dataset (FIG. 6B). The average stimulation index in the hu225 dataset is 1.22±0.14, and the average percent response rate is 3.3±2.19.

These results suggest that the humanization process as performed on the M225 hybridoma $V_H$ and $V_L$ regions resulted in an antibody molecule with no detectable CD4+ T cell helper epitopes. The absence of CD4+ T cell epitopes is likely to confer reduced immunogenic potential on the antibody product.

11. SPECIFIC EMBODIMENTS

Citation of References

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

---

What is claimed is:

1. A monoclonal antibody or a binding fragment thereof which:
   (a) specifically binds to human EGFR;
   (b) competes for binding to human EGFR with an antibody comprising a $V_H$ sequence of SEQ ID NO:1 and a $V_L$ sequence of SEQ ID NO:2;
   (c) comprises six CDRs that altogether have up to seven amino acid substitutions, selected from one or more of Tables 3 to 14-3, as compared to the CDRs of SEQ ID NO:3 (CDR-H1), SEQ ID NO:4 (CDR-H2), SEQ ID NO:5 (CDR-H3), SEQ ID NO:6 (CDR-L1), SEQ ID NO:7 (CDR-L2), and SEQ ID NO:8 (CDR-L3), wherein any individual CDR has no more than three amino acid substitutions as compared to the corresponding CDR of SEQ ID NO:3 (CDR-H1), SEQ ID NO:4 (CDR-H2), SEQ ID NO:5 (CDR-H3), SEQ ID NO:6 (CDR-L1), SEQ ID NO:7 (CDR-L2), or SEQ ID NO:8 (CDR-L3); and
   (d) has a substitution in CDR-L1 selected from G30Y, G30W, G30F, G30T, G30M, G30S, G30C, G30H, G30K, G30Q and G30R (as defined by Kabat numbering) as compared to a CDR-L1 of SEQ ID NO:6.

2. The monoclonal antibody or binding fragment of claim 1, wherein the CDRs altogether have up to six amino acid substitutions as compared to the six CDRs of SEQ ID NO:3 (CDR-H1), SEQ ID NO:4 (CDR-H2), SEQ ID NO:5 (CDR-H3), SEQ ID NO:6 (CDR-L1), SEQ ID NO:7 (CDR-L2), and SEQ ID NO:8 (CDR-L3).

3. The monoclonal antibody or binding fragment of claim 1, wherein the CDRs altogether have up to five amino acid substitutions as compared to the six CDRs of SEQ ID NO:3 (CDR-H1), SEQ ID NO:4 (CDR-H2), SEQ ID NO:5 (CDR-H3), SEQ ID NO:6 (CDR-L1), SEQ ID NO:7 (CDR-L2), and SEQ ID NO:8 (CDR-L3).

4. The monoclonal antibody or binding fragment of claim 1, wherein the CDRs altogether have up to four amino acid substitutions as compared to the six CDRs of SEQ ID NO:3 (CDR-H1), SEQ ID NO:4 (CDR-H2), SEQ ID NO:5 (CDR-H3), SEQ ID NO:6 (CDR-L1), SEQ ID NO:7 (CDR-L2), and SEQ ID NO:8 (CDR-L3).

5. The monoclonal antibody or binding fragment of claim 4, in which any individual CDR has no more than two amino acid substitutions as compared to the corresponding CDR of SEQ ID NO:3 (CDR-H1), SEQ ID NO:4 (CDR-H2), SEQ ID NO:5 (CDR-H3), SEQ ID NO:6 (CDR-L1), SEQ ID NO:7 (CDR-L2), and SEQ ID NO:8 (CDR-L3).

6. The monoclonal antibody or binding fragment of claim 1, which comprises the CDR-H3 substitution Y98W (as defined by Kabat numbering) as compared to said CDR-H3 of SEQ ID NO:5.

7. The monoclonal antibody or binding fragment of claim 1, which comprises the CDR-H2 substitution I51G (as defined by Kabat numbering) as compared to said CDR-H2 of SEQ ID NO:4.

8. The monoclonal antibody or binding fragment of claim 7, which comprises the CDR-H3 substitution Y98W (as defined by Kabat numbering) as compared to said CDR-H3 of SEQ ID NO:5.

9. The monoclonal antibody or binding fragment of claim 1, which comprises the CDR-L3 substitution N92L (as defined by Kabat numbering) as compared to said CDR-L3 of SEQ ID NO:8.

10. The monoclonal antibody or binding fragment of claim 8, which comprises the CDR-L3 substitution N92L (as defined by Kabat numbering) as compared to said CDR-L3 of SEQ ID NO:8.

11. The monoclonal antibody or binding fragment of claim 1, whose CDRs have amino acid sequences of SEQ ID NO:3 (CDR-H1), SEQ ID NO:4 (CDR-H2), SEQ ID NO:5 (CDR-H3), SEQ ID NO:233 (CDR-L1), SEQ ID NO:7 (CDR-L2), and SEQ ID NO:8 (CDR-L3).

12. The monoclonal antibody or binding fragment of claim 1, whose CDRs have amino acid sequences of SEQ ID NO:3 (CDR-H1), SEQ ID NO:4 (CDR-H2), SEQ ID NO:230 (CDR-H3), SEQ ID NO:233 (CDR-L1), SEQ ID NO:7 (CDR-L2), and SEQ ID NO:8 (CDR-L3).

13. The monoclonal antibody or binding fragment of claim 1, whose CDRs have amino acid sequences of SEQ ID NO:3 (CDR-H1), SEQ ID NO:207 (CDR-H2), SEQ ID NO:230 (CDR-H3), SEQ ID NO:233 (CDR-L1), SEQ ID NO:7 (CDR-L2), and SEQ ID NO:8 (CDR-L3).

14. The monoclonal antibody or binding fragment of claim 1, which is a humanized antibody or anti-EGFR binding fragment of a humanized antibody, respectively.

15. The monoclonal antibody or binding fragment of claim 1, which is an IgG.

16. The monoclonal antibody or binding fragment of claim 15, which is an $IgG_1$.

17. The monoclonal antibody or binding fragment of claim 1, which is a bispecific antibody further comprising a binding portion specific for an antigen other than human EGFR.

18. The monoclonal antibody or binding fragment of claim 1, which includes one or more mutations in the Fc region that increases ADCC activity.

19. The monoclonal antibody or binding fragment of claim 1, which is non-fucosylated.

20. The monoclonal antibody or binding fragment of claim 1, which includes one or more mutations in the Fc region that increases binding to FcγR.

21. The monoclonal antibody or binding fragment of claim 1, which includes one or more mutations in the Fc region that increases binding to FcRn.

22. The monoclonal antibody or binding fragment of claim 1, which includes one or more mutations in the Fc region that decreases ADCC activity.

23. The monoclonal antibody or binding fragment of claim 1 which has the heavy chain framework sequences of the $V_H$ sequence of SEQ ID NO:1 and the light chain framework sequences of the $V_L$ sequence of SEQ ID NO:2.

24. The monoclonal antibody or binding fragment of claim 1 which has the heavy chain framework sequences of the $V_H$ sequence of SEQ ID NO:9 and the light chain framework sequences of the $V_L$ sequence of SEQ ID NO:10.

25. The monoclonal antibody or binding fragment of claim 1 which is purified to at least 95% homogeneity.

26. An antibody-drug conjugate comprising a monoclonal antibody or binding fragment according to any one of claims 1 to 5.

27. A pharmaceutical composition comprising a monoclonal antibody or binding fragment according to any one of claims 1 to 5, and a pharmaceutically acceptable carrier.

28. A method of treating cancer expressing EGFR comprising administering to a human patient in need thereof a therapeutically effective amount of a monoclonal antibody or binding fragment according to claim 1.

29. The method of claim 28, wherein the cancer is squamous cell carcinoma of the head and neck.

30. The method of claim 28, wherein the cancer is colorectal cancer.

31. The method of any one of claims 28-30, further comprising administering to the patient at least one chemotherapeutic agent.

32. The method of claim 31, wherein said at least one chemotherapeutic agent is a cytotoxic agent.

33. The method of claim 31, wherein said at least one chemotherapeutic agent is selected from irinotecan, 5-fluorouracil, cisplatin, carboplatin, leucovorin calcium, capecitabine, and paclitaxel.

34. The method of claim 28, further comprising administering radiation to said patient.

35. A method of treating cancer expressing EGFR comprising administering to a human patient in need thereof a therapeutically effective amount of an antibody-drug conjugate, wherein said antibody of the antibody-drug conjugate is a monoclonal antibody or binding fragment according to claim 1.

36. The method of claim 35, wherein the cancer is squamous cell carcinoma of the head and neck.

37. The method of claim 35, wherein the cancer is colorectal cancer.

38. The method of any one of claims 35-37, further comprising administering to the patient at least one chemotherapeutic agent.

39. The method of claim 38, wherein said at least one chemotherapeutic agent is a cytotoxic agent.

40. The method of claim 38, wherein said at least one chemotherapeutic agent is selected from irinotecan, 5-fluorouracil, cisplatin, carboplatin, leucovorin calcium, capecitabine, and paclitaxel.

41. The method of claim 35, further comprising administering radiation to said patient.

* * * * *

SEQUENCE LISTING

```
<160> NUMBER OF SEQ ID NOS: 387

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
```

```
                    20                  25                  30
Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Tyr Gly Val His
1               5

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Ile Trp Ser Gly Gly Asn Thr Asp Tyr Asn Thr Pro Phe Thr Ser
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Leu Thr Tyr Tyr Asp Tyr Glu Phe Ala Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Ser Ile Gly Thr Asn Ile His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 7

Tyr Ala Ser Glu Ser Ile Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Asn Asn Asn Trp Pro Thr Thr
1               5

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Thr Ile Asn Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Gly Gln Ala Pro Arg Leu Leu Ile
        35                  40                  45

Lys Tyr Ala Ser Glu Ser Ile Ser Gly Ile Pro Asp Arg Phe Ser Gly
    50                  55                  60

Ser Gly Ser Gly Thr Asp Phe Thr Leu Thr Ile Ser Arg Leu Glu Pro
```

```
                65                  70                  75                  80
Glu Asp Phe Ala Val Tyr Tyr Cys Gln Gln Asn Asn Asn Trp Pro Thr
                    85                  90                  95
Thr Phe Gly Gln Gly Thr Lys Leu Glu Ile Lys Arg
            100                 105

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Val Gln Leu Lys Gln Ser Gly Pro Gly Leu Val Gln Pro Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ile Leu Leu Thr Gln Ser Pro Val Ile Leu Ser Val Ser Pro
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Lys Gln Ser Gly Pro Gly Leu Val Gln Pro Ser Gln Ser Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Thr Gln Ser Pro Val Ile Leu Ser Val Ser Pro Gly Glu Arg
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Gly Pro Gly Leu Val Gln Pro Ser Gln Ser Leu Ser Ile Thr
1               5                   10                  15

<210> SEQ ID NO 16
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Pro Val Ile Leu Ser Val Ser Pro Gly Glu Arg Val Ser Phe
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Leu Val Gln Pro Ser Gln Ser Leu Ser Ile Thr Cys Thr Val
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Leu Ser Val Ser Pro Gly Glu Arg Val Ser Phe Ser Cys Arg
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Pro Ser Gln Ser Leu Ser Ile Thr Cys Thr Val Ser Gly Phe
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Ser Pro Gly Glu Arg Val Ser Phe Ser Cys Arg Ala Ser Gln
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ser Leu Ser Ile Thr Cys Thr Val Ser Gly Phe Ser Leu Thr
```

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Glu Arg Val Ser Phe Ser Cys Arg Ala Ser Gln Ser Ile Gly
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ile Thr Cys Thr Val Ser Gly Phe Ser Leu Thr Asn Tyr Gly
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Ser Phe Ser Cys Arg Ala Ser Gln Ser Ile Gly Thr Asn Ile
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Thr Val Ser Gly Phe Ser Leu Thr Asn Tyr Gly Val His Trp
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Cys Arg Ala Ser Gln Ser Ile Gly Thr Asn Ile His Trp Tyr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 27

Ser Gly Phe Ser Leu Thr Asn Tyr Gly Val His Trp Val Arg Gln
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ser Gln Ser Ile Gly Thr Asn Ile His Trp Tyr Gln Gln Arg
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Leu Thr Asn Tyr Gly Val His Trp Val Arg Gln Ser Pro Gly
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Ile Gly Thr Asn Ile His Trp Tyr Gln Gln Arg Thr Asn Gly
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Tyr Gly Val His Trp Val Arg Gln Ser Pro Gly Lys Gly Leu
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Asn Ile His Trp Tyr Gln Gln Arg Thr Asn Gly Ser Pro Arg
1               5                   10                  15

<210> SEQ ID NO 33
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 33

Val His Trp Val Arg Gln Ser Pro Gly Lys Gly Leu Glu Trp Leu
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Trp Tyr Gln Gln Arg Thr Asn Gly Ser Pro Arg Leu Leu Ile
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Arg Gln Ser Pro Gly Lys Gly Leu Glu Trp Leu Gly Val Ile
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Arg Thr Asn Gly Ser Pro Arg Leu Leu Ile Lys Tyr Ala
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Pro Gly Lys Gly Leu Glu Trp Leu Gly Val Ile Trp Ser Gly
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Asn Gly Ser Pro Arg Leu Leu Ile Lys Tyr Ala Ser Glu Ser
1               5                   10                  15
```

```
<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Gly Leu Glu Trp Leu Gly Val Ile Trp Ser Gly Gly Asn Thr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Pro Arg Leu Leu Ile Lys Tyr Ala Ser Glu Ser Ile Ser Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Trp Leu Gly Val Ile Trp Ser Gly Gly Asn Thr Asp Tyr Asn
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Leu Ile Lys Tyr Ala Ser Glu Ser Ile Ser Gly Ile Pro Ser
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Val Ile Trp Ser Gly Gly Asn Thr Asp Tyr Asn Thr Pro Phe
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

Lys Tyr Ala Ser Glu Ser Ile Ser Gly Ile Pro Ser Arg Phe Ser
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Ser Gly Gly Asn Thr Asp Tyr Asn Thr Pro Phe Thr Ser Arg
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Glu Ser Ile Ser Gly Ile Pro Ser Arg Phe Ser Gly Ser Gly
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Asn Thr Asp Tyr Asn Thr Pro Phe Thr Ser Arg Leu Ser Ile
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Ser Gly Ile Pro Ser Arg Phe Ser Gly Ser Gly Ser Gly Thr
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Tyr Asn Thr Pro Phe Thr Ser Arg Leu Ser Ile Asn Lys Asp
1               5                   10                  15

<210> SEQ ID NO 50
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 50

Ile Pro Ser Arg Phe Ser Gly Ser Gly Ser Gly Thr Asp Phe Thr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Pro Phe Thr Ser Arg Leu Ser Ile Asn Lys Asp Asn Ser Lys
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Phe Ser Gly Ser Gly Ser Gly Thr Asp Phe Thr Leu Ser Ile
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ser Arg Leu Ser Ile Asn Lys Asp Asn Ser Lys Ser Gln Val
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Gly Ser Gly Thr Asp Phe Thr Leu Ser Ile Asn Ser Val
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Ser Ile Asn Lys Asp Asn Ser Lys Ser Gln Val Phe Phe Lys
1               5                   10                  15

<210> SEQ ID NO 56
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Gly Thr Asp Phe Thr Leu Ser Ile Asn Ser Val Glu Ser Glu
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asn Lys Asp Asn Ser Lys Ser Gln Val Phe Phe Lys Met Asn Ser
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Phe Thr Leu Ser Ile Asn Ser Val Glu Ser Glu Asp Ile Ala
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Ser Lys Ser Gln Val Phe Phe Lys Met Asn Ser Leu Gln Ser
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Ser Ile Asn Ser Val Glu Ser Glu Asp Ile Ala Asp Tyr Tyr
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Gln Val Phe Phe Lys Met Asn Ser Leu Gln Ser Asn Asp Thr
```

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Ser Val Glu Ser Glu Asp Ile Ala Asp Tyr Tyr Cys Gln Gln
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Phe Lys Met Asn Ser Leu Gln Ser Asn Asp Thr Ala Ile Tyr
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Glu Ser Glu Asp Ile Ala Asp Tyr Tyr Cys Gln Gln Asn Asn Asn
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Asn Ser Leu Gln Ser Asn Asp Thr Ala Ile Tyr Tyr Cys Ala
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Ile Ala Asp Tyr Tyr Cys Gln Gln Asn Asn Asn Trp Pro Thr
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 67

Leu Gln Ser Asn Asp Thr Ala Ile Tyr Tyr Cys Ala Arg Ala Leu
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Tyr Tyr Cys Gln Gln Asn Asn Asn Trp Pro Thr Thr Phe Gly
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asn Asp Thr Ala Ile Tyr Tyr Cys Ala Arg Ala Leu Thr Tyr Tyr
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Gln Gln Asn Asn Asn Trp Pro Thr Thr Phe Gly Ala Gly Thr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Ile Tyr Tyr Cys Ala Arg Ala Leu Thr Tyr Tyr Asp Tyr Glu
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asn Asn Asn Trp Pro Thr Thr Phe Gly Ala Gly Thr Lys Leu Glu
1               5                   10                  15

<210> SEQ ID NO 73
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 73

Tyr Cys Ala Arg Ala Leu Thr Tyr Tyr Asp Tyr Glu Phe Ala Tyr
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asn Asn Trp Pro Thr Thr Phe Gly Ala Gly Thr Lys Leu Glu Leu
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ala Leu Thr Tyr Tyr Asp Tyr Glu Phe Ala Tyr Trp Gly Gln
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Leu Thr Tyr Tyr Asp Tyr Glu Phe Ala Tyr Trp Gly Gln Gly
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Val Gln Leu Val Glu Ser Gly Gly Gly Leu Val Gln Pro Gly
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Ile Leu Leu Thr Gln Ser Pro Gly Thr Leu Ser Leu Ser Pro
1               5                   10                  15
```

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Val Glu Ser Gly Gly Gly Leu Val Gln Pro Gly Gly Ser Leu
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Thr Gln Ser Pro Gly Thr Leu Ser Leu Ser Pro Gly Glu Arg
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Gly Gly Gly Leu Val Gln Pro Gly Gly Ser Leu Arg Leu Ser
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Pro Gly Thr Leu Ser Leu Ser Pro Gly Glu Arg Ala Thr Leu
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Leu Val Gln Pro Gly Gly Ser Leu Arg Leu Ser Cys Ala Ala
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Leu Ser Leu Ser Pro Gly Glu Arg Ala Thr Leu Ser Cys Arg
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Pro Gly Gly Ser Leu Arg Leu Ser Cys Ala Ala Ser Gly Phe
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Ser Pro Gly Glu Arg Ala Thr Leu Ser Cys Arg Ala Ser Gln
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Ser Leu Arg Leu Ser Cys Ala Ala Ser Gly Phe Ser Leu Thr
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Glu Arg Ala Thr Leu Ser Cys Arg Ala Ser Gln Ser Ile Gly
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Leu Ser Cys Ala Ala Ser Gly Phe Ser Leu Thr Asn Tyr Gly
1               5                   10                  15

<210> SEQ ID NO 90
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 90

Ala Thr Leu Ser Cys Arg Ala Ser Gln Ser Ile Gly Thr Asn Ile
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Cys Ala Ala Ser Gly Phe Ser Leu Thr Asn Tyr Gly Val His Trp
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Cys Arg Ala Ser Gln Ser Ile Gly Thr Asn Ile His Trp Tyr
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Gly Phe Ser Leu Thr Asn Tyr Gly Val His Trp Val Arg Gln
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Ser Gln Ser Ile Gly Thr Asn Ile His Trp Tyr Gln Gln Lys
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Leu Thr Asn Tyr Gly Val His Trp Val Arg Gln Ala Pro Gly
1               5                   10                  15

<210> SEQ ID NO 96
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Ile Gly Thr Asn Ile His Trp Tyr Gln Gln Lys Pro Gly Gln
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Tyr Gly Val His Trp Val Arg Gln Ala Pro Gly Lys Gly Leu
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Thr Asn Ile His Trp Tyr Gln Gln Lys Pro Gly Gln Ala Pro Arg
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Val His Trp Val Arg Gln Ala Pro Gly Lys Gly Leu Glu Trp Leu
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

His Trp Tyr Gln Gln Lys Pro Gly Gln Ala Pro Arg Leu Leu Ile
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Val Arg Gln Ala Pro Gly Lys Gly Leu Glu Trp Leu Gly Val Ile
```

```
1               5                   10                  15
```

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

```
Gln Gln Lys Pro Gly Gln Ala Pro Arg Leu Leu Ile Lys Tyr Ala
1               5                   10                  15
```

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

```
Ala Pro Gly Lys Gly Leu Glu Trp Leu Gly Val Ile Trp Ser Gly
1               5                   10                  15
```

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

```
Pro Gly Gln Ala Pro Arg Leu Leu Ile Lys Tyr Ala Ser Glu Ser
1               5                   10                  15
```

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

```
Lys Gly Leu Glu Trp Leu Gly Val Ile Trp Ser Gly Gly Asn Thr
1               5                   10                  15
```

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Ala Pro Arg Leu Leu Ile Lys Tyr Ala Ser Glu Ser Ile Ser Gly
1               5                   10                  15
```

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Glu Trp Leu Gly Val Ile Trp Ser Gly Gly Asn Thr Asp Tyr Asn
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Leu Ile Lys Tyr Ala Ser Glu Ser Ile Ser Gly Ile Pro Asp
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Val Ile Trp Ser Gly Gly Asn Thr Asp Tyr Asn Thr Pro Phe
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Lys Tyr Ala Ser Glu Ser Ile Ser Gly Ile Pro Asp Arg Phe Ser
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Trp Ser Gly Gly Asn Thr Asp Tyr Asn Thr Pro Phe Thr Ser Arg
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Glu Ser Ile Ser Gly Ile Pro Asp Arg Phe Ser Gly Ser Gly
1               5                   10                  15

<210> SEQ ID NO 113
<211> LENGTH: 15
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 113

Gly Asn Thr Asp Tyr Asn Thr Pro Phe Thr Ser Arg Leu Thr Ile
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Ser Gly Ile Pro Asp Arg Phe Ser Gly Ser Gly Ser Gly Thr
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Tyr Asn Thr Pro Phe Thr Ser Arg Leu Thr Ile Asn Lys Asp
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ile Pro Asp Arg Phe Ser Gly Ser Gly Ser Gly Thr Asp Phe Thr
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Thr Pro Phe Thr Ser Arg Leu Thr Ile Asn Lys Asp Asn Ser Lys
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Phe Ser Gly Ser Gly Ser Gly Thr Asp Phe Thr Leu Thr Ile
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Thr Ser Arg Leu Thr Ile Asn Lys Asp Asn Ser Lys Asn Thr Val
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Ser Gly Ser Gly Thr Asp Phe Thr Leu Thr Ile Ser Arg Leu
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Thr Ile Asn Lys Asp Asn Ser Lys Asn Thr Val Tyr Leu Gln
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Gly Thr Asp Phe Thr Leu Thr Ile Ser Arg Leu Glu Pro Glu
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asn Lys Asp Asn Ser Lys Asn Thr Val Tyr Leu Gln Met Asn Ser
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
Asp Phe Thr Leu Thr Ile Ser Arg Leu Glu Pro Glu Asp Phe Ala
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asn Ser Lys Asn Thr Val Tyr Leu Gln Met Asn Ser Leu Arg Ala
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Leu Thr Ile Ser Arg Leu Glu Pro Glu Asp Phe Ala Val Tyr Tyr
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asn Thr Val Tyr Leu Gln Met Asn Ser Leu Arg Ala Glu Asp Thr
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Arg Leu Glu Pro Glu Asp Phe Ala Val Tyr Tyr Cys Gln Gln
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Tyr Leu Gln Met Asn Ser Leu Arg Ala Glu Asp Thr Ala Val Tyr
1               5                   10                  15

<210> SEQ ID NO 130
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 130

Glu Pro Glu Asp Phe Ala Val Tyr Tyr Cys Gln Gln Asn Asn Asn
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Met Asn Ser Leu Arg Ala Glu Asp Thr Ala Val Tyr Tyr Cys Ala
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Phe Ala Val Tyr Tyr Cys Gln Gln Asn Asn Asn Trp Pro Thr
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Leu Arg Ala Glu Asp Thr Ala Val Tyr Tyr Cys Ala Arg Ala Leu
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Val Tyr Tyr Cys Gln Gln Asn Asn Asn Trp Pro Thr Thr Phe Gly
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Glu Asp Thr Ala Val Tyr Tyr Cys Ala Arg Ala Leu Thr Tyr Tyr
1               5                   10                  15

<210> SEQ ID NO 136

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Gln Gln Asn Asn Asn Trp Pro Thr Thr Phe Gly Gln Gly Thr
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Val Tyr Tyr Cys Ala Arg Ala Leu Thr Tyr Tyr Asp Tyr Glu
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asn Asn Asn Trp Pro Thr Thr Phe Gly Gln Gly Thr Lys Leu Glu
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Tyr Cys Ala Arg Ala Leu Thr Tyr Tyr Asp Tyr Glu Phe Ala Tyr
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asn Trp Pro Thr Thr Phe Gly Gln Gly Thr Lys Leu Glu Ile Lys
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Arg Ala Leu Thr Tyr Tyr Asp Tyr Glu Phe Ala Tyr Trp Gly Gln
```

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Ile Leu Leu Thr Gln Ser Pro Gly Thr Leu Ser Leu Ser Pro
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Thr Tyr Tyr Asp Tyr Glu Phe Ala Tyr Trp Gly Gln Gly Thr Leu
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Leu Thr Gln Ser Pro Gly Thr Leu Ser Leu Ser Pro Gly Glu Arg
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asp Tyr Glu Phe Ala Tyr Trp Gly Gln Gly Thr Leu Val Thr Val
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Pro Gly Thr Leu Ser Leu Ser Pro Gly Glu Arg Ala Thr Leu
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Glu Phe Ala Tyr Trp Gly Gln Gly Thr Leu Val Thr Val Ser Ser
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Leu Ser Leu Ser Pro Gly Glu Arg Ala Thr Leu Ser Cys Arg
1               5                   10                  15

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asn Tyr Gly Trp Ser
1               5

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Trp Gly Val His
1               5

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asn Tyr Asp Val His
1               5

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asn Tyr Glu Val His
1               5

<210> SEQ ID NO 153
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 153

Asn Tyr Ala Val His
1               5

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asn Trp Ala Val His
1               5

<210> SEQ ID NO 155
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asn Trp Asp Val His
1               5

<210> SEQ ID NO 156
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asn Trp Glu Val His
1               5

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asn Tyr Asp Val His
1               5

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Val Ile Trp Ser Gly Gly Ala Thr Asp Tyr Asn Thr Pro Phe Thr Ser
1               5                   10                  15
```

```
<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Val Ile Trp Ser Gly Gly Asn Thr Asp Tyr Asn Thr Ser Leu Lys Ser
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Val Ile Trp Ser Gly Gly Asn Thr Asp Tyr Asn Thr Pro Leu Thr Ser
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Val Ile Trp Ser Gly Gly Asn Thr Asp Tyr Asn Thr Ser Val Lys Gly
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Tyr Ile Trp Ser Gly Gly Asn Thr Tyr Tyr Asn Pro Ser Leu Lys Ser
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Val Ile Trp Ser Gly Gly Ser Thr Asp Tyr Asn Thr Pro Phe Thr Ser
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164
```

```
Val Ile Trp Ser Gly Gly Asn Asp Asp Tyr Asn Thr Pro Phe Ala Ser
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asn Ile Trp Ser Gly Gly Asn Thr Asp Tyr Asn Thr Pro Phe Thr Ser
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Asn Ile Trp Ser Gly Gly Asn Pro Asp Tyr Asn Thr Pro Phe Thr Ser
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asn Ile Trp Ser Gly Gly Thr Pro Asp Tyr Asn Thr Pro Phe Thr Ser
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Val Ile Trp Ser Gly Gly Ala Thr Asp Tyr Asn Thr Pro Phe Ala Ser
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Val Ile Trp Ser Gly Gly Asn Thr Asp Tyr Asn Thr Pro Phe Ala Ser
1               5                   10                  15

<210> SEQ ID NO 170
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 170

Val Ile Trp Ser Gly Gly Ala Thr Asp Tyr Asn Thr Pro Phe Asn Ser
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Val Ile Trp Ser Gly Gly Thr Thr Asp Tyr Asn Thr Pro Phe Thr Ser
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Asn Ile Trp Ser Gly Gly Ala Pro Asp Tyr Asn Thr Pro Phe Thr Ser
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Val Ile Trp Ser Gly Gly Asn Pro Asp Tyr Asn Thr Pro Phe Thr Ser
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Val Ile Trp Ser Gly Gly Asn Thr Asp Tyr Asn Glu Pro Phe Thr Ser
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Val Ile Trp Ser Gly Gly Ala Thr Asp Tyr Asn Glu Pro Phe Thr Ser
1               5                   10                  15

<210> SEQ ID NO 176

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Leu Asp Tyr Tyr Asp Tyr Asn Phe Ala Tyr
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Leu Asp Tyr Tyr Asp Tyr Asp Phe Ala Tyr
1               5                   10

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Leu Asp Tyr Tyr Asp Tyr Glu Asp Ala Tyr
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Leu Asp Tyr Tyr Asp Tyr Asp Tyr Ala Tyr
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Leu Asp Tyr Tyr Asp Tyr Glu Phe Ala Tyr
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Arg Ala Ser Glu Ser Ile Gly Thr Asn Ile His
```

-continued

<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Arg Ala Ser Phe Ser Ile Gly Thr Asn Ile His
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Ala Ser Tyr Ser Ile Gly Thr Asn Ile His
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Ala Ser His Ser Ile Gly Thr Asn Ile His
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Arg Ala Ser Gln Ser Ile Gly Thr Asn Leu His
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Ala Asp Gln Ser Ile Gly Thr Asn Ile His
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Arg Ala Ser Gln Ser Ile Gly Glu Asn Ile His
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Ala Asp Gln Ser Ile Gly Glu Asn Ile His
1               5                   10

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Gln Asn Asn Asn Trp Pro Leu Thr
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Gln Asn Asn Asp Trp Pro Thr Thr
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gln Gln Asn Asn Glu Trp Pro Thr Thr
1               5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gln Gln Asn Asn Asn Trp Pro Thr Ser
1               5

<210> SEQ ID NO 193
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 193

Gln Gln Asn Asn Asp Trp Pro Thr Ser
1               5

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gln Gln Asn Asn Glu Trp Pro Thr Ser
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Gln Asn Asn Lys Trp Pro Thr Ser
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

His Gln Asn Asn Asn Trp Pro Thr Thr
1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln Gln Asn Asn Ala Trp Pro Thr Thr
1               5

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Leu Thr Tyr Tyr Cys Tyr Glu Phe Ala Tyr
1               5                   10
```

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Leu Thr Tyr Tyr Asp Tyr Glu Phe Cys Tyr
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Arg Ala Ser Gln Ser Ile Gly Thr Asn Ile Cys
1               5                   10

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Val Tyr Gly Val His
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asn Arg Gly Val His
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asn Tyr Gly Leu His
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

```
Asn Tyr Gly Asn His
1               5

<210> SEQ ID NO 205
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Leu Ile Trp Ser Gly Gly Asn Thr Asp Tyr Asn Thr Pro Phe Thr Ser
1               5                   10                  15

<210> SEQ ID NO 206
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gln Ile Trp Ser Gly Gly Asn Thr Asp Tyr Asn Thr Pro Phe Thr Ser
1               5                   10                  15

<210> SEQ ID NO 207
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Val Gly Trp Ser Gly Gly Asn Thr Asp Tyr Asn Thr Pro Phe Thr Ser
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Val Met Trp Ser Gly Gly Asn Thr Asp Tyr Asn Thr Pro Phe Thr Ser
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Val Ser Trp Ser Gly Gly Asn Thr Asp Tyr Asn Thr Pro Phe Thr Ser
1               5                   10                  15

<210> SEQ ID NO 210
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 210

Val Gln Trp Ser Gly Gly Asn Thr Asp Tyr Asn Thr Pro Phe Thr Ser
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Ile Gly Ser Gly Gly Asn Thr Asp Tyr Asn Thr Pro Phe Thr Ser
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Val Ile Thr Ser Gly Gly Asn Thr Asp Tyr Asn Thr Pro Phe Thr Ser
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Val Ile Trp Gln Gly Gly Asn Thr Asp Tyr Asn Thr Pro Phe Thr Ser
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Val Ile Trp Thr Gly Gly Asn Thr Asp Tyr Asn Thr Pro Phe Thr Ser
1               5                   10                  15

<210> SEQ ID NO 215
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Val Ile Trp Ser Gly Asp Asn Thr Asp Tyr Asn Thr Pro Phe Thr Ser
1               5                   10                  15

<210> SEQ ID NO 216

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Val Ile Trp Ser Gly Gly Gly Thr Asp Tyr Asn Thr Pro Phe Thr Ser
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Val Ile Trp Ser Gly Gly Asn Ala Asp Tyr Asn Thr Pro Phe Thr Ser
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Val Ile Trp Ser Gly Gly Asn Asp Asp Tyr Asn Thr Pro Phe Thr Ser
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Val Ile Trp Ser Gly Gly Asn Gly Asp Tyr Asn Thr Pro Phe Thr Ser
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Val Ile Trp Ser Gly Gly Asn Ser Asp Tyr Asn Thr Pro Phe Thr Ser
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Val Ile Trp Ser Gly Gly Asn Thr Asp Ala Asn Thr Pro Phe Thr Ser
```

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Val Ile Trp Ser Gly Gly Asn Thr Asp Cys Asn Thr Pro Phe Thr Ser
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Val Ile Trp Ser Gly Gly Asn Thr Asp Glu Asn Thr Pro Phe Thr Ser
1               5                   10                  15

<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Val Ile Trp Ser Gly Gly Asn Thr Asp Phe Asn Thr Pro Phe Thr Ser
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Val Ile Trp Ser Gly Gly Asn Thr Asp Gly Asn Thr Pro Phe Thr Ser
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Val Ile Trp Ser Gly Gly Asn Thr Asp Ser Asn Thr Pro Phe Thr Ser
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 227

Val Ile Trp Ser Gly Gly Asn Thr Asp Trp Asn Thr Pro Phe Thr Ser
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Val Ile Trp Ser Gly Gly Asn Thr Asp Tyr Asp Thr Pro Phe Thr Ser
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Val Ile Trp Ser Gly Gly Asn Thr Asp Tyr Asn Thr Pro Phe Glu Ser
1               5                   10                  15

<210> SEQ ID NO 230
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 230

Ala Leu Thr Trp Tyr Asp Tyr Glu Phe Ala Tyr
1               5                   10

<210> SEQ ID NO 231
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 231

Arg Val Ser Gln Ser Ile Gly Thr Asn Ile His
1               5                   10

<210> SEQ ID NO 232
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments
```

-continued

```
<400> SEQUENCE: 232

Arg Ser Ser Gln Ser Ile Gly Thr Asn Ile His
1               5                   10

<210> SEQ ID NO 233
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 233

Arg Ala Ser Gln Ser Ile Tyr Thr Asn Ile His
1               5                   10

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 234

Gln Gln Leu Asn Asn Trp Pro Thr Thr
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 235

Gln Gln Asn Leu Asn Trp Pro Thr Thr
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 236

Gln Gln Asn Arg Asn Trp Pro Thr Thr
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<223> OTHER INFORMATION: see specification as filed for detailed
      description of substitutions and preferred embodiments

<400> SEQUENCE: 237

Gln Gln Asn Asn Asn Trp Pro Thr Ala
1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 238

Gln Gln Asn Asn Asn Trp Pro Thr Asp
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 239

Gln Gln Asn Asn Asn Trp Pro Thr Glu
1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 240

Gln Gln Asn Asn Asn Trp Pro Thr Pro
1               5

<210> SEQ ID NO 241
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 241

Val Ile Trp Ser Gly Gly Asn Thr Asp His Asn Thr Pro Phe Thr Ser
1               5                   10                  15

<210> SEQ ID NO 242
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 242

Pro Ala Ser Gln Ser Ile Gly Thr Asn Ile His
1               5                   10

<210> SEQ ID NO 243
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 243

Arg Cys Ser Gln Ser Ile Gly Thr Asn Ile His
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 244

Arg Phe Ser Gln Ser Ile Gly Thr Asn Ile His
1               5                   10

<210> SEQ ID NO 245
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 245

Arg Met Ser Gln Ser Ile Gly Thr Asn Ile His
1               5                   10

<210> SEQ ID NO 246
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 246
```

-continued

Arg Leu Ser Gln Ser Ile Gly Thr Asn Ile His
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 247

Arg Ala Ser Trp Ser Ile Gly Thr Asn Ile His
1               5                   10

<210> SEQ ID NO 248
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 248

Arg Ala Ser Gln Arg Ile Gly Thr Asn Ile His
1               5                   10

<210> SEQ ID NO 249
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 249

Arg Ala Ser Gln Ser Ile Trp Thr Asn Ile His
1               5                   10

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 250

Arg Ala Ser Gln Ser Ile Phe Thr Asn Ile His
1               5                   10

<210> SEQ ID NO 251
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: see specification as filed for detailed
      description of substitutions and preferred embodiments

<400> SEQUENCE: 251

Arg Ala Ser Gln Ser Ile Thr Thr Asn Ile His
1               5                   10

<210> SEQ ID NO 252
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 252

Arg Ala Ser Gln Ser Ile Met Thr Asn Ile His
1               5                   10

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 253

Arg Ala Ser Gln Ser Ile Ser Thr Asn Ile His
1               5                   10

<210> SEQ ID NO 254
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 254

Arg Ala Ser Gln Ser Ile Gly Val Asn Ile His
1               5                   10

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 255

Arg Ala Ser Gln Ser Ile Gly Glu Asn Ile His
1               5                   10

<210> SEQ ID NO 256
<211> LENGTH: 11
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 256

Arg Ala Ser Gln Ser Ile Gly Thr His Ile His
1               5                   10

<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 257

Gln Gln Asn Asn Asn Trp Pro Thr Ile
1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 258

Gln Gln Asn Asn Asn Trp Pro Thr Gly
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 259

Gln Gln Asn Asn Asn Trp Pro Thr Leu
1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 260

Gln Gln Asn Asn Asn Trp Pro Thr His
1               5

```
<210> SEQ ID NO 261
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 261

Gln Gln Asn Asn Asn Trp Pro Thr Arg
1               5

<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 262

Asp Tyr Gly Val His
1               5

<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 263

Ile Tyr Gly Val His
1               5

<210> SEQ ID NO 264
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 264

Asn Tyr Gly Glu His
1               5

<210> SEQ ID NO 265
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments
```

```
<400> SEQUENCE: 265

Asn Tyr Gly Gln His
1               5

<210> SEQ ID NO 266
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 266

Glu Ile Trp Ser Gly Gly Asn Thr Asp Tyr Asn Thr Pro Phe Thr Ser
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 267

Ile Ile Trp Ser Gly Gly Asn Thr Asp Tyr Asn Thr Pro Phe Thr Ser
1               5                   10                  15

<210> SEQ ID NO 268
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 268

Val Ala Trp Ser Gly Gly Asn Thr Asp Tyr Asn Thr Pro Phe Thr Ser
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 269

Val Cys Trp Ser Gly Gly Asn Thr Asp Tyr Asn Thr Pro Phe Thr Ser
1               5                   10                  15

<210> SEQ ID NO 270
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 270

Val Ile Trp Asn Gly Gly Asn Thr Asp Tyr Asn Thr Pro Phe Thr Ser
1               5                   10                  15

<210> SEQ ID NO 271
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 271

Val Ile Trp Ser Gly Ala Asn Thr Asp Tyr Asn Thr Pro Phe Thr Ser
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 272

Val Ile Trp Ser Gly Glu Asn Thr Asp Tyr Asn Thr Pro Phe Thr Ser
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 273

Val Ile Trp Ser Gly His Asn Thr Asp Tyr Asn Thr Pro Phe Thr Ser
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 274

Val Ile Trp Ser Gly Gly Asn Glu Asp Tyr Asn Thr Pro Phe Thr Ser
1               5                   10                  15
```

```
<210> SEQ ID NO 275
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 275

Val Ile Trp Ser Gly Gly Asn Thr Asp Pro Asn Thr Pro Phe Thr Ser
1               5                   10                  15

<210> SEQ ID NO 276
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 276

Val Ile Trp Ser Gly Gly Asn Thr Asp Gln Asn Thr Pro Phe Thr Ser
1               5                   10                  15

<210> SEQ ID NO 277
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 277

Arg Ile Ser Gln Ser Ile Gly Thr Asn Ile His
1               5                   10

<210> SEQ ID NO 278
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 278

Arg Pro Ser Gln Ser Ile Gly Thr Asn Ile His
1               5                   10

<210> SEQ ID NO 279
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 279
```

Arg Thr Ser Gln Ser Ile Gly Thr Asn Ile His
1               5                   10

<210> SEQ ID NO 280
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 280

Arg Tyr Ser Gln Ser Ile Gly Thr Asn Ile His
1               5                   10

<210> SEQ ID NO 281
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 281

Arg Ala Ser Gln Ser Ile Cys Thr Asn Ile His
1               5                   10

<210> SEQ ID NO 282
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 282

Arg Ala Ser Gln Ser Ile His Thr Asn Ile His
1               5                   10

<210> SEQ ID NO 283
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 283

Arg Ala Ser Gln Ser Ile Lys Thr Asn Ile His
1               5                   10

<210> SEQ ID NO 284
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: see specification as filed for detailed
      description of substitutions and preferred embodiments

<400> SEQUENCE: 284

Arg Ala Ser Gln Ser Ile Gln Thr Asn Ile His
1               5                   10

<210> SEQ ID NO 285
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 285

Arg Ala Ser Gln Ser Ile Arg Thr Asn Ile His
1               5                   10

<210> SEQ ID NO 286
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 286

Gln Gln Asn Lys Asn Trp Pro Thr Thr
1               5

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 287

Gln Gln Asn Met Asn Trp Pro Thr Thr
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 288

Gln Gln Asn Asn Asn Trp Pro Thr Cys
1               5

<210> SEQ ID NO 289
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 289

Gln Gln Asn Asn Asn Trp Pro Thr Lys
1               5

<210> SEQ ID NO 290
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 290

Gln Gln Asn Asn Asn Trp Pro Thr Asn
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 291

Gln Gln Asn Asn Asn Trp Pro Thr Gln
1               5

<210> SEQ ID NO 292
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 292

Val Ile Trp Ser Gly Gly Asn Thr Asp Tyr Asn Thr Pro Val Thr Ser
1               5                   10                  15

<210> SEQ ID NO 293
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 293

Ala Leu Thr Tyr Tyr Asp Tyr Glu Tyr Ala Tyr
```

<210> SEQ ID NO 294
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 294

Asn Trp Gly Val His
1               5

<210> SEQ ID NO 295
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 295

Asn Tyr Ala Val His
1               5

<210> SEQ ID NO 296
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 296

Asn Tyr Asp Val His
1               5

<210> SEQ ID NO 297
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 297

Asn Tyr Glu Val His
1               5

<210> SEQ ID NO 298
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed -continued description of substitutions and preferred embodiments

<400> SEQUENCE: 298

Val Ile Trp Ser Gly Gly Asn Pro Asp Tyr Asn Thr Pro Phe Thr Ser
1               5                   10                  15

<210> SEQ ID NO 299
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 299

Val Ile Trp Ser Gly Gly Ala Thr Asp Tyr Asn Thr Pro Phe Thr Ser
1               5                   10                  15

<210> SEQ ID NO 300
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 300

Val Ile Trp Ser Gly Gly Asn Thr Asp Tyr Asn Glu Pro Phe Thr Ser
1               5                   10                  15

<210> SEQ ID NO 301
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 301

Ala Leu Asp Tyr Tyr Asp Tyr Glu Phe Ala Tyr
1               5                   10

<210> SEQ ID NO 302
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 302

Arg Ala Ser Glu Ser Ile Gly Thr Asn Ile His
1               5                   10

<210> SEQ ID NO 303
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 303

Arg Ala Ser Phe Ser Ile Gly Thr Asn Ile His
1               5                   10

<210> SEQ ID NO 304
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 304

Arg Ala Ser Tyr Ser Ile Gly Thr Asn Ile His
1               5                   10

<210> SEQ ID NO 305
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 305

Arg Ala Asp Gln Ser Ile Gly Thr Asn Ile His
1               5                   10

<210> SEQ ID NO 306
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 306

Arg Ala Ser Gln Ser Ile Gly Glu Asn Ile His
1               5                   10

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 307

Gln Gln Asn Asn Asn Trp Pro Leu Thr
1               5
```

```
<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 308

Gln Gln Asn Asn Asp Trp Pro Thr Thr
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 309

Gln Gln Asn Asn Glu Trp Pro Thr Thr
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 310

Gln Gln Asn Asn Ala Trp Pro Thr Thr
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 311

Gln Gln Asn Asn Asn Trp Pro Thr Ser
1               5

<210> SEQ ID NO 312
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments
```

```
<400> SEQUENCE: 312

Ala Leu Thr Trp Tyr Asp Tyr Glu Phe Ala Tyr
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Arg Val Ser Gln Ser Ile Gly Thr Asn Ile His
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Arg Ser Ser Gln Ser Ile Gly Thr Asn Ile His
1               5                   10

<210> SEQ ID NO 315
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Arg Ala Ser Gln Ser Ile Tyr Thr Asn Ile His
1               5                   10

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gln Gln Leu Asn Asn Trp Pro Thr Thr
1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Gln Asn Leu Asn Trp Pro Thr Thr
1               5

<210> SEQ ID NO 318
<211> LENGTH: 9
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 318

Gln Gln Asn Arg Asn Trp Pro Thr Thr
1               5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gln Gln Asn Asn Asn Trp Pro Thr Ala
1               5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gln Gln Asn Asn Asn Trp Pro Thr Asp
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Gln Asn Asn Asn Trp Pro Thr Glu
1               5

<210> SEQ ID NO 322
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Val Ile Trp Ser Gly Gly Asn Thr Asp His Asn Thr Pro Phe Thr Ser
1               5                   10                  15

<210> SEQ ID NO 323
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Pro Ala Ser Gln Ser Ile Gly Thr Asn Ile His
1               5                   10
```

```
<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Arg Cys Ser Gln Ser Ile Gly Thr Asn Ile His
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Arg Phe Ser Gln Ser Ile Gly Thr Asn Ile His
1               5                   10

<210> SEQ ID NO 326
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Arg Met Ser Gln Ser Ile Gly Thr Asn Ile His
1               5                   10

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Arg Leu Ser Gln Ser Ile Gly Thr Asn Ile His
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Arg Ala Ser Trp Ser Ile Gly Thr Asn Ile His
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329
```

```
Arg Ala Ser Gln Arg Ile Gly Thr Asn Ile His
1               5                   10

<210> SEQ ID NO 330
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Arg Ala Ser Gln Ser Ile Trp Thr Asn Ile His
1               5                   10

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Arg Ala Ser Gln Ser Ile Phe Thr Asn Ile His
1               5                   10

<210> SEQ ID NO 332
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Arg Ala Ser Gln Ser Ile Thr Thr Asn Ile His
1               5                   10

<210> SEQ ID NO 333
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Arg Ala Ser Gln Ser Ile Met Thr Asn Ile His
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Arg Ala Ser Gln Ser Ile Ser Thr Asn Ile His
1               5                   10

<210> SEQ ID NO 335
<211> LENGTH: 11
<212> TYPE: PRT
<213> ORGANISM: Artificial Sequence
<220> FEATURE:
<223> OTHER INFORMATION: Description of Artificial Sequence: Synthetic
```

-continued

```
                        peptide

<400> SEQUENCE: 335

Arg Ala Ser Gln Ser Ile Gly Val Asn Ile His
1               5                   10

<210> SEQ ID NO 336
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Arg Ala Ser Gln Ser Ile Gly Glu Asn Ile His
1               5                   10

<210> SEQ ID NO 337
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Arg Ala Ser Gln Ser Ile Gly Thr His Ile His
1               5                   10

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gln Gln Asn Asn Asn Trp Pro Thr Ile
1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Gln Gln Asn Asn Asn Trp Pro Thr Gly
1               5

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gln Gln Asn Asn Asn Trp Pro Thr Leu
1               5

<210> SEQ ID NO 341
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Gln Gln Asn Asn Asn Trp Pro Thr His
1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Gln Gln Asn Asn Asn Trp Pro Thr Arg
1               5

<210> SEQ ID NO 343
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Asp Tyr Gly Val His
1               5

<210> SEQ ID NO 344
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ile Tyr Gly Val His
1               5

<210> SEQ ID NO 345
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Thr Tyr Gly Val His
1               5

<210> SEQ ID NO 346
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Asn Tyr Gly Glu His
1               5
```

<210> SEQ ID NO 347
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Asn Tyr Gly Gln His
1               5

<210> SEQ ID NO 348
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Glu Ile Trp Ser Gly Gly Asn Thr Asp Tyr Asn Thr Pro Phe Thr Ser
1               5                   10                  15

<210> SEQ ID NO 349
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ile Ile Trp Ser Gly Gly Asn Thr Asp Tyr Asn Thr Pro Phe Thr Ser
1               5                   10                  15

<210> SEQ ID NO 350
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Val Ala Trp Ser Gly Gly Asn Thr Asp Tyr Asn Thr Pro Phe Thr Ser
1               5                   10                  15

<210> SEQ ID NO 351
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Val Cys Trp Ser Gly Gly Asn Thr Asp Tyr Asn Thr Pro Phe Thr Ser
1               5                   10                  15

<210> SEQ ID NO 352
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 352

Val Ile Trp Asn Gly Gly Asn Thr Asp Tyr Asn Thr Pro Phe Thr Ser
1               5                   10                  15

<210> SEQ ID NO 353
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Val Ile Trp Ser Gly Ala Asn Thr Asp Tyr Asn Thr Pro Phe Thr Ser
1               5                   10                  15

<210> SEQ ID NO 354
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Val Ile Trp Ser Gly Glu Asn Thr Asp Tyr Asn Thr Pro Phe Thr Ser
1               5                   10                  15

<210> SEQ ID NO 355
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Val Ile Trp Ser Gly His Asn Thr Asp Tyr Asn Thr Pro Phe Thr Ser
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Val Ile Trp Ser Gly Gly Asn Glu Asp Tyr Asn Thr Pro Phe Thr Ser
1               5                   10                  15

<210> SEQ ID NO 357
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Val Ile Trp Ser Gly Gly Asn Thr Asp Pro Asn Thr Pro Phe Thr Ser
1               5                   10                  15

<210> SEQ ID NO 358
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 358

Val Ile Trp Ser Gly Gly Asn Thr Asp Gln Asn Thr Pro Phe Thr Ser
1               5                   10                  15

<210> SEQ ID NO 359
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Arg Ile Ser Gln Ser Ile Gly Thr Asn Ile His
1               5                   10

<210> SEQ ID NO 360
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Arg Pro Ser Gln Ser Ile Gly Thr Asn Ile His
1               5                   10

<210> SEQ ID NO 361
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Arg Thr Ser Gln Ser Ile Gly Thr Asn Ile His
1               5                   10

<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Arg Tyr Ser Gln Ser Ile Gly Thr Asn Ile His
1               5                   10

<210> SEQ ID NO 363
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Arg Ala Ser Gln Ser Ile Cys Thr Asn Ile His
1               5                   10
```

<210> SEQ ID NO 364
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Arg Ala Ser Gln Ser Ile His Thr Asn Ile His
1               5                   10

<210> SEQ ID NO 365
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Arg Ala Ser Gln Ser Ile Lys Thr Asn Ile His
1               5                   10

<210> SEQ ID NO 366
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Arg Ala Ser Gln Ser Ile Gln Thr Asn Ile His
1               5                   10

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Arg Ala Ser Gln Ser Ile Arg Thr Asn Ile His
1               5                   10

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gln Gln Asn Lys Asn Trp Pro Thr Thr
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

```
Gln Gln Asn Met Asn Trp Pro Thr Thr
1               5
```

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

```
Gln Gln Asn Asn Asn Trp Pro Thr Cys
1               5
```

<210> SEQ ID NO 371
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

```
Gln Gln Asn Asn Asn Trp Pro Thr Lys
1               5
```

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

```
Gln Gln Asn Asn Asn Trp Pro Thr Asn
1               5
```

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

```
Gln Gln Asn Asn Asn Trp Pro Thr Gln
1               5
```

<210> SEQ ID NO 374
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

```
Asn Tyr Gly Ser His
1               5
```

<210> SEQ ID NO 375
<211> LENGTH: 16
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 375

Val Val Trp Ser Gly Gly Asn Thr Asp Tyr Asn Thr Pro Phe Thr Ser
1               5                   10                  15

<210> SEQ ID NO 376
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Val Ile Trp Ser Gly Phe Asn Thr Asp Tyr Asn Thr Pro Phe Thr Ser
1               5                   10                  15

<210> SEQ ID NO 377
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Val Ile Trp Ser Gly Gly Ser Thr Asp Tyr Asn Thr Pro Phe Thr Ser
1               5                   10                  15

<210> SEQ ID NO 378
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Val Ile Trp Ser Gly Gly Asn Thr Asp Tyr Ala Thr Pro Phe Thr Ser
1               5                   10                  15

<210> SEQ ID NO 379
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ala Leu Thr Tyr Tyr Asp Tyr Glu Phe Ala Phe
1               5                   10

<210> SEQ ID NO 380
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Arg Trp Ser Gln Ser Ile Gly Thr Asn Ile His
1               5                   10

<210> SEQ ID NO 381
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Arg Ala Ser Thr Ser Ile Gly Thr Asn Ile His
1               5                   10

<210> SEQ ID NO 382
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Arg Ala Ser Gln Phe Ile Gly Thr Asn Ile His
1               5                   10

<210> SEQ ID NO 383
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Arg Ala Ser Gln Ser Ile Ala Thr Asn Ile His
1               5                   10

<210> SEQ ID NO 384
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Arg Ala Ser Gln Ser Ile Gly Arg Asn Ile His
1               5                   10

<210> SEQ ID NO 385
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Tyr Ala Ser Glu Val Ile Ser
1               5

<210> SEQ ID NO 386
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Gln Gln Asn Asn Val Trp Pro Thr Thr
1               5
```

```
<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gln Gln Asn Asn Asn Trp Pro Thr Arg
1               5
```